(12) United States Patent
Bonnert et al.

(10) Patent No.: US 7,709,511 B2
(45) Date of Patent: May 4, 2010

(54) BENZOTHIAZOLONE DERIVATIVES

(75) Inventors: Roger Bonnert, Loughborough (GB);
Alice Flaherty, Carrigaline (IE); Garry Pairaudeau, Loughborough (GB);
Michael Stocks, Loughborough (GB)

(73) Assignee: AstraZeneca AB (SE)

( * ) Notice: Subject to any disclaimer, the term of this patent is extended or adjusted under 35 U.S.C. 154(b) by 130 days.

(21) Appl. No.: 12/063,322

(22) PCT Filed: Aug. 3, 2006

(86) PCT No.: PCT/SE2006/000927

§ 371 (c)(1),
(2), (4) Date: Jun. 9, 2008

(87) PCT Pub. No.: WO2007/018461

PCT Pub. Date: Feb. 15, 2007

(65) Prior Publication Data

US 2008/0300275 A1 Dec. 4, 2008

(30) Foreign Application Priority Data

| Aug. 9, 2005 | (SE) | ................................ | 0501793 |
| Aug. 30, 2005 | (SE) | ................................ | 0501914 |
| Mar. 8, 2006 | (SE) | ................................ | 0600515 |

(51) Int. Cl.
*C07D 277/68* (2006.01)
*A61K 31/428* (2006.01)

(52) U.S. Cl. .................................. 514/367; 548/171

(58) Field of Classification Search .................. None
See application file for complete search history.

(56) References Cited

U.S. PATENT DOCUMENTS

| 2,653,977 | A | 9/1953 | Craig et al. |
| 3,775,477 | A | 11/1973 | Diana |
| 4,145,542 | A | 3/1979 | Nakagawa et al. |
| 4,460,581 | A | 7/1984 | Schromm et al. |
| 5,648,370 | A | 7/1997 | Bonnert et al. |
| 6,686,353 | B1 | 2/2004 | Shiota et al. |
| 2002/0055651 | A1 | 5/2002 | Moran et al. |
| 2003/0229058 | A1 | 12/2003 | Moran et al. |
| 2008/0207698 | A1 | 8/2008 | Connolly et al. |
| 2008/0242649 | A1 | 10/2008 | Cadogan et al. |
| 2008/0249145 | A1 | 10/2008 | Whittock et al. |
| 2009/0062259 | A1 | 3/2009 | Alcaraz et al. |
| 2009/0203753 | A1 | 8/2009 | Bailey et al. |
| 2009/0221653 | A1 | 9/2009 | Bailey et al. |

FOREIGN PATENT DOCUMENTS

| EP | 0162576 | 11/1985 |
| EP | 0174811 | 3/1986 |
| EP | 0175525 | 3/1986 |
| EP | 0220878 | 5/1987 |
| EP | 0303466 | 2/1989 |
| EP | 0422889 | 4/1991 |
| JP | 2005-187357 | 7/2005 |
| SE | 7415945 | 6/1975 |
| WO | WO 92/08708 A1 | 5/1992 |
| WO | WO 93/23385 A1 | 11/1993 |
| WO | WO 93/24473 A1 | 12/1993 |
| WO | WO 97/10227 A1 | 3/1997 |
| WO | WO 97/23470 | 7/1997 |
| WO | WO 97/44329 | 11/1997 |
| WO | WO 98/38180 | 9/1998 |
| WO | WO 98/45294 | 10/1998 |
| WO | WO 99/36095 | 7/1999 |
| WO | WO 99/64035 | 12/1999 |
| WO | WO 00/75114 | 12/2000 |
| WO | WO 01/11933 | 2/2001 |
| WO | WO 01/12167 | 2/2001 |
| WO | WO 01/12191 | 2/2001 |
| WO | WO 01/12192 | 2/2001 |
| WO | WO 01/42193 | 6/2001 |
| WO | WO 02/06255 | 1/2002 |
| WO | WO 02/076933 | 10/2002 |
| WO | WO 03/024439 | 3/2003 |
| WO | WO 2004/016578 A2 | 2/2004 |
| WO | WO 2004/016578 A3 | 2/2004 |
| WO | WO 2004/016601 A1 | 2/2004 |
| WO | WO 2004/039766 | 5/2004 |
| WO | WO 2004/071388 | 8/2004 |
| WO | WO 2004/074276 | 9/2004 |
| WO | WO 2004/089892 | 10/2004 |
| WO | WO 2005/030678 | 4/2005 |
| WO | WO 2005/040103 | 5/2005 |

(Continued)

OTHER PUBLICATIONS

Austin et al. J. Med. Chem. 2003, 46, 3210-3220.*

(Continued)

*Primary Examiner*—Rebecca L Anderson
*Assistant Examiner*—Matthew P Coughlin
(74) *Attorney, Agent, or Firm*—Fish & Richardson P.C.

(57) ABSTRACT

The present invention provides compounds of formula (I) wherein e, $R^1$, $R^2$, $R^3$, $R^4$, $R^5$, $R^{4'}$, $R^{5'}$, $R^6$, $R^7$, $R^{7a}$, $R^{7b}$, A, D, m and n are as defined in the specification, processes for their preparation, pharmaceutical compositions containing them and their use in therapy.

(I)

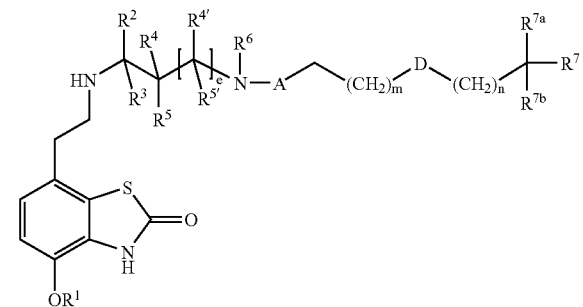

6 Claims, No Drawings

FOREIGN PATENT DOCUMENTS

| | | |
|---|---|---|
| WO | WO 2005/044787 | 5/2005 |
| WO | WO 2005/070872 | 8/2005 |
| WO | WO 2005/074924 | 8/2005 |
| WO | WO 2005/092841 | 10/2005 |
| WO | WO 2005/092861 | 10/2005 |
| WO | WO 2005/092870 | 10/2005 |
| WO | WO 2005/110990 | 11/2005 |
| WO | WO 2005/111002 | 11/2005 |
| WO | WO 2005/111004 | 11/2005 |
| WO | WO 2005/121065 | 12/2005 |
| WO | WO 2006/014704 | 2/2006 |
| WO | WO 2006/023457 | 3/2006 |
| WO | WO 2006/023460 | 3/2006 |
| WO | WO 2006/031556 | 3/2006 |
| WO | WO 2006/056471 | 6/2006 |
| WO | WO 2006/074897 | 7/2006 |
| WO | WO 2006/128675 | 12/2006 |
| WO | WO 2007/010356 | 1/2007 |
| WO | WO 2007/018461 | 2/2007 |
| WO | WO 2007/027133 | 3/2007 |
| WO | WO 2007/027134 | 3/2007 |
| WO | WO 2007/102771 | 9/2007 |
| WO | WO 2007/106016 | 9/2007 |
| WO | WO 2009/037503 | 3/2008 |
| WO | WO 2008/041914 | 4/2008 |
| WO | WO 2008/075025 | 6/2008 |
| WO | WO 2008/075026 | 6/2008 |
| WO | WO 2008/096111 | 8/2008 |
| WO | WO 2008/096112 | 8/2008 |
| WO | WO 2008/096119 | 8/2008 |
| WO | WO 2008/096121 | 8/2008 |
| WO | WO 2008/104776 | 9/2008 |
| WO | WO 2008/104790 | 9/2008 |

OTHER PUBLICATIONS

Rupert et al., "QSAR and the Rational Design of Long-Acting Dual $D_2$-Receptor/$\beta_2$-Adrenoceptor Agonists", *J. Med. Chem.* 46:3210-3220 (2003).

Berge et al. "Pharmaceutical Salts" J Pharmaceutical Sciences. 1977 66(1) 1-19.

Bonnert et al. "Dual $D_2$-Receptor and $\beta_2$-Adrenoceptor Agonists for the Treatment of Airway Diseases. 1. Discovery and Biological Evaluation of Some 7-(2-Aminoethyl)-4-hydroxybenzothiazol-2(3$H$)-one Analogues" J Med Chem. 1998 (41) 4915-4917.

Davies et al. "Indacaterol. Asthma Therapy Treatment of COPD $\beta_2$-Adrenoceptor Agonist" Drugs of the Future. 2005 30(12) 1219-1224.

Dougall et al. "Dual dopamine $D_2$ receptor and $\beta_2$-adrenoceptor agonists for the treatment of chronic obstructive pulmonary disease: the pre-clinical rationale" Respir Med (Suppl A). 2003 (97) S3-S7 (Abstract).

Fernández et al. "Alkaline Hydrolysis of 1,2,3-Trisubstituted Cyclic Amidinium Salts. Kinetic Study of N—N' Acyl Migration in Alkaline Solution in an Ethylenediamine Derivative" J.C.S. Perkin II. 1978 545-550.

Fernández et al. "N—N' Intramolecular Acyl Transfer in Acid Media for Alkylenediamine Derivatives" J.C.S. Perkin II. 1978 550-553.

Norman, "Which of three structures is AZD-3199? WO-2008104790, WO-2008096112 and WO-2008096119" Expert Opin. Ther. Patents. 2009 19(7) 1-7.

Weinstock et al. "Synthesis and Evaluation of Non-Catechol D-1 and D-2 Dopamine Receptor Agonists: Benzimidazol-2-one, Benzoxazol-2-one, and the Highly Potent Benzothiazol-2-one 7 Ethylamines" J Med Chem. 1987 (30) 1166-1176.

Wermuth et al., Handbook of Pharmaceutical salts: properties, selection and use, (2002) pp. 1-7: published by Wiley-VCH Verlag, ISBN: 10-3-906390-26-8.

Wright et al. "The Rearrangement of *N*-(Methylaminoalkyl)anilides" J Org Chem. 1961 26(6) 2120-2123.

\* cited by examiner

BENZOTHIAZOLONE DERIVATIVES

CROSS-REFERENCE TO RELATED APPLICATIONS

This application is a national phase application under 35 U.S.C. §371 of PCT International Application No. PCT/SE2006/000927, filed Aug. 3, 2006, which claims the benefit of Swedish Application Serial No. 0501793-4, filed Aug. 9, 2005, Swedish Application Serial No. 0501914-6, filed Aug. 30, 2005 and Swedish Application Serial No. 0600515-1, filed Mar. 8, 2006. Each of these prior applications is incorporated herein by reference in its entirety.

The present invention relates to benzothiazolone derivatives, processes for their preparation, pharmaceutical compositions containing them and their use in therapy.

Adreneoceptors are a group of G-protein coupled receptors divided into two major sub-families, α and β. These sub-families are further divided into sub-types of which the β sub-family has at least 3 members: β1, β2 and β3. β2 adrenoceptors (henceforth referred to as β2 receptors) are mainly expressed on smooth muscle cells.

Agonism of the β2 receptor on airway smooth muscle produces relaxation and therefore bronchodilatation. Through this mechanism, β2 agonists act as functional antagonists to all bronchoconstrictor substances such as the naturally-occurring histamine and acetylcholine as well as the experimental substances methacholine and carbachol. β2 agonists are widely used to treat airways diseases including asthma and chronic obstructive pulmonary disease (COPD), and this has been extensively reviewed in the literature and incorporated into national guidelines for the treatment of these diseases (British Guideline on the Management of Asthma, NICE guideline No. 12 on the Management of COPD).

β2 agonists are classed either as short-acting or long-acting. Short-acting β2 agonists (SABAs) such as salbutamol have a duration of action of 2-4 hours. They are suitable for rescue medication during a period of acute bronchoconstriction but are not suitable for continuous medication because the beneficial effect of these drugs wears off during the night. Long-acting β2 agonists (LABAs) currently have a duration of action of about 12 hours and are administered twice daily to provide continuous bronchodilatation. They are particularly effective when administered in combination with inhaled corticosteroids. This benefit is not seen when inhaled corticosteroids are combined with SABAs (Kips and Pauwels, *Am. J. Respir. Crit. Care Med.*, 2001, 164, 923-932). LABAs are recommended as add-on therapy to patients already receiving inhaled corticosteroids for asthma to reduce nocturnal awakening and reduce the incidence of exacerbations of the disease. Corticosteroids and LABAs are conveniently co-administered in a single inhaler to improve patient compliance.

There are shortcomings to existing LABAs and there is a need for a new drug in this class. Salmeterol, a commonly used LABA, has a narrow safety margin and side effects related to systemic agonism of β2 receptors (such as tremor, hypokalemia, tachycardia and hypertension) are common. Salmeterol also has a long onset of action which precludes its use as both a rescue and a maintenance therapy. All current LABAs are administered twice daily and there is a medical need for once daily treatments to improve treatment and patient compliance. Such once daily compounds, co-administered with corticosteroids, will become the mainstay of asthma treatment (Barnes, *Nature Reviews*, 2004, 3, 831-844). The advantages of once-daily bronchodilator treatment in COPD has been demonstrated with tiotropium, a non-selective muscarinic antagonist (Koumis and Samuel, *Clin. Ther.* 2005, 27(4), 377-92). There is, however, a need for a once-daily LABA for the treatment of COPD to avoid the side effects of anti-muscarinics such as tiotropium.

Benzothiazolone derivatives having dual β2 receptor and dopamine (D2) receptor agonist properties are known from WO 92/08708, WO 93/23385 and WO 97/10227.

In accordance with the present invention, there is therefore provided a compound of formula (I):

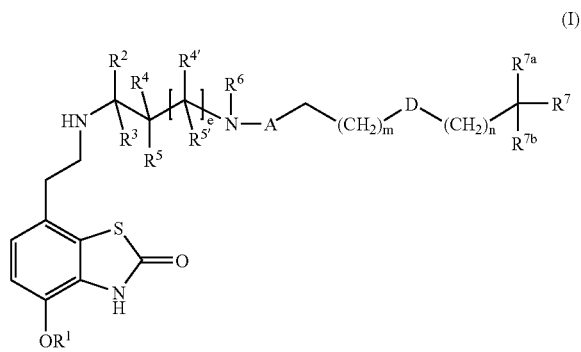

wherein
$R^1$ represents hydrogen;
each of $R^2$, $R^3$, $R^4$, $R^5$, $R^{4'}$ and $R^{5'}$ independently represents hydrogen or $C_1$-$C_6$ alkyl;
e is 0 or 1;
A represents $CH_2$, $C(O)$ or $S(O)_2$;
D represents oxygen, sulphur or $NR^8$;
m is an integer from 0 to 3;
n is an integer from 0 to 3;
$R^6$ represents a group $-(X)_p-Y-(Z)_q-R^{10}$;
X and Z each independently represent a $C_1$-$C_6$ alkylene group optionally substituted by halogen, trifluoromethyl, amino ($NH_2$), (di)-$C_1$-$C_6$ alkylamino, (di)-$C_1$-$C_6$ alkylaminocarbonyl, $C_1$-$C_6$ alkylcarbonylamino, sulphonamido ($-SO_2NH_2$) or (di)-$C_1$-$C_6$ alkylaminosulphonyl;
p and q each independently represent 0 or 1;
Y represents a bond, oxygen, sulphur, $CH_2$, $C(O)$ or $NR^9$; provided that when p is 0 Y is not sulphur;
$R^{7a}$ and $R^{7b}$ are, independently, hydrogen or $C_1$-$C_6$ alkyl;
$R^8$ represents hydrogen or $C_1$-$C_6$ alkyl;
$R^9$ represents hydrogen or $C_1$-$C_6$ alkyl;
$R^{10}$ represents hydrogen, or a saturated or unsaturated 3- to 10-membered ring system optionally comprising at least one ring heteroatom selected from nitrogen, oxygen and sulphur, the ring system being optionally substituted by halogen, trifluoromethyl, cyano, carboxyl, hydroxyl, nitro, $-S(O)_rR^{15}$, $-NR^{16}S(O)_2R^{17}$, $-C(O)NR^{18}R^{19}$, $-NHC(O)R^{20}$, $C_1$-$C_6$ alkyl, $C_1$-$C_6$ alkoxy, $C_1$-$C_6$ alkylcarbonyl, $C_1$-$C_6$ alkoxycarbonyl or a saturated or unsaturated 4- to 7-membered monocyclic ring system optionally comprising at least one ring heteroatom selected from nitrogen, oxygen and sulphur, the monocyclic ring system itself being optionally substituted by halogen, trifluoromethyl, hydroxyl, $-NR^{21}S(O)_2R^{22}$, $-NHC(O)R^{23}$ or $C_1$-$C_6$ alkoxy;
$R^{16}$, $R^{17}$, $R^{18}$, $R^{19}$, $R^{20}$, $R^{21}$ and $R^{23}$ each independently represent hydrogen or $C_1$-$C_6$ alkyl;
$R^{15}$, $R^{17}$ and $R^{22}$ each independently represent $C_1$-$C_6$ alkyl;
r is 0, 1 or 2;

R⁷ represents a 5- to 14-membered aromatic or heteroaromatic ring system which is optionally substituted by halogen, trifluoromethyl, hydroxyl, carboxyl, $C_1$-$C_6$ alkyl (optionally substituted by —NR²⁴R²⁵), $C_1$-$C_6$ alkoxy (optionally substituted by —NR²⁶R²⁷), $C_1$-$C_6$ alkoxycarbonyl, —NR²⁸R²⁹, $C_1$-$C_6$ alkylcarbonylamino, $C_1$-$C_6$ alkylsulphonylamino, phenylsulphonylamino, —C(O)NHR³⁰, —SO₂NHR³³, $C_0$-$C_6$ alkyl-R³⁴, or a phenyl or 5- or 6-membered heteroaromatic ring (each of which is optionally substituted by halogen, trifluoromethyl, hydroxyl, $C_1$-$C_6$ alkyl, $C_1$-$C_6$ alkoxy or —NR³⁵R³⁶);

R²⁴, R²⁵, R²⁶, R²⁷, R²⁸ and R²⁹ each independently represent hydrogen or $C_1$-$C_6$ alkyl;

R³⁰ represents hydrogen, $C_1$-$C_6$ alkyl, phenyl-$C_0$-$C_6$ alkyl or $C_2$-$C_6$ alkylene-NR³¹R³²;

either R³¹ and R³² each independently represent hydrogen or $C_1$-$C_6$ alkyl, or R³¹ and R³² together with the nitrogen atom to which they are attached form a 4- to 6-membered saturated heterocyclic ring optionally comprising a further ring heteroatom selected from nitrogen and oxygen;

R³³ represents hydrogen, $C_1$-$C_6$ alkyl, phenyl-$C_0$-$C_6$ alkyl or $C_2$-$C_6$ alkylene-NR³⁷R³⁸;

R³⁴ represents a saturated, 5- or 6-membered nitrogen-containing ring;

R³⁵ and R³⁶ each independently represent hydrogen or $C_1$-$C_6$ alkyl; and either R³⁷ and R³⁸ each independently represent hydrogen or $C_1$-$C_6$ alkyl, or R³⁷ and R³⁸ together with the nitrogen atom to which they are attached form a 4- to 6-membered saturated heterocyclic ring optionally comprising a further ring heteroatom selected from nitrogen and oxygen;

with the proviso that R⁶ does not represent hydrogen or an unsubstituted $C_1$-$C_6$ alkyl group; or a pharmaceutically acceptable salt thereof.

In the context of the present specification, unless otherwise stated, an alkyl substituent group or an alkyl moiety in a substituent group may be linear or branched. Examples of $C_1$-$C_6$ alkyl groups/moieties include methyl, ethyl, n-propyl, isopropyl, n-butyl, isobutyl, tert-butyl, n-pentyl and n-hexyl. Similarly, an alkylene group may be linear or branched. Examples of $C_1$-$C_6$ alkylene groups include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene. The alkyl moieties in a di-$C_1$-$C_6$ alkylamino, di-$C_1$-$C_6$ alkylaminocarbonyl or di-$C_1$-$C_6$ alkylaminosulphonyl substituent group may be the same or different. In the definition of R¹⁰, the saturated or unsaturated 3- to 10-membered ring system and the saturated or unsaturated 4- to 7-membered monocyclic ring system may each have alicyclic or aromatic properties. An unsaturated ring system will be partially or fully unsaturated. When R³¹ and R³² (or R³⁷ and R³⁸) together represent a 4- to 6-membered saturated heterocyclic ring, it should be understood that the ring will contain no more than two ring heteroatoms: the nitrogen ring atom to which R³¹ and R³² (or R³⁷ and R³⁸) are attached and optionally a nitrogen or oxygen ring atom.

The compounds of the invention are selective β2 receptor agonists and possess properties that make them more suitable for once-a-day administration. Compounds have been optimised to have appropriate duration in an in vitro guinea pig trachea model, or mammalian model such as a histamine-challenged guinea pig. The compounds also have advantageous pharmokinetic half lives in mammalian systems. In particular, the compounds of the invention are at least 10-fold more potent at the β2 receptor compared to the α1, β1, or dopamine (D2) receptors. The compounds are also notable for having a fast is onset of action that is the time interval between administration of a compound of the invention to a patient and the compound providing symptomatic relief. Onset can be predicted in vitro using isolated trachea from guinea pig or human.

In one particular aspect the present invention provides a compound of formula (I) wherein R¹ represents hydrogen;

each of R², R³, R⁴, R⁵, R⁴' and R⁵' independently represents hydrogen or $C_1$-$C_6$ alkyl;

e is 0 or 1;

A represents CH₂, C(O) or S(O)₂;

D represents oxygen, sulphur or NR⁸;

m is an integer from 0 to 3;

n is an integer from 0 to 3;

R⁶ represents a group —(X)$_p$—Y-(Z)$_q$-R¹⁰;

X and Z each independently represent a $C_1$-$C_6$ alkylene group optionally substituted with at least one substituent selected from halogen, trifluoromethyl, amino (NH₂), (di)-$C_1$-$C_6$ alkylamino, (di)-$C_1$-$C_6$ alkylaminocarbonyl, $C_1$-$C_6$ alkylcarbonylamino, sulphonamido (—SO₂NH₂) and (di)-$C_1$-$C_6$ alkylaminosulphonyl;

p and q each independently represent 0 or 1;

Y represents a bond, oxygen, sulphur, CH₂, C(O) or NR⁹;

R⁷ᵃ and R⁷ᵇ are both hydrogen;

R⁸ represents hydrogen or $C_1$-$C_6$ alkyl;

R⁹ represents hydrogen or $C_1$-$C_6$ alkyl;

R¹⁰ represents hydrogen, or a saturated or unsaturated 3- to 10-membered ring system optionally comprising at least one ring heteroatom selected from nitrogen, oxygen and sulphur, the ring system being optionally substituted by one or more substituents independently selected from halogen, trifluoromethyl, cyano, carboxyl, hydroxyl, nitro, —S(O)$_r$R¹⁵, —NR¹⁶S(O)$_s$R¹⁷, —C(O)NR¹⁸R¹⁹, —NHC(O)R²⁰, $C_1$-$C_6$ alkyl, $C_1$-$C_6$ alkoxy, $C_1$-$C_6$ alkylcarbonyl, $C_1$-$C_6$ alkoxycarbonyl and a saturated or unsaturated 4- to 7-membered monocyclic ring system optionally comprising at least one ring heteroatom selected from nitrogen, oxygen and sulphur, the monocyclic ring system itself being optionally substituted by at least one substituent selected from halogen, trifluoromethyl, hydroxyl, —NR²¹S(O)$_t$R²², —NHC(O)R²³ and $C_1$-$C_6$ alkoxy;

R¹⁵, R¹⁶R¹⁷, R¹⁸, R¹⁹, R²⁰, R²¹, R²² and R²³ each independently represent hydrogen or $C_1$-$C_6$ alkyl;

r, s and t each independently represent 0, 1 or 2;

R⁷ represents a 6- to 14-membered aromatic or heteroaromatic ring system optionally substituted by one or more substituents independently selected from halogen, trifluoromethyl, hydroxyl, carboxyl, $C_1$-$C_6$ alkyl (optionally substituted by at least one —NR²⁴R²⁵), $C_1$-$C_6$ alkoxy (optionally substituted by at least one —NR²⁶R²⁷), $C_1$-$C_6$ alkoxycarbonyl, —NR²⁸R²⁹, $C_1$-$C_6$ alkylcarbonylamino, $C_1$-$C_6$ alkylsulphonylamino, phenylsulphonylamino, —C(O)NHR³⁰, —SO₂NHR³³, $C_0$-$C_6$ alkyl-R³⁴, and a phenyl or 5- to 6-membered heteroaromatic ring (each of which may be optionally substituted by one or more substituents independently selected from halogen, trifluoromethyl, hydroxyl, $C_1$-$C_6$ alkyl, $C_1$-$C_6$ alkoxy and —NR³⁵R³⁶);

R²⁴, R²⁵, R²⁶, R²⁷, R²⁸ and R²⁹ each independently represent hydrogen or $C_1$-$C_6$ alkyl;

$R^{30}$ represents hydrogen, $C_1$-$C_6$ alkyl, phenyl-$C_0$-$C_6$ alkyl or $C_2$-$C_6$ alkylene-$NR^{31}R^{32}$;

either $R^{31}$ and $R^{32}$ each independently represent hydrogen or $C_1$-$C_6$ alkyl, or $R^{31}$ and $R^{32}$ together with the nitrogen atom to which they are attached form a 4- to 6-membered saturated heterocyclic ring optionally comprising a further ring heteroatom selected from nitrogen and oxygen;

$R^{33}$ represents hydrogen, $C_1$-$C_6$ allyl, phenyl-$C_0$-$C_6$ alkyl or $C_2$-$C_6$ alkylene-$NR^{37}R^{38}$;

$R^{34}$ represents a saturated, 5- or 6-membered nitrogen-containing ring;

$R^{35}$ and $R^{36}$ each independently represent hydrogen or $C_1$-$C_6$ alkyl; and either $R^{37}$ and $R^{38}$ each independently represent hydrogen or $C_1$-$C_6$ alkyl, or $R^{37}$ and $R^{38}$ together with the nitrogen atom to which they are attached form a 4- to 6-membered saturated heterocyclic ring optionally comprising a further ring heteroatom selected from nitrogen and oxygen;

with the proviso that $R^6$ does not represent hydrogen or an unsubstituted $C_1$-$C_6$ alkyl group; or a pharmaceutically acceptable salt thereof.

In another aspect the present invention provides a compound of formula (I) wherein
$R^1$ represents hydrogen;
each of $R^2$, $R^3$, $R^4$, $R^5$, $R^{4'}$ and $R^{5'}$ independently represents hydrogen or $C_1$-$C_6$ alkyl;
e is 0 or 1;
A represents $CH_2$, C(O) or $S(O)_2$;
D represents oxygen, sulphur or $NR^8$;
m is an integer from 0 to 3;
n is an integer from 0 to 3;
$R^6$ represents a group —$(X)_p$—Y-$(Z)_q$-$R^{10}$;
X and Z each independently represent a $C_1$-$C_6$ alkylene group optionally substituted with at least one substituent selected from halogen, trifluoromethyl, amino ($NH_2$), (di)-$C_1$-$C_6$ alkylamino, (di)-$C_1$-$C_6$ alkylaminocarbonyl, $C_1$-$C_6$ alkylcarbonylamino, sulphonamido (—$SO_2NH_2$) and (di)-$C_1$-$C_6$ alkylaminosulphonyl;
p and q each independently represent 0 or 1;
Y represents a bond, oxygen, sulphur, $CH_2$, C(O) or $NR^9$;
$R^{7a}$ and $R^{7b}$ are both hydrogen;
$R^8$ represents hydrogen or $C_1$-$C_6$ alkyl;
$R^9$ represents hydrogen or $C_1$-$C_6$ alkyl;
$R^{10}$ represents hydrogen, or a saturated or unsaturated 3- to 10-membered ring system optionally comprising at least one ring heteroatom selected from nitrogen, oxygen and sulphur, the ring system being optionally substituted by one or more substituents independently selected from halogen, trifluoromethyl, cyano, carboxyl, hydroxyl, nitro, —$S(O)_rR^{15}$, —$NR^{16}S(O)_sR^{17}$, —$C(O)NR^{18}R^{19}$, —$NHC(O)R^{20}$, $C_1$-$C_6$ alkyl, $C_1$-$C_6$ alkoxy, $C_1$-$C_6$ alkylcarbonyl, $C_1$-$C_6$ alkoxycarbonyl and a saturated or unsaturated 4- to 7-membered monocyclic ring system optionally comprising at least one ring heteroatom selected from nitrogen, oxygen and sulphur, the monocyclic ring system itself being optionally substituted by at least one substituent selected from halogen, trifluoromethyl, hydroxyl, —$NR^{21}S(O)_tR^{22}$, —$NHC(O)R^{23}$ and $C_1$-$C_6$ alkoxy;
$R^{15}$, $R^{16}$, $R^{17}$, $R^{19}$, $R^{20}$, $R^{21}$, $R^{22}$ and $R^{23}$ each independently represent hydrogen or $C_1$-$C_6$ alkyl;
r, s and t each independently represent 0, 1 or 2;
$R^7$ represents a 6- to 14-membered aromatic or heteroaromatic ring system optionally substituted by one or more substituents independently selected from halogen, trifluoromethyl, hydroxyl, carboxyl, $C_1$-$C_6$ alkyl (optionally substituted by at least one —$NR^{24}R^{25}$), $C_1$-$C_6$ alkoxy (optionally substituted by at least one —$NR^{26}R^{27}$), $C_1$-$C_6$ alkoxycarbonyl, —$NR^{28}R^{29}$, $C_1$-$C_6$ alkylcarbonylamino, $C_1$-$C_6$ alkylsulphonylamino, phenylsulphonylamino, —$C(O)NHR^{30}$, —$SO_2NHR^{33}$ and $C_0$-$C_6$ alkyl-$R^{34}$;
$R^{24}$, $R^{25}$, $R^{26}$, $R^{27}$, $R^{28}$ and $R^{29}$ each independently represent hydrogen or $C_1$-$C_6$ alkyl;
$R^{30}$ represents $C_1$-$C_6$ alkylene-$NR^{31}R^{32}$;
either $R^{31}$ and $R^{32}$ each independently represent hydrogen or $C_1$-$C_6$ alkyl, or $R^{31}$ and $R^{32}$ together with the nitrogen atom to which they are attached form a 4- to 6-membered saturated heterocyclic ring optionally comprising a further ring heteroatom selected from nitrogen and oxygen;
$R^{33}$ represents hydrogen, $C_1$-$C_6$ alkyl or phenyl; and
$R^{34}$ represents a saturated, 5- or 6-membered nitrogen-containing ring; with the proviso that $R^6$ does not represent hydrogen or an unsubstituted $C_1$-$C_6$ alkyl group; or a pharmaceutically acceptable salt thereof.

In an embodiment of the invention, each of $R^2$, $R^3$, $R^4$, $R^5$ and, if present, $R^{4'}$ and $R^{5'}$ independently represents hydrogen or $C_1$-$C_6$, or $C_1$-$C_4$, or $C_1$-$C_2$ alkyl.

In a further embodiment of the invention $R^2$ and $R^3$ are both hydrogen and $R^4$ and $R^5$ and, if present, $R^{4'}$ and $R^{5'}$ are, independently hydrogen or $C_1$-$C_6$ alkyl.

In another embodiment, each of $R^2$, $R^3$, $R^4$, $R^5$ and, if present, $R^{4'}$ and $R^{5'}$ represents hydrogen.

In yet another embodiment e is 0.

In an embodiment of the invention, A represents C(O).

In another embodiment of the invention, A represents $CH_2$.

In an embodiment of the invention, D represents oxygen.

In an embodiment of the invention, m is an integer 0, 1, 2 or 3, for example, 1.

In an embodiment of the invention, n is an integer 0, 1, 2 or 3, for example, 1.

In a further aspect the present invention provides a compound of formula (I) wherein X and Z each independently represent a $C_1$-$C_6$, or $C_1$-$C_4$, or $C_1$-$C_2$ alkylene group optionally substituted with at least one substituent (e.g. one, two or three substituents independently) selected from halogen (e.g. fluorine, chlorine, bromine or iodine), trifluoromethyl, amino, (di)-$C_1$-$C_6$, or $C_1$-$C_4$, or $C_1$-$C_2$ alkylamino (e.g. methylamino, ethylamino, dimethylamino or diethylamino), (di)-$C_1$-$C_6$, or $C_1$-$C_4$, or $C_1$-$C_2$ alkylaminocarbonyl (e.g. methylaminocarbonyl, ethylaminocarbonyl, dimethylaminocarbonyl or diethylaminocarbonyl), $C_1$-$C_6$, or $C_1$-$C_4$, or $C_1$-$C_2$ alkylcarbonylamino (e.g. methylcarbonylamino or ethylcarbonylamino), sulphonamido and (di)-$C_1$-$C_6$, or $C_1$-$C_4$, or $C_1$-$C_2$ alkylaminosulphonyl (e.g. methylaminosulphonyl, ethylaminosulphonyl, dimethylaminsulphonyl or diethylaminsulphonyl).

In a still further aspect the present invention provides a compound of formula (I) wherein $R^6$ is —X—Y—$R^{10}$.

In a still further aspect the present invention provides a compound of formula (I) wherein $R^6$ is —X—Y-Z-$R^{10}$.

In one embodiment, X represents a $C_1$-$C_5$ alkylene group.

In another embodiment, Z represents a $C_1$-$C_2$ alkylene group.

In an embodiment of the invention, p is 0 and q is 1.

In another embodiment, p is 1 and q is 0.

In still another embodiment, p and q are either both 0 or 1.

In an embodiment of the invention, Y represents a bond, oxygen, $CH_2$ or $NR^9$. In a further aspect of the invention Y is $NR^9$.

In another aspect the present invention provides a compound of formula (I) wherein $R^{7a}$, and $R^{7b}$ are, independently, hydrogen, methyl or ethyl; for example $R^{7a}$ and $R^{7b}$ are both hydrogen.

In a further aspect the present invention provides a compound of formula (I) wherein $R^8$ represents hydrogen or $C_1$-$C_6$, or $C_1$-$C_4$, or $C_1$-$C_2$ alkyl.

In a still further aspect the present invention provides a compound of formula (I) wherein $R^9$ represents hydrogen or $C_1$-$C_6$, or $C_1$-$C_4$, or $C_1$-$C_2$ alkyl.

In a further aspect the present invention provides a compound of formula (I) wherein $R^9$ is $C_1$-$C_4$ alkyl (for example methyl or ethyl).

In another aspect the present invention provides a compound of formula (I) wherein $R^{10}$ represents hydrogen, or a saturated or unsaturated 3- to 10-membered (e.g. 3-, 4-, 5-, 6-, 7-, 8-, 9- or 10-membered) ring system optionally comprising a ring heteroatom (e.g. none, one, two, three or four ring heteroatoms independently) which, when present, is selected from nitrogen, oxygen and sulphur, the ring system being unsubstituted or substituted by one or more (e.g. one, two, three or four) substituents independently selected from halogen (e.g. fluorine, chlorine, bromine or iodine), trifluoromethyl, cyano, carboxyl, hydroxyl, nitro, —S(O)$_r$R$^{15}$, —NR$^{16}$S(O)$_2$R$^{17}$, —C(O)NR$^{15}$R$^{19}$, —NHC(O)R$^{20}$, $C_1$-$C_6$, or $C_1$-$C_4$, or $C_1$-$C_2$ alkyl, $C_1$-$C_6$, or $C_1$-$C_4$, or $C_1$-$C_2$ alkoxy, $C_1$-$C_6$, or $C_1$-$C_4$, or $C_1$-$C_2$ alkylcarbonyl, $C_1$-$C_6$, or $C_1$-$C_4$, or $C_1$-$C_2$ alkoxycarbonyl and a saturated or unsaturated 4-, 5-, 6- or 7-membered monocyclic ring system optionally comprising a ring heteroatom (e.g. none, one, two, three or four ring heteroatoms independently) which, when present, is selected from nitrogen, oxygen and sulphur, the monocyclic ring system itself being unsubstituted is or substituted by at least one substituent (e.g. one, two, three or four substituents independently) selected from halogen (e.g. fluorine, chlorine, bromine or iodine), trifluoromethyl, hydroxyl, —NR$^{21}$S(O)$_2$R$^{22}$, —NHC(O)R$^{23}$ and $C_1$-$C_6$, or $C_1$-$C_4$, or $C_1$-$C_2$ alkoxy.

Examples of saturated or unsaturated 3- to 10-membered ring systems include monocyclic rings or polycyclic (e.g. bicyclic) ring systems in which two or more rings are fused. Examples include one, or a combination of two or more, of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, diazabicyclo[2.2.1]hept-2-yl, naphthyl, benzofuranyl, benzothienyl, benzodioxolyl, quinolinyl, oxazolyl, 2,3-dihydrobenzofuranyl, tetrahydropyranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl. In another aspect of the invention a saturated or unsaturated 3- to 10-membered ring system is piperidinyl, pyridinyl or phenyl.

Examples of saturated or unsaturated 4- to 7-membered monocyclic ring systems include cyclobutyl, cyclopentyl, cyclohexyl, pyrrolidinyl, piperazinyl, morpholinyl, furanyl, thienyl, pyrrolyl, phenyl, oxazolyl, 1,2,4-oxadiazolyl, 1,3,4-oxadiazolyl, isoxazolyl, imidazolyl, pyrazolyl, thiazolyl, triazolyl, thiadiazolyl, pyridinyl, pyrimidinyl, pyrazinyl and tetrazolyl.

In an embodiment of the invention, $R^{10}$ represents hydrogen, or a saturated or unsaturated 5- or 6-membered ring system optionally comprising one or more ring heteroatoms (e.g. none or one or two ring heteroatoms) which, when present, are independently selected from nitrogen and oxygen, the ring system being unsubstituted or substituted by one or more (e.g. one, two, three or four) substituents independently selected from halogen (e.g. fluorine, chlorine, bromine or iodine), trifluoromethyl, cyano, carboxyl, hydroxyl, nitro, —S(O)$_r$R$^{15}$, —NR$^{16}$S(O)$_2$R$^{17}$, —C(O)NR$^{18}$R$^{19}$, —NHC(O)R$^{20}$, $C_1$-$C_6$, or $C_1$-$C_4$, or $C_1$-$C_2$ alkyl, $C_1$-$C_6$, or $C_1$-$C_4$, or $C_1$-$C_2$ alkoxy, $C_1$-$C_6$, or $C_1$-$C_4$, or $C_1$-$C_2$ alkylcarbonyl, $C_1$-$C_6$, or $C_1$-$C_4$, or $C_1$-$C_2$ alkoxycarbonyl and a saturated or unsaturated 4-, 5-, 6- or 7-membered monocyclic ring system optionally comprising one or more one ring heteroatom (e.g. none, one, two, three or four ring heteroatoms) which, when present, are independently selected from nitrogen, oxygen and sulphur, the monocyclic ring system itself being unsubstituted or substituted by one or more substituents (e.g. one, two, three or four substituents) independently selected from halogen (e.g. fluorine, chlorine, bromine or iodine), trifluoromethyl, hydroxyl, —NR$^{21}$S(O)$_2$R$^{22}$, —NHC(O)R$^{23}$ and $C_1$-$C_6$, or $C_1$-$C_4$, or $C_1$-$C_2$ alkoxy.

In another embodiment, $R^{10}$ represents hydrogen, or a saturated or unsaturated 5- or 6-membered ring system optionally comprising one or more ring heteroatom (e.g. none, one or two ring heteroatoms independently) which, when present, are independently selected from nitrogen and oxygen, the ring system being unsubstituted or substituted by one or two substituents independently selected from halogen (e.g. fluorine, chlorine, bromine or iodine), trifluoromethyl, cyano, carboxyl, hydroxyl, nitro, —S(O)$_r$R$^{15}$, —NR$^{16}$S(O)$_2$R$^{17}$, —C(O)NR$^{18}$R$^{19}$, —NHC(O)R$^{20}$, $C_1$-$C_4$ or $C_1$-$C_2$ alkyl, $C_1$-$C_4$ or $C_1$-$C_2$ alkoxy, $C_1$-$C_4$ or $C_1$-$C_2$ alkylcarbonyl, $C_1$-$C_4$ or $C_1$-$C_2$ alkoxycarbonyl and a saturated or unsaturated 5- or 6-membered monocyclic ring system optionally comprising one or more ring heteroatoms (e.g. one or two ring heteroatoms) which, when present, are independently selected from nitrogen, oxygen and sulphur, the monocyclic ring system itself being unsubstituted or substituted by one or more substituents (e.g. one or two substituents independently) selected from halogen (e.g. fluorine, chlorine, bromine or iodine), trifluoromethyl, hydroxyl, —NR$^{21}$S(O)$_2$R$^{22}$, —NHC(O)R$^{23}$ and $C_1$-$C_4$ or $C_1$-$C_2$ alkoxy.

In a further embodiment, $R^{10}$ represents hydrogen, or a saturated or unsaturated 5- or 6-membered ring system comprising none, one or two ring heteroatoms which, when present, are independently selected from nitrogen and oxygen, the ring system being unsubstituted or substituted by one or two substituents independently selected from halogen (e.g. fluorine, chlorine, bromine or iodine), trifluoromethyl, carboxyl, hydroxyl, —S(O)$_r$R$^{15}$, —NR$^{16}$S(O)$_2$R$^{17}$, —C(O)NR$^{18}$R$^{19}$, —NHC(O)R$^{20}$, $C_1$-$C_4$ or $C_1$-$C_2$ alkyl, $C_1$-$C_4$ or $C_1$-$C_2$ alkoxy, $C_1$-$C_4$ or $C_1$-$C_2$ alkylcarbonyl and $C_1$-$C_4$ or $C_1$-$C_2$ alkoxycarbonyl.

In a still further embodiment, $R^{10}$ represents hydrogen, or a saturated or unsaturated 5- or 6-membered ring system comprising none, one or two ring heteroatoms which, when present, are independently selected from nitrogen and oxygen, the ring system being unsubstituted or substituted by one or two substituents independently selected from $C_1$-$C_4$ or $C_1$-$C_2$ alkoxycarbonyl.

In yet another embodiment, $R^{10}$ represents hydrogen, phenyl, pyridinyl or piperidinyl ring optionally substituted by $C_4$ alkoxycarbonyl.

In a further embodiment, $R^{10}$ is hydrogen.

In a still further embodiment $R^{10}$ is phenyl, pyridinyl, or a piperidinyl group optionally substituted by $C_1$-$C_4$ alkoxycarbonyl.

In yet another aspect of the invention $R^6$ is $(CH_2)_q R^{10a}$, wherein q is 0, 1, 2 or 3 (for example 2); $R^{10a}$ is phenyl, pyridyl, NR$^{9a}$R$^{9b}$ or piperidinyl (optionally N-substituted by C(O)O($C_{1-6}$ alkyl)); and $R^{9a}$ and $R^{9b}$ are, independently, $C_{1-4}$ alkyl (for example methyl or ethyl).

In a further embodiment of the invention $R^{15}$, $R^{16}$, $R^{17}$, $R^{18}$, $R^{19}$, $R^{20}$, $R^{21}$, $R^{22}$ and $R^{23}$ each independently represent hydrogen or $C_1$-$C_6$, or $C_1$-$C_4$, or $C_1$-$C_2$ alkyl.

In a still further embodiment of the invention $R^{15}$, $R^{16}$, $R^{17}$, $R^{18}$, $R^{19}$, $R^{20}$, $R^{21}R^{22}$ and $R^{23}$ each independently represent $C_1$-$C_6$, or $C_1$-$C_4$, or $C_1$-$C_2$ alkyl; and $R^{16}$, $R^{18}$, $R^{19}$, $R^{20}$, $R^{21}$ and $R^{23}$ can also be hydrogen.

In another embodiment of the invention $R^{16}$, $R^{18}$, $R^{19}$, $R^{20}$, $R^{21}$ and $R^{23}$ each independently represent hydrogen or $C_1$-$C_6$, or $C_1$-$C_4$, or $C_1$-$C_2$ alkyl.

In yet another embodiment $R^{15}$, $R^{17}$ and $R^{22}$ are, independently, $C_1$-$C_6$, or $C_1$-$C_4$, or $C_1$-$C_2$ alkyl.

In a further embodiment of the invention $R^7$ represents a 5- to 14-membered (5-, 6-, 7-, 8-, 9-, 10-, 11-, 12-, 13- or 14-membered) aromatic or heteroaromatic ring system optionally substituted by none, one or more (e.g. none, one, two, three or four) substituents independently selected from halogen (e.g. fluorine, chlorine, bromine or iodine), trifluoromethyl, hydroxyl, carboxyl, $C_1$-$C_6$, or $C_1$-$C_4$, or $C_1$-$C_2$ alkyl (optionally substituted by none, one or more, e.g. none, one or two, —$NR^{24}R^{25}$), $C_1$-$C_6$, or $C_1$-$C_4$, or $C_1$-$C_2$ alkoxy (optionally substituted by none, one or more, e.g. none, one or two, —$NR^{26}R^{27}$), $C_1$-$C_6$, or $C_1$-$C_4$, or $C_1$-$C_2$ alkoxycarbonyl, —$NR^{28}R^{29}$, $C_1$-$C_6$, or $C_1$-$C_4$, or $C_1$-$C_2$ alkylcarbonylamino, $C_1$-$C_6$, or $C_1$-$C_4$, or $C_1$-$C_2$ alkylsulphonylamino, phenylsulphonylamino, —$C(O)NHR^{30}$, —$SO_2NHR^{33}$, $C_0$-$C_6$, or $C_0$-$C_4$, or $C_0$-$C_2$ alkyl-$R^{34}$, and phenyl or 5- or 6-membered heteroaromatic ring (each of which is unsubstituted or substituted by one or more, e.g. one, two, three or four, substituents independently selected from halogen such as fluorine, chlorine, bromine or iodine, trifluoromethyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ alkoxy and —$NR^{35}R^{36}$).

In another embodiment of the invention $R^7$ represents a 6- to 14-membered (6-, 7-, 8-, 9-, 10-, 11-, 12-, 13- or 14-membered) aromatic or heteroaromatic ring system optionally substituted by one or more (e.g. one, two, three or four) substituents independently selected from halogen (e.g. fluorine, chlorine, bromine or iodine), trifluoromethyl, hydroxyl, carboxyl, $C_1$-$C_6$, or $C_1$-$C_4$, or $C_1$-$C_2$ allyl (optionally substituted by at least one, e.g. one or two, —$NR^{24}R^{25}$), $C_1$-$C_6$, or $C_1$-$C_4$, or $C_1$-$C_2$ alkoxy (optionally substituted by at least one, e.g. one or two, —$NR^{26}R^{27}$), $C_1$-$C_6$, or $C_1$-$C_4$, or $C_1$-$C_2$ alkoxycarbonyl, —$NR^{28}R^{29}$, $C_1$-$C_6$, or $C_1$-$C_4$, or $C_1$-$C_2$ alkylcarbonylamino, $C_1$-$C_6$, or $C_1$-$C_4$, or $C_1$-$C_2$ alkylsulphonylamino, phenylsulphonylamino, —$C(O)NHR^{30}$, —$SO_2NHR^{33}$, $C_0$-$C_6$, or $C_0$-$C_4$, or $C_1$-$C_2$ alkyl-$R^{34}$, and phenyl or 5- to 6-membered heteroaromatic ring (each of which may be optionally substituted by one or more, e.g. one, two, three or four, substituents independently selected from halogen such as fluorine, chlorine, bromine or iodine, trifluoromethyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ alkoxy and —$NR^{35}R^{36}$).

In a further embodiment of the invention $R^7$ represents a 6- to 14-membered (6-, 7-, 8-, 9-, 10-, 11-, 12-, 13- or 14-membered) aromatic or heteroaromatic ring system optionally substituted by one or more (e.g. one, two, three or four) substituents independently selected from halogen (e.g. fluorine, chlorine, bromine or iodine), trifluoromethyl, hydroxyl, carboxyl, $C_1$-$C_6$, or $C_1$-$C_4$, or $C_1$-$C_2$ alkyl (optionally substituted by at least one, e.g. one or two, —$NR^{24}R^{25}$), $C_1$-$C_6$, or $C_1$-$C_4$, or $C_1$-$C_2$ alkoxy (optionally substituted by at least one, e.g. one or two, —$NR^{26}R^{27}$), $C_1$-$C_6$, or $C_1$-$C_4$, or $C_1$-$C_2$ alkoxycarbonyl, —$NR^{28}R^{29}$, $C_1$-$C_6$, or $C_1$-$C_4$, or $C_1$-$C_2$ alkylcarbonylamino, $C_1$-$C_6$, or $C_1$-$C_4$, or $C_1$-$C_2$ alkylsulphonylamino, phenylsulphonylamino, —$C(O)NHR^{30}$, —$SO_2NHR^{33}$ and $C_0$-$C_6$, or $C_0$-$C_4$, or $C_0$-$C_2$ alkyl-$R^{34}$.

When $R^7$ represents an optionally substituted 5- to 14-membered heteroaromatic ring system, the ring system comprises from 1 to 4 ring heteroatoms independently selected from nitrogen, oxygen and sulphur. Similarly, if a substituent in $R^7$ represents an optionally substituted 5- to 6-membered heteroaromatic ring, the ring comprises from 1 to 4 ring heteroatoms independently selected from nitrogen, oxygen and sulphur.

When $R^7$ represents an optionally substituted 6- to 14-membered heteroaromatic ring system, the ring system comprises from 1 to 4 ring heteroatoms independently selected from nitrogen, oxygen and sulphur. Similarly, if a substituent in $R^7$ represents an optionally substituted 5- to 6-membered heteroaromatic ring, the ring comprises from 1 to 4 ring heteroatoms independently selected from nitrogen, oxygen and sulphur.

When $R^7$ represents an optionally substituted heteroaromatic ring system, the ring system comprises from 1 to 4 ring heteroatoms independently selected from nitrogen, oxygen and sulphur.

Examples of 5- to 14-membered (6- to 14-membered) aromatic or heteroaromatic ring systems that may be used, which may be monocyclic or polycyclic (e.g. bicyclic or tricyclic) in which the two or more rings are fused, include one or more (in any combination) of phenyl, naphthyl, pyridinyl, pyridazinyl, pyrimidinyl, pyrazinyl, 1,3,5-triazinyl, 1,2,4-triazinyl, azepinyl, oxepinyl, thiepinyl, indenyl, benzofuranyl, isobenzofuranyl, benzothiophenyl, indolyl, isoindolyl, benzimidazolyl, indazolyl, benzisoxazolyl, benzoxazolyl, benzothiazolyl, quinolinyl, isoquinolinyl, quinazolinyl, quinoxalinyl and dibenzofuranyl. Preferred ring systems include phenyl and naphthyl.

Examples of 5- to 6-membered heteroaromatic rings include pyridinyl, triazolyl and tetrazolyl.

In an embodiment of the invention, $R^7$ represents a 5- to 10-membered (for example 6- to 10-membered) aromatic or heteroaromatic ring system optionally substituted by none, one or more (e.g. none, one or two) substituents independently selected from halogen (e.g. fluorine, chlorine, bromine or iodine), trifluoromethyl, hydroxyl, carboxyl, $C_1$-$C_4$, or $C_1$-$C_2$ alkyl (optionally substituted by (e.g. none, one or two)-$NR^{24}R^{25}$), $C_1$-$C_4$, or $C_1$-$C_2$ alkoxy (optionally substituted by (e.g. none, one or two)-$NR^{26}R^{27}$), $C_1$-$C_4$, or $C_1$-$C_2$ alkoxycarbonyl, —$NR^{28}R^{29}$, $C_1$-$C_4$, or $C_1$-$C_2$ alkylcarbonylamino, $C_1$-$C_4$, or $C_1$-$C_2$ alkylsulphonylamino, phenylsulphonylamino, —$C(O)NHR^{30}$, —$SO_2NHR^{33}$, $C_0$-$C_4$ or $C_0$-$C_2$ alkyl-$R^{34}$, phenyl and a 5- to 6-membered heteroaromatic ring.

In an embodiment of the invention, $R^7$ represents a 6- to 10-membered aromatic or heteroaromatic ring system optionally substituted by none, one or more (e.g. none, one or two) substituents independently selected from halogen (e.g. fluorine, chlorine, bromine or iodine), trifluoromethyl, hydroxyl, carboxyl, $C_1$-$C_4$, or $C_1$-$C_2$ alkyl (optionally substituted by (e.g. none, one or two)-$NR^{24}R^{25}$), $C_1$-$C_4$, or $C_1$-$C_2$ alkoxy (optionally substituted by (e.g. none, one or two)-$NR^{26}R^{27}$), $C_1$-$C_4$, or $C_1$-$C_2$ alkoxycarbonyl, —$NR^{28}R^{29}$, $C_1$-$C_4$, or $C_1$-$C_2$ alkylcarbonylamino, $C_1$-$C_4$, or $C_1$-$C_2$ alkylsulphonylamino, phenylsulphonylamino, —$C(O)NHR^{30}$, —$SO_2NHR^{33}$ and $C_0$-$C_4$ or $C_0$-$C_2$ alkyl-$R^{34}$.

In another embodiment, $R^7$ represents a 5- to 10-membered (for example 6- to 10-membered) aromatic ring system optionally substituted by one or two substituents independently selected from halogen (e.g. fluorine, chlorine, bromine or iodine), trifluoromethyl, hydroxyl, carboxyl, $C_1$-$C_4$, or $C_1$-$C_2$ alkyl (optionally substituted by at least one, e.g. one or two, —$NR^{24}R^{25}$), $C_1$-$C_4$, or $C_1$-$C_2$ alkoxy (optionally substituted by at least one, e.g. one or two, —$NR^{26}R^{27}$), $C_1$-$C_4$, or $C_1$-$C_2$ alkoxycarbonyl, —$NR^{28}R^{29}$, $C_1$-$C_4$, or $C_1$-$C_2$ alkylcarbonylamino, $C_1$-$C_4$, or $C_1$-$C_2$ alkylsulphonylamino, phenylsulphonylamino, —C(O)$NHR^{30}$, —$SO_2NHR^{33}$, $C_0$-$C_4$ or $C_0$-$C_2$ alkyl-$R^{34}$, phenyl and a 5- to 6-membered heteroaromatic ring.

In another embodiment, $R^7$ represents a 6- to 10-membered aromatic ring system optionally substituted by one or two substituents independently selected from halogen (e.g. fluorine, chlorine, bromine or iodine), trifluoromethyl, hydroxyl, carboxyl, $C_1$-$C_4$, or $C_1$-$C_2$ alkyl (optionally substituted by at least one, e.g. one or two, —$NR^{24}R^{25}$), $C_1$-$C_4$, or $C_1$-$C_2$ alkoxy (optionally substituted by at least one, e.g. one or two, —$NR^{26}R^{27}$), $C_1$-$C_4$, or $C_1$-$C_2$ alkoxycarbonyl, —$NR^{28}R^{29}$, $C_1$-$C_4$, or $C_1$-$C_2$ alkylcarbonylamino, $C_1$-$C_4$, or $C_1$-$C_2$ alkylsulphonylamino, phenylsulphonylamino, —C(O)$NHR^{30}$, —$SO_2NHR^{33}$ and $C_0$-$C_4$ or $C_0$-$C_2$ alkyl-$R^{34}$.

In a further embodiment, $R^7$ represents a 5- to 10-membered (for example 6- to 10-membered) aromatic ring system optionally substituted by one or more (e.g. one, two, three or four) halogen atoms.

In a further embodiment $R^7$ is phenyl or naphthyl optionally substituted by halogen (for example fluoro, chloro or bromo), hydroxy, $C_{1-4}$ alkyl, $C_{1-4}$ alkoxy, $CF_3$ or $OCF_3$.

In another embodiment of the invention $R^{24}$, $R^{25}$, $R^{26}$, $R^{27}$, $R^{28}$ and $R^{29}$ each independently represent hydrogen or $C_1$-$C_6$, or $C_1$-$C_4$, or $C_1$-$C_2$ alkyl. It should be understood that if there is more than one group —$NR^{24}R^{25}$, the groups may be the same as, or different from, one another. Similar comments apply if there is more than one group —$NR^{26}R^{27}$.

In a further embodiment $R^{30}$ represents hydrogen; $C_1$-$C_6$, or $C_1$-$C_4$, or $C_1$-$C_2$ alkyl; phenyl-$C_0$-$C_6$, or $C_0$-$C_4$, or $C_0$-$C_2$ alkyl (e.g. phenyl or benzyl); or $C_1$-$C_6$, $C_1$-$C_4$, $C_1$-$C_2$, $C_2$-$C_6$ or $C_2$-$C_4$ alkylene-$NR^{31}R^{32}$ and either $R^{31}$ and $R^{32}$ each independently represent hydrogen or $C_1$-$C_6$, or $C_1$-$C_4$, or $C_1$-$C_2$ alkyl, or $R^{31}$ and $R^{32}$ together with the nitrogen atom to which they are attached form a 4- to 6-membered saturated heterocyclic ring optionally comprising a further ring heteroatom selected from nitrogen and oxygen such as azetidinyl, pyrrolidinyl, piperidinyl, piperazinyl or morpholinyl.

In a further embodiment $R^{30}$ represents hydrogen; $C_1$-$C_6$, or $C_1$-$C_4$, or $C_1$-$C_2$ alkyl; phenyl-$C_0$-$C_6$, or $C_0$-$C_4$, or $C_0$-$C_2$ alkyl (e.g. phenyl or benzyl); or $C_2$-$C_6$ or $C_2$-$C_4$ alkylene-$NR^{31}R^{32}$ and either $R^{31}$ and $R^{32}$ each independently represent hydrogen or $C_1$-$C_6$, or $C_1$-$C_4$, or $C_1$-$C_2$ alkyl, or $R^{31}$ and $R^{32}$ together with the nitrogen atom to which they are attached form a 4- to 6-membered saturated heterocyclic ring optionally comprising a further ring heteroatom selected from nitrogen and oxygen such as azetidinyl, pyrrolidinyl, piperidinyl, piperazinyl or morpholinyl.

In a still further embodiment $R^{30}$ represents hydrogen; $C_1$-$C_6$, or $C_1$-$C_4$, or $C_1$-$C_2$ alkylene-$NR^{31}R^{32}$ and either $R^{31}$ and $R^{32}$ each independently represent hydrogen or $C_1$-$C_6$, or $C_1$-$C_4$, or $C_1$-$C_2$ alkyl, or $R^{31}$ and $R^{32}$ together with the nitrogen atom to which they are attached form a 4- to 6-membered saturated heterocyclic ring optionally comprising a further ring heteroatom selected from nitrogen and oxygen such as azetidinyl, pyrrolidinyl, piperidinyl, piperazinyl or morpholinyl.

In a further embodiment $R^{33}$ represents hydrogen; $C_1$-$C_6$, or $C_1$-$C_4$, or $C_1$-$C_2$ alkyl; phenyl-$C_0$-$C_6$, or $C_0$-$C_4$, or $C_0$-$C_2$ alkyl (e.g. phenyl or benzyl); or $C_2$-$C_6$ or $C_2$-$C_4$ alkylene-$NR^{37}R^{38}$ and either $R^{37}$ and $R^{38}$ each independently represent hydrogen or $C_1$-$C_6$, or $C_1$-$C_4$, or $C_1$-$C_2$ alkyl, or $R^{37}$ and $R^{38}$ together with the nitrogen atom to which they are attached form a 4- to 6-membered saturated heterocyclic ring optionally comprising a further ring heteroatom selected from nitrogen and oxygen such as azetidinyl, pyrrolidinyl, piperidinyl, piperazinyl or morpholinyl.

In another embodiment $R^{33}$ represents hydrogen; $C_1$-$C_6$, or $C_1$-$C_4$, or $C_1$-$C_2$ alkyl or phenyl.

In a further embodiment $R^{34}$ represents a saturated, 5- or 6-membered nitrogen-containing ring, e.g. a ring containing one or two ring nitrogen atoms such as hydantoin.

In a still further embodiment $R^{35}$ and $R^{36}$ each independently represent hydrogen or $C_1$-$C_6$, or $C_1$-$C_4$, or $C_1$-$C_2$ alkyl.

In another embodiment the invention provides a compound of formula (I) wherein
  $R^1$ is hydrogen;
  e is 0 or 1 (for example 1);
  $R^2$ and $R^3$ are hydrogen or methyl (for example $R^2$ and $R^3$ are both hydrogen);
  $R^4$ and $R^5$, and, when present, $R^{4'}$ and $R^{5'}$ are all hydrogen;
  A is C(O);
  D is O;
  m is 1 or 2 (for example 1);
  n is 1;
  $R^{7a}$ and $R^{7b}$ are, independently, hydrogen or $C_{1-4}$ alkyl (for example methyl), (for example $R^{7a}$ and $R^{7b}$ are both hydrogen);
  $R^7$ is phenyl or naphthyl optionally substituted by halogen (for example fluoro, chloro or bromo), hydroxy, $C_{1-4}$ alkyl, $C_{1-4}$ alkoxy, $CF_3$ or $OCF_3$;
  $R^6$ is $(CH_2)_q R^{10a}$, wherein q is 0, 1, 2 or 3 (for example 2);
  $R^{10a}$ is phenyl, pyridyl, $NR^{9a}R^{9b}$ or piperidinyl (optionally N-substituted by C(O)O($C_{1-6}$ alkyl)); and $R^{9a}$ and $R^{9b}$ are, independently, $C_{1-4}$ alkyl (for example methyl or ethyl);

or a pharmaceutically acceptable salt thereof.

In an embodiment of the invention (subject to the proviso hereinbefore defined),
  $R^1$ represents hydrogen;
  e is 0 or 1;
  each of $R^2$, $R^3$, $R^4$, $R^5$, $R^{4'}$ and $R^{5'}$ represents hydrogen;
  A represents C(O) or $CH_2$;
  D represents oxygen;
  m is 1;
  n is 1;
  $R^6$ represents a group —$(X)_p$—Y-$(Z)_q$-$R^{10}$;
  X represents a $C_1$-$C_5$ alkylene group;
  Z represents a $C_1$-$C_2$ alkylene group;
  p and q each independently represent 0 or 1;
  Y represents a bond, oxygen, $CH_2$ or $NR^9$;
  $R^9$ represents methyl or ethyl;
  $R^{10}$ represents hydrogen, phenyl, pyridinyl, or a piperidinyl group optionally substituted by $C_4$ alkoxycarbonyl; and
  $R^7$ represents a 6- to 10-membered aromatic ring system optionally substituted by one or more halogen atoms.

In an embodiment of the invention (subject to the proviso hereinbefore defined),
  $R^1$ represents hydrogen;
  e is 0 or 1;
  each of $R^2$, $R^3$, $R^4$, $R^5$, $R^{4'}$ and $R^{5'}$ represents hydrogen;
  A represents C(O);
  D represents oxygen;
  m is 1;
  n is 1;
  $R^6$ represents a group —$(X)_p$—Y-$(Z)_q$-$R^{10}$;
  X represents a $C_1$-$C_5$ alkylene group;
  Z represents a $C_1$-$C_2$ alkylene group;
  p and q each independently represent 0 or 1;
  Y represents a bond, oxygen, $CH_2$ or $NR^9$;

R⁹ represents methyl or ethyl;

R¹⁰ represents hydrogen, phenyl, pyridinyl, or a piperidinyl group optionally substituted by C₄ alkoxycarbonyl; and R⁷ represents a 6- to 10-membered aromatic ring system optionally substituted by one or more halogen atoms.

An example of a compound of the invention is:

tert-Butyl 4-({(2-{[2-(4-hydroxy-2-oxo-2,3-dihydro-1,3-benzothiazol-7-yl)ethyl]amino}ethyl)[3-(2-phenylethoxy)propanoyl]amino}methyl)piperidine-1-carboxylate;

N-{2-[2-(4-Hydroxy-2-oxo-2,3-dihydro-benzothiazol-7-yl)-ethylamino]-ethyl}-3-phenethyloxy-N-piperidin-4-ylmethyl-propionamide;

N-[2-[2-(4-Hydroxy-2-oxo-3H-benzothiazol-7-yl)ethylamino]ethyl]-N-phenethyl-3-phenethyloxy-propanamide;

N-Benzyl-N-[2-[2-(4-hydroxy-2-oxo-3H-benzothiazol-7-yl)ethylamino]ethyl]-3-phenethyloxy-propanamide;

N-[2-[2-(4-Hydroxy-2-oxo-3H-benzothiazol-7-yl)ethylamino]ethyl]-3-phenethyloxy-N-(3-pyridylmethyl)propanamide;

N-[2-[2-(4-Hydroxy-2-oxo-3H-benzothiazol-7-yl)ethylamino]ethyl]-3-phenethyloxy-N-phenyl-propanamide;

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide;

N-(3-{[2-(4-Hydroxy-2-oxo-2,3-dihydro-1,3-benzothiazol-7-yl)ethyl]amino}propyl)-3-(2-phenylethoxy)-N-(2-phenylethyl)propanamide;

N-[2-[2-(4-Hydroxy-2-oxo-3H-benzothiazol-7-yl)ethylamino]ethyl]-3-phenethyloxy-N—(S-phenethyloxypentyl)propanamide;

3-[2-(4-Bromophenyl)ethoxy]-N-[2-[2-(4-hydroxy-2-oxo-3H-benzothiazol-7-yl)ethylamino]ethyl]-N-phenethyl-propanamide;

N-{2-[2-(4-Hydroxy-2-oxo-2,3-dihydro-benzothiazol-7-yl)-ethylamino]-ethyl}-3-phenethyloxy-N-piperidin-4-yl propanamide;

N-[2-(Diethylamino)ethyl]-N-(2-{[2-(4-hydroxy-2-oxo-2,3-dihydro-1,3-benzothiazol-7-yl)ethyl]amino}ethyl)-3-(2-phenylethoxy)propanamide;

4-Hydroxy-7-[2-({2-[[3-(2-phenylethoxy)propyl] (2-phenylethyl)amino]ethyl}amino)-ethyl]-1,3-benzothiazol-2 (3H)-one;

N-[2-(Dimethylamino)ethyl]-N-(2-{[2-(4-hydroxy-2-oxo-2,3-dihydro-1,3-benzothiazol-7-yl)ethyl]amino}ethyl)-3-(2-phenylethoxy)propanamide;

N-[2-(Diethylamino)ethyl]-N-(2-{[2-(4-hydroxy-2-oxo-2,3-dihydro-1,3-benzothiazol-7-yl)ethyl]amino-3 ethyl)-3-{2-[2-(trifluoromethyl)phenyl]ethoxy}propanamide;

3-[2-(3-Chlorophenyl)ethoxy]-N-[2-(diethylamino)ethyl]-N-(2-{[2-(4-hydroxy-2-oxo-2,3-dihydro-1,3-benzothiazol-7-yl)ethyl]amino}ethyl)propanamide;

N-[2-(Diethylamino)ethyl]-N-(2-{[2-(4-hydroxy-2-oxo-2,3-dihydro-1,3-benzothiazol-7-yl)ethyl]amino}ethyl)-3-[2-(4-hydroxyphenyl)ethoxy]propanamide;

3-[2-(2,3-Dichlorophenyl)ethoxy]-N-(2-diethylaminoethyl)-N-(2-{[2-(4-hydroxy-2-oxo-2,3-dihydro-1,3-benzothiazol-7-yl)ethyl]amino}ethyl)propanamide;

3-[2-(2-Bromo-5-methoxyphenyl)ethoxy]-N-[2-(diethylamino)ethyl]-N-(2-{[2-(4-hydroxy-2-oxo-2,3-dihydro-1,3-benzothiazol-7-yl)ethyl]amino}ethyl)propanamide;

N-(2-Diethylaminoethyl)-3-[2-(3-fluorophenyl)ethoxy]-N-{2-[2-(4-hydroxy-2-oxo-2,3-dihydro-1,3-benzothiazol-7-yl)ethylamino]ethyl}propanamide;

N-(2-Diethylaminoethyl)-N-{2-[2-(4-hydroxy-2-oxo-2,3-dihydro-1,3-benzothiazol-7-yl)ethylamino]ethyl}-3-(2-methyl-2-phenylpropoxy)propanamide;

3-[2-(2,6-Dichlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide;

N-(2-Diethylaminoethyl)-N-{2-[2-(4-hydroxy-2-oxo-2,3-dihydro-1,3-benzothiazol-7-yl)ethylamino]ethyl}-3-[2-(3-trifluoromethylphenyl)ethoxy]propanamide;

3-[2-(4-Chlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide;

3-[2-(3,4-Dichlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide;

N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-methylphenyl)ethoxy]propanamide;

N-(2-Diethylaminoethyl)-N-{2-[2-(4-hydroxy-2-oxo-2,3-dihydro-1,3-benzothiazol-7-yl)ethylamino]ethyl}-3-[2-(3-hydroxyphenyl)ethoxy]propanamide;

N-(2-Diethylaminoethyl)-N-{2-[2-(4-hydroxy-2-oxo-2,3-dihydro-1,3-benzothiazol-7-yl)ethylamino]ethyl}-3-[2-(3-methoxyphenyl)ethoxy]propanamide;

3-[2-(2-Chlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide; or, N-[2-(Diethylamino)ethyl]-N-(2-{[2-(4-hydroxy-2-oxo-2,3-dihydro-1,3-benzothiazol-7-yl)ethyl]amino}ethyl)-3-[2-(2-naphthyl)ethoxy]propanamide or a pharmaceutically acceptable salt thereof.

The present invention further provides a process for the preparation of a compound of formula (I) or a pharmaceutically acceptable salt thereof as defined above which comprises, (a) reacting a compound of formula (II)

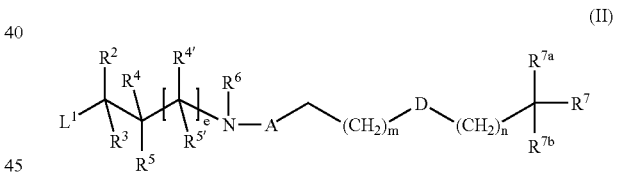

wherein L¹ represents a leaving group (e.g. chlorine, bromine, iodine, methanesulfonate or para-toluenesulfonate) and e, R², R³, R⁴, R⁵, R⁴', R⁵', R⁶, R⁷, R⁷ᵃ, R⁷ᵇ, A, D, m and n are as defined in formula (I) but R² and R³ are not both alkyl, with a compound of formula (III) or a suitable salt thereof (e.g. hydrobromide or hydrochloride salt)

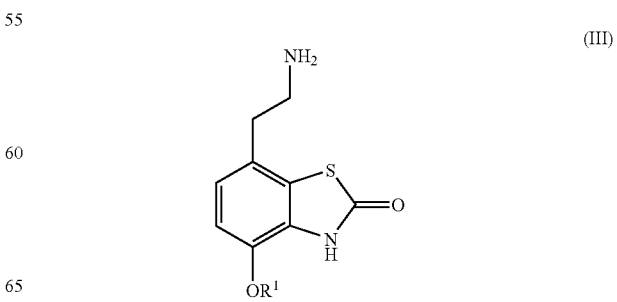

wherein $R^1$ is as defined in formula (I), in the presence of a base (e.g. potassium carbonate, triethylamine or diisopropylethylamine); or (b) when $R^2$ and $R^3$ each represent hydrogen, reacting a compound of formula (IV)

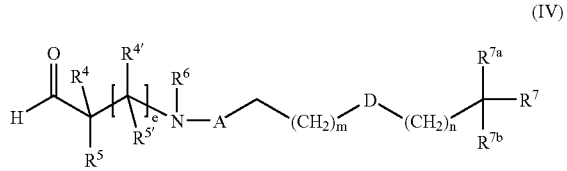
(IV)

wherein e, $R^4$, $R^5$, $R^{4'}$, $R^{5'}$, $R^6$, $R^7$, $R^{7a}$, $R^{7b}$, A, D, m and n are as defined in formula (I), with a compound of formula (III) or a suitable salt thereof as defined in (a) above in the presence of a suitable reducing agent (e.g. sodium cyanoborohydride, sodium triacetoxyborohydride, or hydrogen in the presence of a palladium on carbon or palladium oxide catalyst); or (c) when $R^2$ and $R^3$ each represent hydrogen, contacting a compound of formula (V)

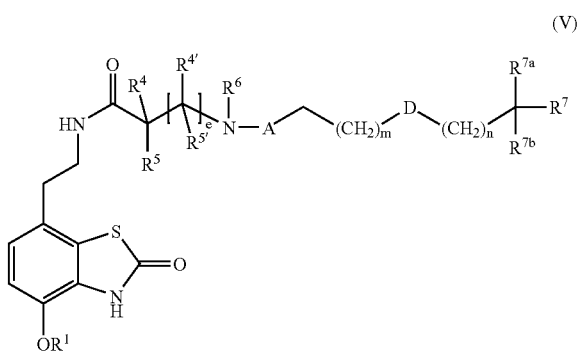
(V)

wherein e, $R^1$, $R^4$, $R^5$, $R^{4'}$, $R^{5'}$, $R^6$, $R^7$, $R^{7a}$, $R^{7b}$, A, D, m and n are as defined in formula (I) with a suitable reducing agent (e.g. lithium aluminium hydride or borane tetrahydrofuran complex);

and optionally after (a), (b) or (c) carrying out one or more of the following:

converting the compound obtained to a further compound of the invention forming a pharmaceutically acceptable salt of the compound.

In process (a), the reaction may conveniently be carried out in an organic solvent such as N,N-dimethylformamide, ethanol, n-butanol or dimethyl sulfoxide, at a temperature, for example, in the range from 50 to 140° C.

In process (b), the reaction may conveniently be carried out in an organic solvent such as methanol, ethanol, dichloromethane, acetic acid or N,N-dimethylformamide containing up to 10% w of water and acetic acid.

In process (c), the reaction may conveniently be carried out in an organic solvent such as tetrahydrofuran, at a temperature, for example, in the range from 0 to 60° C.

Compounds of formula (II) in which A represents carbonyl may be prepared by reacting a compound of formula (X)

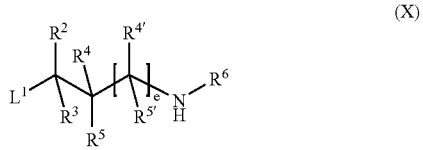
(X)

wherein $L^1$, e, $R^2$, $R^3$, $R^4$, $R^5$, $R^{4'}$, $R^{5'}$ and $R^6$ are as defined in formula (II), with a compound of formula (XI)

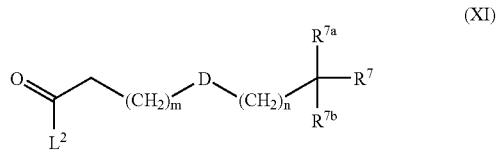
(XI)

wherein $L^2$ represents a leaving group (such as hydroxyl or halogen, e.g. chlorine) and m, n, D, $R^7$, $R^{7a}$ and $R^{7b}$ are as defined in formula (II).

When $L^2$ represents hydroxyl, the reaction is conveniently carried out in the presence of an activating reagent, for example, carbonyldiimidazole or O-(7-azabenzotriazol-1-yl)-N,N,N',N'-tetramethyluroniumhexafluorophosphate (HATU), in an organic solvent, for example, N,N-dimethylformamide or dichloromethane, at a temperature, for example in the range from 0 to 60° C.

When $L^2$ represents chlorine, the reaction is conveniently carried out in the presence of a base, for example, triethylamine or diisopropylethylamine in an organic solvent, for example, dichloromethane or tetrahydrofuran at a temperature, for example, in the range from 0 to 25° C.

Compounds of formula (I) in which A represents methylene may be prepared by contacting a corresponding compound of formula (I) in which A represents carbonyl with a reducing agent, for example, lithium aluminium hydride or borane tetrahydrofuran complex in an organic solvent, for example, tetrahydrofuran at a temperature, for example in the range from 0 to 60° C.

Compounds of formula (II) in which A represents sulphonyl may be prepared by reacting a compound of formula (X) as defined above with a compound of formula (XII)

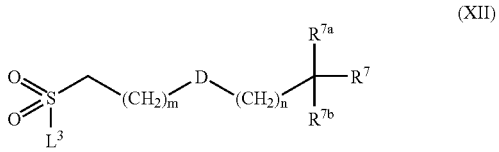
(XII)

wherein $L^3$ represents a leaving group (e.g. halogen) and m, n, D, $R^7$, $R^{7a}$ and $R^{7b}$ are as defined in formula (II). The reaction may be carried out in the presence of a base, for example, triethylamine or diisopropylethylamine in an organic solvent, for example, dichloromethane or tetrahydrofuran at a temperature, for example, in the range from 0 to 25° C.

Compounds of formula (III) may be prepared as described in Organic Process Research & Development 2004, 8(4), 628-642.

Compounds of formula (IV) may be prepared by treating a compound of formula (XIII)

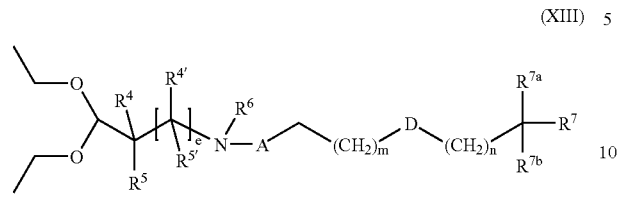

(XIII)

in which e, $R^4$, $R^5$, $R^{4'}$, $R^{5'}$, $R^6$, $R^7$, $R^{7a}$, $R^{7b}$, A, D, m and n are as defined in formula (IV), with a strong acid such as concentrated hydrochloric acid in an organic solvent such as 1,4-dioxane at a temperature, for example, of 25° C.

Compounds of formula (IV) may alternatively be prepared by oxidising a compound of formula (XIV)

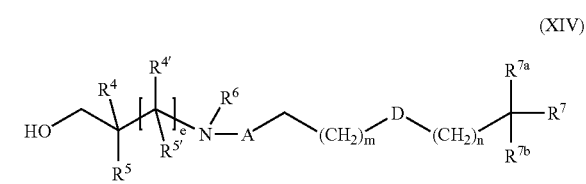

(XIV)

wherein e, $R^4$, $R^5$, $R^{4'}$, $R^{5'}$, $R^6$, $R^7$, $R^{7a}$, $R^{7b}$, A, D, m and n are as defined in formula (IV), with an oxidising agent, for example pyridinium chloro chromate or Dess-Martin periodinane in an organic solvent, for example, dichloromethane at a temperature, for example, of 25° C. Other oxidative procedures may also be employed as known to persons skilled in the art, for example, the Swern oxidation which is outlined in Synthesis, 1981, 3, 165.

Compounds of formula (V) may be prepared by reacting a compound of formula (XV)

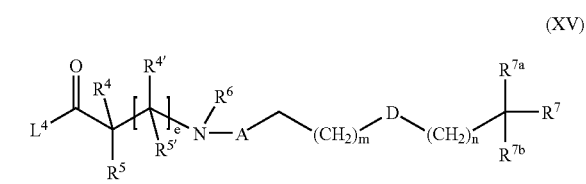

(XV)

wherein $L^4$ represents a leaving group (e.g. chlorine or hydroxyl) and e, $R^4$, $R^5$, $R^{4'}$, $R^{5'}$, $R^6$, $R^7$, $R^{7a}$, $R^{7b}$, A, D, m and n are as defined in formula (V), with a compound of formula (III) or a suitable salt thereof as defined above.

When $L^4$ represents chlorine, the reaction is conveniently carried out in the presence of a base, for example, triethylamine or diisopropylethylamine in an organic solvent, for example, dichloromethane at a temperature, for example, in the range from 0 to 25° C.

When $L^4$ represents hydroxyl, the reaction is conveniently carried out in the presence of an activating reagent, for example, carbonyldiimidazole or O-(7-azabenzotriazol-1-yl)-N,N,N',N'-tetramethyluroniumhexafluorophosphate (HATU), in an organic solvent, for example, N,N-dimethylformamide or dichloromethane, at a temperature, for example in the range from 0 to 60° C.

Compounds of formula (XIII) in which A represents carbonyl may be prepared by reacting a compound of formula (XVI)

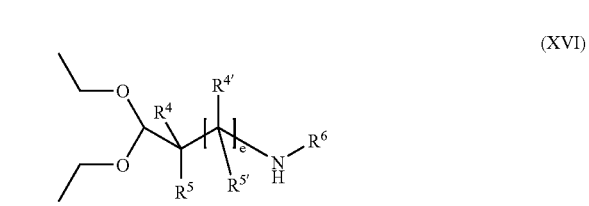

(XVI)

wherein e, $R^4$, $R^5$, $R^{4'}$, $R^{5'}$ and $R^6$ are as defined in formula (XIII), with a compound of formula (XI) as defined above.

Compounds of formula (XIII) in which A represents sulphonyl may be prepared by reacting a compound of formula (XVI) as defined above with a compound of formula (XII) as defined above, e.g. in the presence of a base such as triethylamine or diisopropylethylamine in an organic solvent such as dichloromethane or tetrahydrofuran at a temperature, for example, in the range from 0 to 25° C.

Compounds of formula (XIII) in which A represents methylene may be prepared by reacting a compound of formula (XVI) as defined above with a compound of formula (XVII)

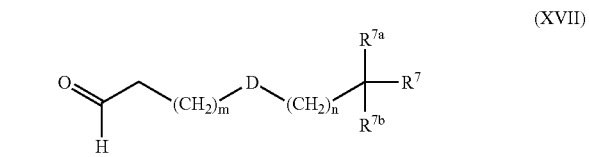

(XVII)

wherein m, n, D, $R^7$, $R^{7a}$ and $R^{7b}$ are as defined in formula (XIII), in the presence of a reducing agent, for example, sodium cyanoborohydride or sodium triacetoxyborohydride in an organic solvent, for example, methanol, ethanol, dichloromethane or N,N-dimethylformamide containing, for example, 0-10% w water. The reaction could also be performed in an organic solvent, for example, ethanol, acetic acid or methanol (or a combination of either) under an atmosphere of hydrogen gas with a suitable catalyst, for example, 5-10% w palladium on carbon or platinum oxide.

Compounds of formulae (XIV) and (XV) may be prepared by processes similar to those described for the preparation of compounds of formula (XIII).

Compounds of formula (XVI) may be prepared by reacting a compound of formula (XVIII)

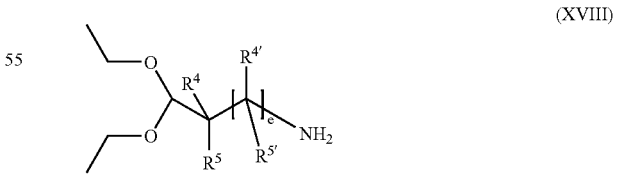

(XVIII)

wherein e, $R^4$, $R^5$, $R^{4'}$ and $R^{5'}$ are as defined in formula (XVI), with a compound of formula (XIX), $R^6$—CHO, wherein $R^6$ is as defined in formula (XVI), in the presence of a reducing agent, for example, sodium cyanoborohydride or sodium triacetoxyborohydride in an organic solvent, for example, methanol, ethanol, dichloromethane or N,N-dimethylformamide containing, for example, 0-10% w water. The reaction could also be performed in an organic solvent, for example, ethanol, acetic acid or methanol (or a combination of either) under an atmosphere of hydrogen gas with a suitable catalyst, for example, 5-10% w palladium on carbon or platinum oxide.

Compound of formula (I) wherein A is C(O), e is 0, and $R^2$, $R^3$, $R^4$ and $R^5$ are all hydrogen, can be prepared by deprotection of a compound of formula (XIX):

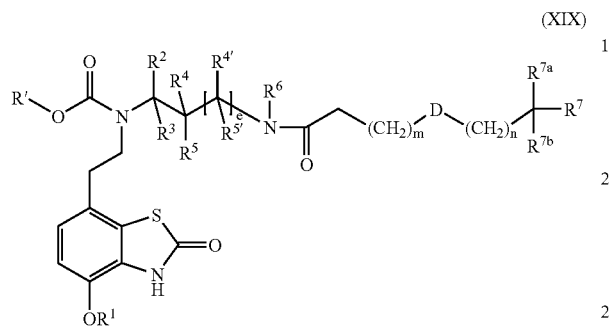

(XIX)

wherein R' is alkyl or other suitable part of a protecting group (such as Cbz), for example using trifluoroacetic acid in a suitable solvent (for example dichloromethane) or hydrogenation over Pd/C in an alcoholic solvent.

A compound of formula (XIX) can be prepared by coupling a compound of formula (XX)

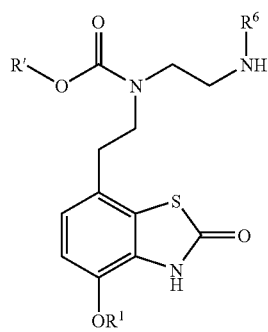

(XX)

with an acid or acid derivative of formula (XXI):

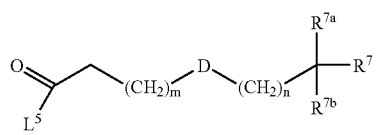

(XXI)

wherein $R^5$ is OH, Cl or, together with the remainder of formula (XXI), a suitable anhydride; in a suitable solvent and, optionally, in a suitable coupling agent (such as DCC, PyBrOP or HATU).

A compound of formula (XX) can be prepared by reacting a compound of formula (XXII):

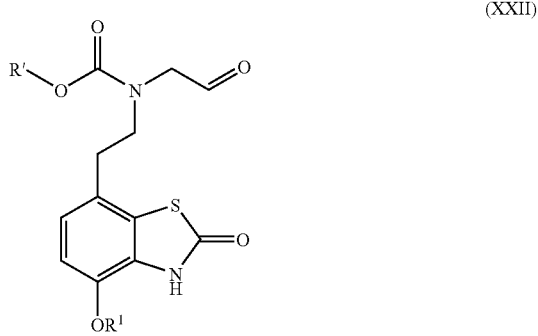

(XXII)

with $NH_2R^6$, for example using reductive amination conditions (such as using sodium cyanoborohydride or sodium acetoxyborohydride in an aqueous alcoholic solution) or catalytic hydrogenation (eg Pd/C) in water or with a water miscible cosolvent (for example THF, but, for example, a solvent other than an alcohol).

A compound of formula (XXII) can be prepared by acetal hydrolysis of a compound of formula (XXIII):

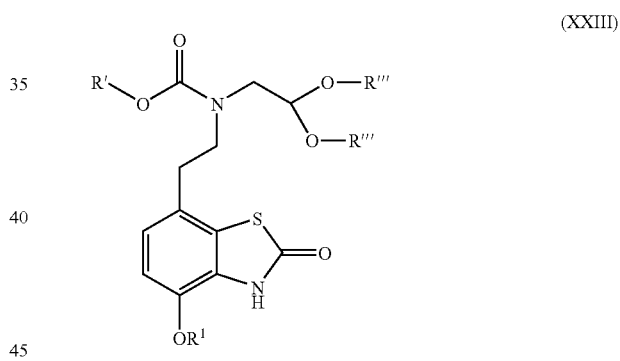

(XXIII)

wherein each R''' is, independently, $C_{1-6}$ alkyl, using, for example an acid in presence of water or another carbonyl compound (trans acetalisation with eg acetone).

A compound of formula (XXIII) can be prepared by coupling a compound of formula (XXVI)

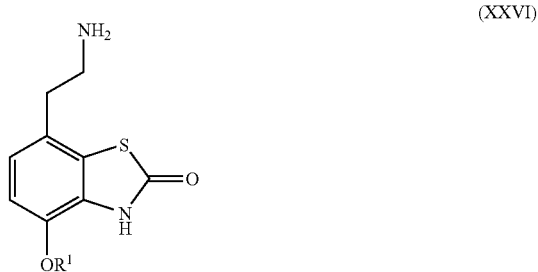

(XXVI)

with a compound of formula (XXV)

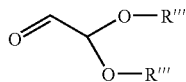
(XXV)

for example using reductive amination (such as using sodium cyanoborohydride or sodium acetoxyborohydride in an aqueous alcoholic solution) or catalytic hydrogenation (eg Pd/C, in water or with a water miscible cosolvent (for example THF, but, for example, a solvent other than an alcohol); and then protecting the product so formed with R'OC(O)R'''' where R'''' is chloride or R'C(O)O (that is, the compound as a whole is an anhydride) under standard conditions known in the literature.

Compounds of formula (I) wherein A is C(O) and $R^2$ and $R^3$ are both alkyl can be prepared by coupling a compound of formula (XI) with a compound of formula

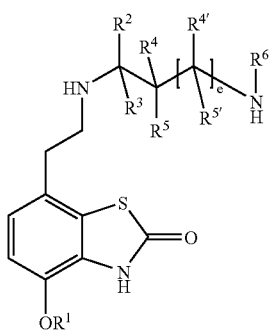
(XXVI)

wherein $L^2$ is a leaving group (such as hydroxy or halogen, for example chloro) under standard literature conditions.

A compound of formula (XXVI) can be prepared by reducing a compound of formula (XXVII):

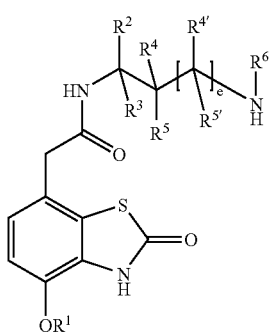
(XXVII)

under literature amide reducing conditions (for example using borane in tetrahydrofuran at a temperature in the range 10-50° C.).

A compound of formula (XXVII) wherein $R^6$ is other than hydrogen, can be prepared by reductive amination of a compound of formula (XXVIII):

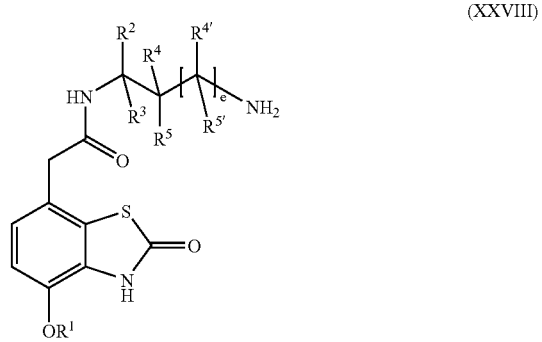
(XXVIII)

with an appropriate aldehyde (for example an aldehyde of formula (O)CHCH$_2$—Y-(Z)$_q$-R$^{10}$) either by hydrogenation (for example 1-5 bar of hydrogen using a suitable catalyst (such as Palladium on carbon) in a suitable solvent (for example ethanol) at a temperature in the range 10-50° C.), or by using sodium triacetoxyborohydride or cyanoborohydride in a suitable solvent (such as methanol and acetic acid) at a temperature in the range 10-40° C.

A compound of formula (XXVIII) can be prepared by deprotecting a compound of formula (XXIX):

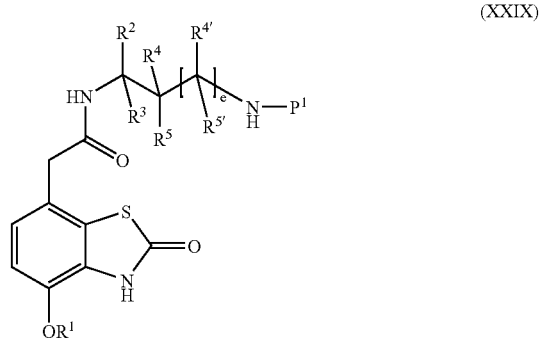
(XXIX)

wherein $P^1$ is a suitable protecting group, such as tert-butoxycarbonyl, under standard literature conditions (such as trifluoroacetic acid in dichloromethane at 10-30° C.

A compound of formula (XXIX) can be prepared by coupling a compound of formula (XXX):

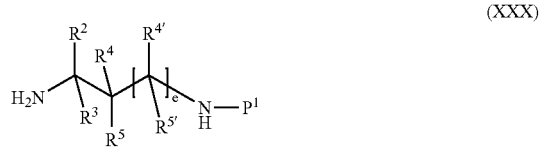
(XXX)

with a compound of formula (XXXI):

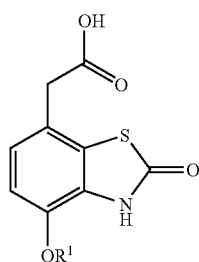

(XXXI)

in the presence of a peptide coupling agent (such as DCC, EDCI or HATU), in an inert solvent (for example dichloromethane) in the presence of a suitable base (such as a tertiary amine, for example triethylamine or Hunig's base) at a temperature in the range −20 to 50° C.

Compounds of formulae (X), (XI), (XII), (XVII), (XVIII), (XIX), (XXVI), (XXV), (XXX) and (XXXI) are either commercially available, are known in the literature or may be prepared using known techniques.

Compounds of formula (I) can be converted into further compounds of formula (I) using standard procedures.

For example, compounds of formula (I) in which $R^{10}$ represents a 3- to 10-membered ring system (e.g. piperidinyl) substituted by a $C_1$-$C_6$ alkoxycarbonyl substituent group may be converted to the corresponding compounds in which the ring system is unsubstituted by treating the former with, for example, trifluoroacetic acid or anhydrous hydrogen chloride, in an organic solvent such as dichloromethane or 1,4-dioxane at a temperature, for example, in the range from 15 to 30° C.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, for example an acid addition salt such as a hydrochloride (for example a dihydrochloride), hydrobromide (for example a dihydrobromide), trifluoroacetate (for example a di-trifluoroacetate), sulphate, phosphate, acetate, fumarate, maleate, tartrate, lactate, citrate, pyruvate, succinate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopenic purpura, eosinophilic fascitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinophilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a compound of formula (I) or a pharmaceutically acceptable salt thereof as hereinbefore defined.

In particular, the compounds of this invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50%/w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_9$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The invention therefore further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerin; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxifylline.

In addition the invention relates to a combination of a compound of the invention, or a pharmaceutically acceptable salt thereof, with a monoclonal antibody targeting B-Lymphocytes (such as CD20 (rituximab), MRA-aIL16R) or T-Lymphocytes (CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591 MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxifylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptyline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof. A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; (xxvii) inhibitor of transcription factor activation such as NFkB, API or STATS; or (xxviii) a glucocorticoid receptor (GR-receptor) agonist.

In a further aspect the present invention provides a combination (for example for the treatment of COPD, asthma or allergic rhinitis) of a compound of formula (I) and one or more agents selected from the list comprising:
 a non-steroidal glucocorticoid receptor (GR-receptor) agonist;
 a PDE4 inhibitor including an inhibitor of the isoform PDE4D;
 a muscarinic receptor antagonist (for example a M1, M2 or M3 antagonist, such as a selective M3 antagonist) such as ipratropium bromide, tiotropium bromide, oxitropium bromide, pirenzepine or telenzepine;
 a modulator of chemokine receptor function (such as a CCR1 receptor antagonist); or,
 an inhibitor of p38 kinase function.

A compound of the invention, or a pharmaceutically acceptable salt thereof, can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidin like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);
(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;
(iii) an agent which inhibits cancer cell invasion (for example a metalloproteinase inhibitor like marimastat or an inhibitor of urokinase plasminogen activator receptor function);
(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

The present invention will now be further explained by reference to the following illustrative examples.

General Methods $^1$H NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The following method was used for LC/MS analysis:

Instrument Agilent 1100; Column Waters Symmetry 2.1× 30 mm; Mass APCI; Flow rate 0.7 ml/min; Wavelength 254 nm; Solvent A: water+0.1% TFA; Solvent B: acetonitrile+ 0.1% TFA; Gradient 15-95%/B 8 min, 95% B 1 min.

Analytical chromatography was run on a Symmetry C$_{18}$-column, 2.1×30 mm with 3.5 µm particle size, with acetonitrile/water/0.1% trifluoroacetic acid as mobile phase in a gradient from 5% to 95% acetonitrile over 8 minutes at a flow of 0.7 ml/min.

The abbreviations or terms used in the examples have the following meanings:

SCX: Solid phase extraction with a sulfonic acid sorbent
HPLC: High performance liquid chromatography
DMF: N,N-Dimethylformamide

EXAMPLE 1 tert-Butyl 4-({(2-{[2-(4-hydroxy-2-oxo-2,3-dihydro-1,3-benzothiazol-7-yl)ethyl]amino}ethyl)[3-(2-phenylethoxy)propanoyl]amino}methyl)piperidine-1-carboxylate

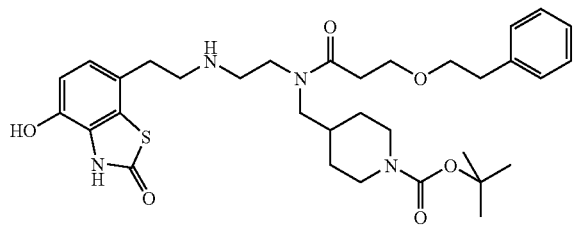

a) tert-Butyl 4-{[(2-hydroxyethyl)amino]methyl}piperidine-1-carboxylate tert-Butyl 4-(hydroxymethyl)piperidine-1-carboxylate (4.3 g) was dissolved in dichloromethane (50 ml) and pyridinium chlorochromate (6.46 g) was added. The reaction was stirred for 2 hours and filtered through a thin bed of silica eluting with ethyl acetate/hexane (⅓). The resulting aldehyde was dissolved in ethanol (20 mL) and ethanolamine (2.44 g) was added along with 10% palladium (Pd) on Carbon (100 mg). The reaction mixture was hydrogenated at 2.5 bar for 24 hours, filtered and concentrated. The residue was dissolved in methanol and passed through a SCX cartridge eluting with methanol. The product was eluted with 7N ammonia in methanol to afford the sub-titled compound (4.2 g) as an oil.

$^1$H NMR (400 MHz, CDCl$_3$) δ 3.63 (t, 2H), 2.77 (t, 2H), 2.52 (d, 2H), 1.74-1.67 (m, 2H), 1.63-1.54 (m, 1H), 1.46 (s, 9H), 1.12 (q, 2H).

b) tert-Butyl-4-({(2-hydroxyethyl)[3-(2-phenylethoxy)propanoyl]amino}-methyl)piperidine-1-carboxylate To a solution of tert-butyl 3-(2-phenylethoxy)propanoate prepared as described in WO 93/23385, 0.39 g) in dichloromethane (5 mL) was added trifluoroacetic acid (2 mL) and the mixture was stirred at room temperature for 3 hours and then concentrated. The residue was dissolved in dichloromethane (5 mL) and oxalyl chloride (2 g) was added. The reaction was stirred for 2 hours and then concentrated. The residue was dissolved in dichloromethane (5 mL) and this was added to a solution of 4-[(2-hydroxy-ethylamino)-methyl]-piperidine-1-carboxylic acid tert-butyl ester (0.516 g) and triethylamine (0.505 g) in dichloromethane (10 mL) and the resulting mixture was stirred for one hour. The reaction mixture was diluted with ethyl acetate (25 mL) and was washed with 2N hydrochloric acid, dried with anhydrous sodium sulphate, filtered and concentrated in vacuo to give the sub-titled compound as an oil.

$^1$H NMR (400 MHz, CDCl$_3$, rotameric mixture) δ 7.32-7.17 (m, 5H), 3.82-3.73 (m, 4H), 3.71-3.64 (m, 2H), 3.58-3.52 (m, 1H), 3.20-3.17 (m, 1H), 2.92-2.84 (m, 2H), 2.69-2.55 (m, 5H), 1.92-1.69 (m, 1H), 1.61 (t, 3H), 1.46 (s, 9H), 1.17-1.05 (m, 2H)

c) tert-Butyl 4-({(2-{[2-(4-hydroxy-2-oxo-2,3-dihydro-1,3-benzothiazol-7-yl)ethyl]amino}ethyl)[3-(2-phenylethoxy)propanoyl]amino}methyl)piperidine-1-carboxylate A solution of dimethyl sulfoxide (0.22 g) in dichloromethane (10 mL) was cooled to −60° C. and oxalyl chloride (0.351 g) was added. The reaction was stirred for 15 minutes and then a solution of tert-butyl 4-({(2-hydroxyethyl)[3-(2-phenylethoxy)propanoyl]amino}-methyl)piperidine-1-carboxylate (Example 1b), 0.8 g) in dichloromethane (5 mL) was added and the reaction stirred for a further 15 minutes. Triethylamine (0.466 g) was added and the reaction mixture was allowed to warm to room temperature and then poured into 2M hydrochloric acid and extracted into ethyl acetate. The organic phase was dried with anhydrous magnesium sulphate, filtered and concentrated in vacuo. The crude product was dissolved in methanol (10 mL) and 7-(2-aminoethyl)-4-hydroxy-1,3-benthiazol-2(3H)-one hydrobromide prepared according to the procedure outlined in Organic Process Research & Development 2004, 8(4), 628-642, 0.536 g) was added along with acetic acid (0.1 mL). After stirring at room temperature for 1 hour, sodium cyanoborohydride (0.1453 g) was added and the reaction mixture stirred overnight. Ammonia (7N in methanol, 1 mL) was added and the mixture was concentrated onto silica gel and the residue was purified by flash column chromatography eluting with 0.7N ammonia in methanol in dichloromethane (5-10%) to give the titled compound (0.75 g) as an oil.

m/e 627 (1+H)$^+$ $^1$H NMR (400 MHz, DMSO) δ 7.41-7.31 (m, 5H), 6.97 (d, 1H), 6.87 (d, 1H), 4.11-4.01 (m, 2H), 3.78-3.68 (m, 4H), 3.64-3.58 (m, 1H), 3.29 (t, 2H), 3.24-3.13 (m, 4H), 2.90 (t, 4H), 2.80-2.65 (m, 5H), 1.91-1.84 (m, 1H), 1.64 (t, 2H), 1.52 (s, 9H), 1.21-1.06 (m, 2H).

EXAMPLE 2

N-{2-[2-(4-Hydroxy-2-oxo-2,3-dihydro-benzothiazol-7-yl)-ethylamino]-ethyl}-3-phenethyloxy-N-piperidin-4-ylmethyl-propionamide

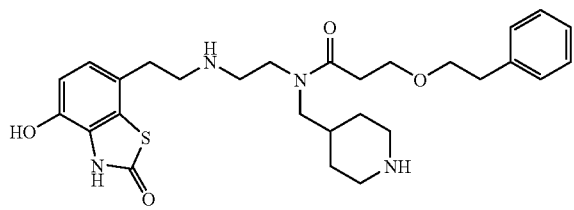

To a solution of 4-{[{2-[2-(4-hydroxy-2-oxo-2,3-dihydro-benzothiazol-7-yl)-ethylamino]-ethyl}-(3-phenethyloxypropionyl)-amino]-methyl}-piperidine-1-carboxylic acid tert-butyl ester (Example 1, 0.2 g) in dichloromethane (2 mL) was added trifluoroacetic acid (2 mL) and the reaction mixture was stirred for 30 minutes and then concentrated. The residue was dissolved in methanol (5 mL) and purified by reverse phase HPLC eluting with 5% to 95% acetonitrile in 0.2% trifluoroacetic acid. The fractions containing the product were concentrated and dissolved in methanol where 4N hydrogen chloride in 1,4-dioxane was added. The mixture was concentrated and the residue was triturated with ether, the ether was decanted and further concentration afforded the titled compound (0.13 g) as a hygroscopic solid.

m/e 527 (M+H)$^+$ $^1$H NMR (400 MHz, DMSO) δ 11.77 (d, 1H), 10.14 (d, 1H), 9.18 (s, 1H), 8.99 (s, 1H), 8.89-8.81 (m, 1H), 8.68-8.60 (m, 1H), 7.28-7.25 (m, 2H), 7.23-7.18 (m, 3H), 6.87 (dd, 1H), 6.77 (dd, 1H), 3.67-3.59 (m, 7H), 3.28-3.19 (m, 4H), 3.12-3.03 (m, 3H), 2.90-2.83 (m, 3H), 2.80-2.76 (m, 3H), 2.61 (t, 1H), 2.57 (t, 1H), 1.94-1.82 (m, 1H), 1.70 (t, 2H), 1.40-1.27 (m, 2H).

EXAMPLE 3

N-[2-[2-(4-Hydroxy-2-oxo-3H-benzothiazol-7-yl)ethylamino]ethyl]-N-phenethyl-3-phenethyloxy-propanamide

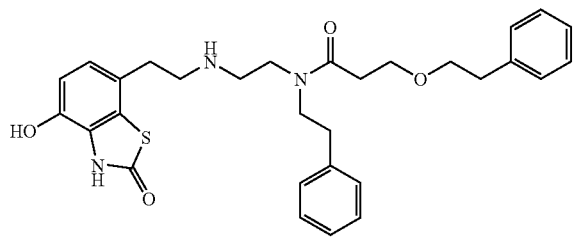

a) N-(2,2-Diethyloxyethyl)-N-phenethyl-3-phenethyloxy-propanamide

3-Phenethyloxypropanoic acid (0.34 g) was dissolved in dichloromethane (20 mL) and treated with oxalyl chloride (0.32 g) and a drop of dimethylformamide at ambient temperature. The resultant solution was stirred at ambient temperature for 2 hours. The solution was then concentrated and azeotroped with dichloromethane (2×20 mL). The collected residue was dissolved in dichloromethane and added, portionwise, to a stirred solution of 2,2-diethoxy-N-phenethyl-ethanamine (0.41 g) and triethylamine (0.6 mL), dissolved in dichloromethane (20 mL), at ambient temperature. The resultant solution was stirred at ambient temperature for 2 hours. The mixture was then concentrated, taken up in ethyl acetate (50 mL), washed with water (2×25 mL), washed with brine (50 mL), dried over anhydrous magnesium sulphate, filtered and concentrated to give the sub-titled compound (0.53 g) as a viscous oil.

m/e 414.0 (M+H)$^+$ $^1$H NMR (400 MHz, CDCl$_3$) δ 7.29-7.13 (m, 10H), 4.66 & 4.48 (t, 1H), 3.79-3.39 (m, 12H), 2.94-2.81 (m, 4H), 2.67 & 2.45 (t, 2H), 1.22-1.16 (m, 6H).

b) N-(2-Oxoethyl)-N-phenethyl-3-phenethyloxy-propanamide

N-(2,2-Diethyloxyethyl)-N-phenethyl-3-phenethyloxy-propanamide (Example 3a), 0.23 g) was dissolved in dioxane (5 mL) and treated with concentrated hydrochloric acid (1.5 mL) at ambient temperature. The resultant solution was stirred at ambient temperature for 2.5 hours. The reaction mixture was then poured into dichloromethane (20 mL) and washed with water (2×20 mL) and brine (20 mL). The organic layer was isolated, dried over anhydrous magnesium sulphate, filtered and concentrated to give the sub-titled compound (0.13 g) as a viscous oil.

m/e 340.0 (M+H)$^+$

¹H NMR (400 MHz, CDCl₃) δ 9.42 (s, 1H), 7.33-7.14 (m, 10H), 3.92 (s, 2H), 3.78-3.57 (m, 6H), 2.90-2.81 (m, 4H), 2.53 & 2.40 (t, 2H).

c) N-[2-[2-(4-Hydroxy-2-oxo-3H-benzothiazol-7-yl) ethylamino]ethyl]-N-phenethyl-3-phenethyloxy-propanamide N-(2-Oxoethyl)-N-phenethyl-3-phenethyloxy-propanamide (Example 3b), 0.13 g) was dissolved in methanol (6 mL) and treated with 7-(2-aminoethyl)-4-hydroxy-1,3-benthiazol-2(3H)-one hydrobromide (0.1 g), sodium cyanoborohydride (0.014 g), acetic acid (3 drops) and water (10 drops) at ambient temperature. The resultant mixture was stirred at ambient temperature overnight. Ammonia (7N in methanol, 5 drops) was then added and the mixture concentrated. The collected residue was purified by reverse phase HPLC (0.2% trifluoroacetic acid:acetonitrile 75:05 gradient elution on an "Xterra" (trade mark) column) to give the titled compound (20 mg) as a glass like solid.
m/e 534 (M+H)⁺
¹H NMR (400 MHz, CDOD₃) δ 11.73 (s, 1H), 10.16 (s, 1H), 8.65 (bs, 1H), 7.34-7.18 (m, 10H), 6.85 (d, 1H), 6.75 (d, 1H), 3.68-3.51 (m, 8H), 3.09 (bs, 4H), 2.80-2.75 (m, 6H), 2.47-2.42 (m, 2H).

EXAMPLE 4

N-Benzyl-N-[2-[2-(4-hydroxy-2-oxo-3H-benzothiazol-7-yl)ethylamino]ethyl]-3-phenethyloxy-propanamide

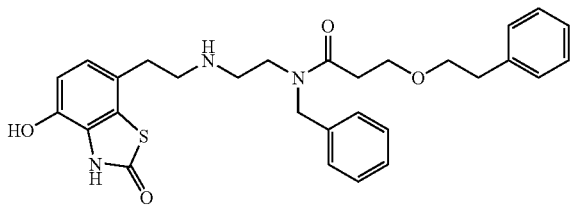

a) N-Benzyl-N-(2,2-diethoxyethyl)-3-phenethyloxy-propanamide

3-Phenethyloxypropanoic acid (0.4 g) was dissolved in dichloromethane (10 mL) and treated with oxalyl chloride (0.35 g) and a drop of dimethylformamide at ambient temperature. The resultant solution was stirred at ambient temperature for 1 hour. The solution was then concentrated and azeotroped with dichloromethane (3×10 mL). The collected residue was dissolved in dichloromethane (5 mL) and added, portionwise, to a stirred solution of N-benzyl-2,2-diethoxyethanamine (0.47 g) and N-ethyl-N-isopropyl-propan-2-amine (0.6 mL), dissolved in dichloromethane (10 mL), at ambient temperature. The resultant solution was stirred at ambient temperature for 1 hour. The mixture was then poured into ethyl acetate (25 mL), washed with water (2×25 mL), washed with brine (25 mL), dried over anhydrous magnesium sulphate, filtered and concentrated to give the sub-titled compound (0.62 g) as an oil.
m/e 400.4 (M+H)⁺
¹H NMR (400 MHz, CDCl₃) δ 7.33-7.13 (m, 110H), 4.70 (d, 2H), 4.63 & 4.44 (t, 1H), 3.83-3.62 (m, 10H), 2.88-2.86 (m, 2H), 2.76 & 2.61 (t, 2H), 1.22-1.16 (m, 6H).

b) N-Benzyl-N-(2-oxoethyl)-3-phenethyloxy-propanamide

N-Benzyl-N-(2,2-diethoxyethyl)-3-phenethyloxy-propanamide (Example 4a), 0.3 g) was dissolved in anhydrous dioxane (7 mL) and treated with concentrated hydrochloric acid (2 mL) at ambient temperature. The resultant solution was stirred at ambient temperature for 2.5 hours. The reaction mixture was poured into dichloromethane (20 mL) and washed with water (2×20 mL) and brine (20 mL). The organic layer was isolated, dried over anhydrous magnesium sulphate, filtered and concentrated to give the sub-titled compound (0.19 g) as a viscous oil.
m/e 326 (M+H)⁺
¹H NMR (400 MHz, CDCl₃) δ 7.38-7.17 (m, 100H), 4.59 & 4.65 (s, 2H), 4.03 (s, 2H), 3.82 (t, 2H), 3.70 (under solvent peak, m, 2H), 2.92-2.84 (m, 2H), 2.75 & 2.62 (t, 2H), c) N-Benzyl-N-[2-[2-(4-hydroxy-2-oxo-3H-benzothiazol-7-yl)ethylamino]ethyl]-3-phenethyloxy-propanamide N-Benzyl-N-(2-oxoethyl)-3-phenethyloxy-propanamide (Example 4b), 0.19 g) was dissolved in methanol (8 mL) and treated with 7-(2-aminoethyl)-4-hydroxy-1,3-benthiazol-2 (3H)-one hydrobromide (0.14 g), sodium cyanoborohydride (0.022 g), acetic acid (5 drops) and water (20 drops) at ambient temperature. The resultant mixture was stirred at ambient temperature overnight. Ammonia (7N in methanol, 5 drops) was then added and the mixture was concentrated. The collected residue was dissolved in methanol (2 mL) and purified by reverse phase HPLC (0.2% trifluoroacetic acid:acetonitrile 75:05 gradient elution on an "Xterra" (trade mark) column) to give the titled compound (120 mg) as a white solid.
m/e 534 (M+H)⁺
¹H NMR (400 MHz, CDCl₃) δ 7.42-7.15 (m, 10H), 6.92 (d, 1H), 6.78 (d, 1H), 4.66 (s, 2H), 3.85-3.62 (m, 6H), 3.26-3.12 (m, 4H), 2.96-2.84 (m, 4H), 2.71 & 2.54 (t, 2H).

EXAMPLE 5

N-[2-[2-(4-Hydroxy-2-oxo-3H-benzothiazol-7-yl) ethylamino]ethyl]-3-phenethyloxy-N-(3-pyridylmethyl)propanamide

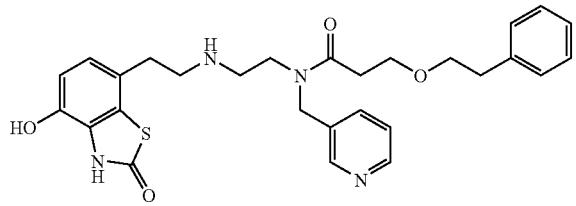

a) N-(2,2-Diethoxyethyl)-3-phenethyloxy-N-(3-pyridylmethyl)propanamide

3-Phenethyloxypropanoic acid (0.15 g) was dissolved in dichloromethane (4 mL) and treated with oxalyl chloride (0.13 g) and a drop of dimethylformamide at ambient temperature. The resultant solution was stirred at ambient temperature for 1 hour. The solution was then concentrated and azeotroped with dichloromethane (3×4 mL). The collected residue was dissolved in dichloromethane (4 mL) and added to a stirred solution of 2,2-diethoxy-N-(3-pyridylmethyl) ethanamine (0.17 g) and N-ethyl-N-isopropyl-propan-2-amine (0.25 mL), dissolved in dichloromethane (3 mL), at ambient temperature. The resultant solution was stirred at ambient temperature for 1 hour. The mixture was then poured into ethyl acetate (15 mL), washed with water (2×15 mL), washed with brine (15 mL), dried over anhydrous magnesium sulphate, filtered and concentrated to give the sub-titled compound (0.2 g) as a viscous oil.

m/e 401.2 (M+H)$^+$ $^1$H NMR (400 MHz, CDCl$_3$) δ 8.55-8.46 (m, 2H), 7.64 (d, 1H), 7.26-7.18 (m, 6H), 4.72 (s, 2H), 4.62 & 4.50 (t, 1H), 3.84-3.34 (m, 10H), 2.90-2.84 (m, 2H), 2.76-2.72 & 2.62-2.58 (m, 2H), 1.24-1.19 (m, 6H).

b) N-(2-Oxoethyl)-3-phenethyloxy-N-(3-pyridylmethyl)propanamide

N-(2,2-Diethoxyethyl)-3-phenethyloxy-N-(3-pyridylmethyl)propanamide (Example 5a), 0.086 g) was dissolved in anhydrous dioxane (3 mL) and treated with concentrated hydrochloric acid (0.6 mL) at ambient temperature. The resultant solution was stirred at ambient temperature for 2.5 hours. The reaction mixture was then poured into dichloromethane (10 mL) and basified with saturated sodium bicarbonate. The organic layer was isolated, washed with water (2×10 mL), washed with brine (10 mL), dried over anhydrous magnesium sulphate, filtered and concentrated to give the sub-titled compound that was used in the next step without further purification.

m/e 327.3 (M+H)$^+$ c) N-[2-[2-(4-Hydroxy-2-oxo-3H-benzothiazol-7-yl)ethylamino]ethyl]-3-phenethyloxy-N-(3-pyridylmethyl)propanamide N-(2-Oxoethyl)-3-phenethyloxy-N-(3-pyridylmethyl)propanamide (Example 5b), 0.04 g) was dissolved in methanol (3 mL) and treated with 7-(2-aminoethyl)-4-hydroxy-1,3-benthiazol-2(3H)-one hydrobromide (0.03 g), sodium cyanoborohydride (0.005 g), acetic acid (3 drops) and water (8 drops) at ambient temperature. The resultant mixture was stirred at ambient temperature overnight. Ammonia (7N in methanol, 5 drops) was then added and the mixture was concentrated. The collected residue was purified by reverse phase HPLC (0.2% trifluoroacetic acid:acetonitrile 75:05 gradient elution on an "Xterra" (trade mark) column) to give the titled compound (4 mg) as a white solid.

m/e 521.2 (M+H)$^+$ $^1$H NMR (400 Hz, CDCl$_3$) δ 8.53 (bs, 2H), 7.66 (bs, 1H), 7.38 (bs, 1H), 7.24-7.22 (m, 5H), 6.87-6.85 (m, 1H), 6.79-6.76 (m, 1H), 4.64 (bs, 2H), 3.72-3.63 (4H, under H$_2$O peak), 3.22-3.14 (m, 6H), 2.87-2.81 (m, 4H), 2.67 (bs, 2H).

EXAMPLE 6

N-[2-[2-(4-Hydroxy-2-oxo-3H-benzothiazol-7-yl)ethylamino]ethyl]-3-phenethyloxy-N-phenyl-propanamide

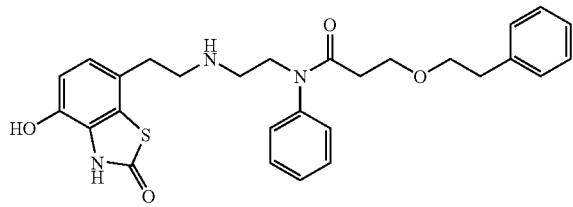

a) N-(2,2-Diethoxyethyl)-3-phenethyloxy-N-phenyl-propanamide

3-Phenethyloxypropanoic acid (0.25 g) was dissolved in dichloromethane (8 mL) and treated with oxalyl chloride (0.22 g) and a drop of dimethylformamide at ambient temperature. The resultant solution was stirred at ambient temperature for 1 hour. The solution was then concentrated and azeotroped with dichloromethane (3×8 mL). The collected residue was dissolved in dichloromethane (8 mL) and added to a stirred solution of N-(2,2-diethoxyethyl)aniline (0.27 g) and N-ethyl-N-isopropyl-propan-2-amine (0.4 mL), dissolved in dichloromethane (4 mL), at ambient temperature. The resultant solution was stirred at ambient temperature for 1 hour. The mixture was then poured into ethyl acetate (25 mL), washed with water (2×25 mL), washed with brine (25 mL), dried over anhydrous magnesium sulphate, filtered and concentrated. The collected residue was purified by flash chromatography eluting with 1:6 ethylacetate:iso-hexane to yield the sub-titled compound (0.18 g) as an oil.

m/e 386.4 (M+H)$^+$ $^1$H NMR (400 MHz, CDCl$_3$) δ 7.38-7.17 (m, 10H), 4.79 (t, 1H), 3.78 (d, 2H), 3.70 (t, 2H), 3.67-3.53 (m, 4H), 3.52-3.48 (m, 2H), 2.84 (t, 2H), 2.33 (t, 2H), 1.16 (t, 6H).

b) N-(2-Oxoethyl)-3-phenethyloxy-N-phenyl-propanamide

N-(2,2-Diethoxyethyl)-3-phenethyloxy-N-phenyl-propanamide (Example 6a), 0.11 g) was dissolved in anhydrous dioxane (5 mL) and cooled to 0° C. Concentrated hydrochloric acid (0.3 mL) was added dropwise to the stirred solution at 0° C. The resultant reaction mixture was stirred at 0° C. for 2 hours. The reaction mixture was then poured into dichloromethane (10 mL) and washed with water (2×10 mL) and brine (10 mL). The organic layer was isolated, dried over anhydrous magnesium sulphate, filtered and concentrated to give the sub-titled compound (0.07 g) as a viscous oil.

m/e 312.5 (M+H)$^+$ $^1$H NMR (400 MHz, CDCl$_3$) δ 9.62 (s, 1H), 7.42-7.18 (m, 10H), 4.40 (s, 2H), 3.69 (t, 2H), 3.61 (t, 2H), 2.85 (t, 2H), 2.43 (t, 2H).

c) N-[2-[2-(4-Hydroxy-2-oxo-3H-benzothiazol-7-yl)ethylamino]ethyl]-3-phenethyloxy-N-phenyl-propanamide N-(2-Oxoethyl)-3-phenethyloxy-N-phenyl-propanamide (Example 6b), 0.06 g) was dissolved in methanol (3 mL) and treated with 7-(2-aminoethyl)-4-hydroxy-1,3-benthiazol-2(3H)-one hydrobromide (0.047 g), sodium cyanoborohydride (0.005 g), acetic acid (3 drops) and water (15 drops) at ambient temperature. The resultant mixture was stirred at ambient temperature overnight. Ammonia (7N in methanol, 5 drops) was then added and the mixture was concentrated. The collected residue was purified by reverse phase HPLC (0.2% ammonia:acetonitrile 95:05 gradient elution on an "Xterra" (trade mark) column) to give the titled compound (20 mg) as a solid.

m/e 506.5 (M+H)$^+$ $^1$H NMR (400 MHz, CDCl$_3$) δ 7.40-7.36 (m, 3H), 7.26-7.07 (m, 7H), 6.81 (d, 1H), 6.70 (d, 1H), 3.81 (t, 2H), 3.62-3.54 (m, 4H), 2.82-2.78 (m, 4H), 2.72-2.69 (m, 4H), 2.22 (t, 2H).

EXAMPLE 7

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide

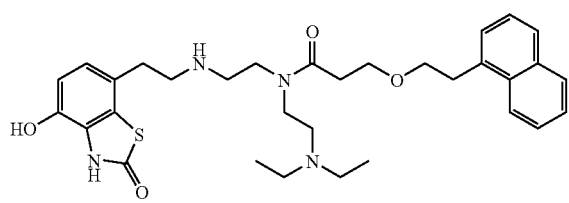

a) tert-Butyl 3-[(2-(1-naphthyl)ethoxy]propanoate

1-Naphthalene ethanol (10 g) was treated with benzyltrimethylammonium hydroxide (Triton B®; 0.9 mL of a 40% solution in methanol) and the resulting mixture stirred in vacuo for 30 minutes. The mixture was then cooled to 0° C. and treated with tert-butyl acrylate (8.19 g). The resulting mixture was slowly warmed to room temperature and stirred overnight. The crude mixture was subsequently absorbed onto aluminium oxide (30 g) and eluted with diethylether (200 mL). The organics were concentrated to give a crude material (16.6 g) which was purified by flash silica chromatography eluting with 1:8, diethylether:hexane to give the subtitled compound (12.83 g).

$^1$H NMR (300 MHz, CDCl$_3$) δ 8.05 (dd, 1H), 7.84 (dd, 1H), 7.72 (dd, 1H), 7.54-7.34 (m, 4H), 3.81-3.69 (m, 4H), 3.35 (t, 2H), 2.52-2.47 (m, 2H), 1.45 (s, 9H).

b) 3-[2-(1-Naphthyl)ethoxy]propanoic acid tert-Butyl 3-[2-(1-naphthyl)ethoxy]propanoate (Example 7a), 6.19 g) was taken up in dichloromethane (30 mL) and treated with trifluoroacetic acid (5 mL). The resulting solution was stirred at room temperature for 2 hours, an additional 1 mL of trifluoroacetic acid was added and the solution stirred overnight. The mixture was concentrated, taken up in 2M sodium hydroxide solution (30 mL) and washed with ether (2×20 mL). The aqueous layer was subsequently acidified (using 1M hydrochloric acid) and extracted with ether (2×30 mL). The combined organics were washed with brine (20 mL), dried over anhydrous magnesium sulphate, filtered and concentrated in vacuo to give the sub-titled compound (5.66 g) as a clear oil.

$^1$H NMR (300 MHz, CDCl$_3$) δ 8.05 (bs, 1H), 7.85 (bs, 1H), 7.74 (bs, 1H), 7.50-7.38 (m, 4H), 3.84-3.75 (bm, 4H), 3.39 (bs, 2H), 2.65 (bs, 2H).

c) N-(2-Diethylaminoethyl)-N-(2-hydroxyethyl)-3-[2-(1-naphthyl)ethoxy]-propanamide Oxalyl chloride (0.33 g) was added dropwise to a solution of 3-[2-(1-naphthyl)ethoxy]propanoic acid (Example 7b), 0.53 g) in dichloromethane (10 mL), dimethylformamide (1 drop) was added and stirring continued at room temperature for 1 hour. The mixture was subsequently concentrated, redissolved in dichloromethane (10 mL) and added dropwise to a solution of 2-(2-diethylaminoethylamino)ethanol (0.35 g) and diisopropylethylamine (0.56 g) in dichloromethane (10 mL). The resulting mixture was stirred at room temperature for 1 hour, diluted (dichloromethane, 50 mL), washed with water (2×20 mL), brine (20 mL), dried over magnesium sulfate and concentrated to give the crude product (0.91 g) which was purified by flash column chromatography (eluting with 5-7% methanol in dichloromethane) to give 0.63 g of the sub-titled compound.

$^1$H NMR (400 MHz, CDCl$_3$) δ 8.05 (d, 1H), 7.85 (d, 1H), 7.73 (d, 1H), 7.52-7.47 (m, 2H), 7.42-7.35 (m, 2H), 3.84-3.78 (m, 6H), 3.72-3.70 (m, 1/2H), 3.45-3.35 (m, 6H), 2.79-2.77 (m, 1+1/2H), 2.62-2.58 (m, 2H), 2.54-2.49 (m, 4H), 1.04-1.01 (m, 6H).

d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide A solution of dimethylsulfoxide (0.097 g) in dichloromethane (1 mL) was added to a solution of oxalyl chloride (0.079 g) in dichloromethane (10 mL) at −78° C. The reaction was stirred for 15 minutes and then a solution of N-(2-diethylaminoethyl)-N-(2-hydroxyethyl)-3-[2-(1-naphthyl)ethoxy]propanamide (0.22 g) in dichloromethane (1 mL+1 mL wash) was added and the reaction mixture stirred for a further 15 minutes. Triethylamine (0.29 g) was added and the reaction allowed to warm to room temperature over 1 hour, the mixture was subsequently diluted (dichloromethane 30 mL), the organics washed with sodium bicarbonate (20 mL), brine (20 mL), dried over anhydrous magnesium sulphate, filtered and concentrated in vacuo to give the sub-titled compound (0.21 g).

The crude product was dissolved in methanol (10 mL) and 7-(2-aminoethyl)-4-hydroxy-1,3-benthiazol-2(3H)-one hydrochloride (prepared according to the procedure outlined in Organic Process Research & Development 2004, 8(4), 628-642; 0.131 g) was added along with acetic acid (0.1 mL) and water (0.1 mL). After stirring at room temperature for 30 minutes, sodium cyanoborohydride (0.020 g) was added and the reaction mixture was stirred overnight. Ammonia (7N in methanol, 1 mL) was added and the mixture was concentrated. The crude residue was purified by flash column chromatography eluting with 1% ammonia; 5%-7% methanol in dichloromethane. The isolated product was dissolved in dichloromethane and treated with 4N hydrogen chloride in 1,4-dioxane (0.5 mL) and concentrated. The oily residue obtained was triturated with ether and then concentrated once the ether had been decanted to yield the titled compound as a white solid (0.089 g).

m/e 579 (M+H)$^+$ $^1$H NMR (400 MHz, CDCl$_3$, mixture of rotamers) δ 8.03 (d, 1H), 7.82 (d, 1H), 7.70 (d, 1H), 7.49-7.45 (m, 2H), 7.39-7.34 (m, 2H), 6.74-6.69 (m, 1H), 6.47 (d, 1/2H), 6.40 (d, 1/2H), 3.84-3.78 (m, 4H), 3.51-3.49 (m, 2H), 3.39-3.31 (m, 4H), 2.97-2.92 (m, 2H), 2.79 and 2.73 (2×t, 2H), 2.68-2.57 (m, 6H), 2.52-2.47 (m, 4H), 0.98 and 1.02 (2×t, 6H).

EXAMPLE 8

N-(3-{[2-(4-Hydroxy-2-oxo-2,3-dihydro-1,3-benzothiazol-7-yl)ethyl]amino}propyl)-3-(2-phenylethoxy)-N-(2-phenylethyl)propanamide

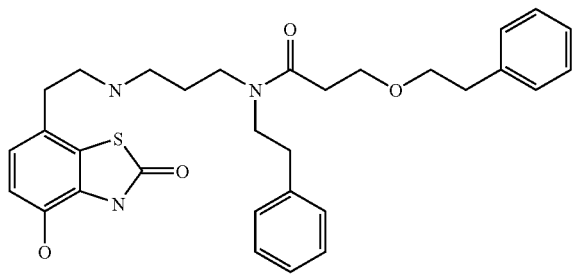

a) 3,3-Diethoxy-N-phenethyl-propan-1-amine 3,3-Diethoxypropan-1-amine (0.20 g) dissolved in ethanol (10 mL) was treated with 2-phenylacetaldehyde (0.163 g) and acetic acid (0.02 mL). The resulting mixture was stirred at room temperature for 15 minutes and treated with sodium cyanoborohydride (0.051 g). After 14 hours the mixture was concentrated, taken up in ethyl acetate (30 mL) washed with saturated sodium bicarbonate (20 mL), brine (20 mL), dried over anhydrous magnesium sulphate, filtered and concentrated under reduced pressure to give a crude sample of the sub-titled compound (0.33 g).

b) N-(3,3-Diethoxypropyl)-N-phenethyl-3-phenethyloxy-propanamide

Oxalyl chloride (0.078 g) was added dropwise to a solution of 3-phenethyloxypropanoic acid (0.10 g) in dichloromethane (10 mL), dimethyl formamide (1 drop) was added and stirring continued at room temperature for 1 hour. The mixture was subsequently concentrated, redissolved in dichloromethane (10 mL) and added dropwise to a solution of the crude 3,3-diethoxy-N-phenethyl-propan-1-amine, prepared as described in Example 8a) (0.33 g), and diisopropylethylamine (0.37 g) in dichloromethane (10 mL). The resulting mixture was stirred at room temperature for 1 hour, diluted (dichloromethane, 50 mL), washed with water (2×20 mL), brine (20 mL), dried over magnesium sulfate and concentrated to give a crude product (0.32 g). The latter was purified by passing through a plug of SCX resin, eluting with methanol (100 mL) to give the sub-titled compound as a clear oil (0.127 g).

c) N-(3-Oxopropyl)-N-phenethyl-3-phenethyloxy-propanamide

A solution of N-(3,3-diethoxypropyl)-N-phenethyl-3-phenethyloxy-propanamide (Example 8b), 0.127 g) in dioxane (10 mL) was treated with concentrated hydrochloric acid (1 mL) and stirred at room temperature for 30 minutes. After this time the solution was diluted (dichloromethane 30 mL), washed with water (2×20 mL), brine (20 mL), dried over magnesium sulfate and concentrated to give the crude aldehyde product (0.13 g) which was used immediately. The crude aldehyde was dissolved in methanol (20 mL) and 7-(2-aminoethyl)-4-hydroxy-3H-benzothiazol-2-one hydrochloride (0.078 g) was added along with acetic acid (0.1 mL) and water (0.1 mL). After stirring at room temperature for 30 minutes, sodium cyanoborohydride (0.012 g) was added and the reaction mixture stirred overnight. Ammonia (7N in methanol, 1 mL) was added and the mixture was concentrated. The resulting residue was taken up in ethyl acetate (50 mL), washed with water (2×20 mL), brine (20 mL), dried over magnesium sulfate and concentrated to give the crude product which was purified by flash column chromatography eluting with 1% ammonia; 5% methanol in dichloromethane to afford the titled compound as a white solid (0.078 g).

m/e 548 (M+H+, 100%)

$^1$H NMR (400 MHz, mixture of rotamers, CDCl$_3$) δ 7.30-7.10 (m, 10H), 6.75 (d, 1/3H), 6.69 (d, 2/3H), 6.61 (d, 1/3H), 6.48 (d, 2/3H), 3.79-3.39 (m, 10H), 3.16 (t, 1/2H), 2.93-2.79 (m, 4H), 2.75-2.68 (m, 2H), 2.61-2.55 (m, 2H), 2.41 (t, 1+1/2H), 1.74 (t, 1+1/2H), 1.64 (t, 1/2H).

EXAMPLE 9

N-[2-[2-(4-Hydroxy-2-oxo-3H-benzothiazol-7-yl)ethylamino]ethyl]-3-phenethyloxy-N-(5-phenethyloxypentyl)propanamide

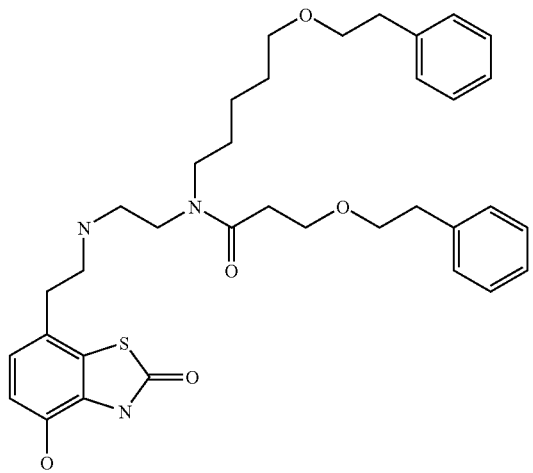

a) N-(2,2-Diethoxyethyl)-5-phenethyloxy-pentan-1-amine 2-(5-Bromopentoxy)ethylbenzene (1.5 g) was dissolved in ethanol (30 mL) and treated with 2,2-diethoxyethylamine (0.86 g) and diisopropylethylamine (1.8 mL) at room temperature. The reaction was stirred at 78° C. for 48 hours and was then poured into ethyl acetate (10 mL), washed with water (10 mL) and brine (10 mL). The organic layer was dried over anhydrous magnesium sulphate, filtered and concentrated in vacuo to give the sub-titled compound (0.2 g) as an oil.

m/e 324.5 [M+H]+

$^1$H NMR (400 MHz, CDCl$_3$) δ 7.31-7.18 (m, 5H), 4.60 (t, 1H), 3.73-3.67 (m, 2H), 3.64-3.53 (m, 4H), 3.44 (t, 2H), 2.88 (t, 2H), 2.73 (d, 2H), 2.61 (t, 2H), 1.62-1.55 (m, 2H), 1.53-1.45 (m, 2H), 1.39-1.33 (m, 2H), 1.22 (t, 6H).

b) N-(2,2-Diethoxyethyl)-3-phenethyloxy-N-(5-phenethyloxypentyl)propanamide

3-Phenethyloxypropanoic acid (0.1 g) was dissolved in dichloromethane (3 mL) and treated with oxalyl chloride (0.09 g) and a drop of dimethylformamide at room temperature. The resultant solution was stirred at room temperature for 1.5 hours. The solution was then concentrated and azeotroped with dichloromethane (2×3 mL). The collected residue was dissolved in dichloromethane (3 mL) and added, dropwise to a stirred solution of N-(2,2-diethoxyethyl)-5-phenethyloxy-pentan-1-amine (Example 9a), 0.17 g) and diisopropylamine (0.16 mL) dissolved in dichloromethane (2 mL). The resultant solution was stirred at room temperature for 2.5 hours and was then concentrated, taken up in ethyl acetate (15 mL), washed with water (2×15 mL), brine (15 mL), dried over anhydrous magnesium sulphate, filtered and concentrated to give the sub-titled compound (0.2 g) as an oil.

m/e 500.5[M+H]$^+$ $^1$H NMR (400 MHz, CDCl$_3$, rotamers present) δ 7.28-7.19 (m, 10H), 4.65 & 4.55 (t, 1H), 3.80-3.35 (m, 16H), 2.90-2.86 (m, 4H), 2.67 & 2.59 (t, 2H), 1.62-1.55 (m, 4H), 1.28-1.18 (m, 8H).

c) N-(2-Oxoethyl)-3-phenethyloxy-N-(5-phenethyloxypentyl)propanamide

N-(2,2-Diethoxyethyl)-3-phenethyloxy-N-(5-phenethyloxypentyl)propanamide (Example 9b), 0.18 g) was dissolved in anhydrous dioxane (5 mL) and treated with concentrated hydrochloric acid (5 mL) at room temperature. The resultant solution was stirred for 1 hour and then poured into dichloromethane (10 mL), washed with water (2×10 mL) and brine (10 mL). The organic layer was isolated, dried over anhydrous magnesium sulphate, filtered and concentrated to give the sub-titled compound (0.12 g) as a viscous oil.

m/e 424.5 [M−H]$^+$ $^1$H NMR (400 MHz, CDCl$_3$, rotamers present) δ 9.46 (s, 1H), 7.30-7.27 (m, 5H), 7.22-7.18 (m, 5H), 3.98 (s, 2H), 3.80-3.60 (m, 6H), 3.42 (t, 2H), 3.29 (t, 2H), 2.89-2.85 (t, 4H), 2.65 & 2.40 (t, 2H), 1.60-1.50 (m, 4H), 1.34-1.25 (m, 2H).

d) N-[2-[2-(4-Hydroxy-2-oxo-3H-benzothiazol-7-yl)ethylamino]ethyl]-3-phenethyloxy-N-(5-phenethyloxypentyl)propanamide N-(2-Oxoethyl)-3-phenethyloxy-N-(5-phenethyloxypentyl)propanamide (Example 9c), 0.12 g) was dissolved in methanol (5 mL) and treated with 7-(2-aminoethyl)-4-hydroxy-3H-benzothiazol-2-one hydrochloride (0.32 g), acetic acid (0.1 mL) and water (0.3 mL). The resultant mixture was stirred for 2 hours and then sodium cyanoborohydride (0.01 g) was added and the reaction mixture was stirred overnight. The mixture was concentrated in vacuo and the residue was taken up in methanol (5 mL) and adsorbed onto silica gel. The product was purified by flash chromatography eluting with 5% methanol, 1% ammonia in dichloromethane. Collected fractions were concentrated and the resultant residue was taken up in dichloromethane (5 mL) and treated with 4N hydrogen chloride in dioxane (0.2 mL). The mixture was stirred vigorously and concentrated. The resulting gum was azeotroped with dichloromethane (3×5 mL) to give the titled compound (0.13 g) as a white solid.

me 620.5 [M+H]$^+$ $^1$H NMR (400 MHz, CDCl$_3$) δ 7.24-7.17 (m, 10H), 6.94 (d, 1H), 6.77 (d, 1H), 3.69 (t, 2H), 3.64-3.60 (m, 6H), 3.44 (t, 2H), 3.32-3.29 (m, 2H), 3.21-3.15 (m, 4H), 2.90-2.85 (m, 2H), 2.83-2.81 (m, 4H), 2.59 (t, 2H), 1.60-1.52 (m, 4H), 1.37-1.26 (m, 2H).

EXAMPLE 10

3-[2-(4-Bromophenyl)ethoxy]-N-[2-[2-(4-hydroxy-2-oxo-3H-benzothiazol-7-yl)ethylamino]ethyl]-N-phenethyl-propanamide

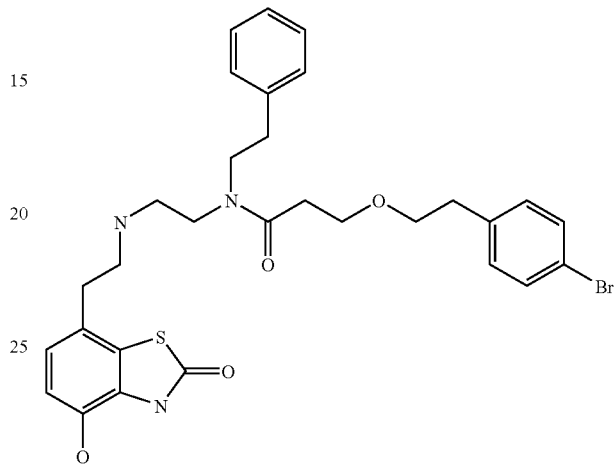

a) tert-Butyl 3-[2-(4-bromophenyl)ethoxy]propanoate 2-(4-Bromophenyl)ethanol (5 g) was treated with benzyltrimethylammonium hydroxide (Triton B®) (0.3 mL) and the resultant mixture was stirred in vacuo for 30 minutes. The mixture was then cooled to 0° C. and treated with t-butyl acrylate (3.5 g). The reaction was warmed to room temperature and stirred for 5 hours. The mixture was filtered through aluminium oxide (15 g) eluting with ether (75 mL). The collected filtrate was concentrated and purified by flash chromatography eluting with ethylacetate:iso-hexane (1:8) to give the sub-titled compound (5.42 g) as an oil.

m/e 271.3 [M+H-tBu]$^+$ $^1$H NMR (400 MHz, CDCl$_3$) δ 7.39 (d, 2H), 7.09 (d, 2H), 3.68-3.61 (m, 4H), 2.82 (t, 2H), 2.47 (t, 2H), 1.43 (s, 9H).

b) 3-[2-(4-Bromophenyl)ethoxy]propanoic Acid tert-Butyl 3-[2-(4-bromophenyl)ethoxy]propanoate (Example 10a), 1.0 g) was dissolved in dichloromethane (10 mL) and treated with trifluoroacetic acid (2.5 mL). The mixture was stirred at room temperature for 3 hours, then concentrated in vacuo and azeotroped with dichloromethane (2×10 mL). The residue was taken up in dichlormethane (10 mL) and extracted with 1M sodium hydroxide (20 mL). The basic layer was washed with dichloromethane (20 mL) then acidified with 2M hydrochloric acid. The acidic layer was extracted with dichloromethane (2×20 mL). The organic layers were combined, washed with brine, dried over anhydrous magnesium sulphate, filtered and concentrated to yield the sub-titled compound (0.81 g) as an oil.

m/e 271.6 [M−H]$^+$ $^1$H NMR (400 MHz, CDCl$_3$) δ 7.41-7.38 (m, 2H), 7.10-7.07 (m, 2H), 3.76-3.70 (m, 2H), 3.66 (t, 2H), 2.83 (t, 2H), 2.61 (t, 2H).

c) 3-[2-(4-Bromophenyl)ethoxy]-N-(2,2-diethoxy-ethyl)-N-phenethyl-propanamide 3-[2-(4-Bromophenyl)ethoxy]propanoic acid (Example 10b), 0.46 g) was dissolved in dichloromethane (10 mL) and treated with oxalyl chloride (0.28 g) and a drop of dimethylformamide. The resultant solution was stirred at room temperature for 1.5 hours. The solution was then concentrated and azeotroped with dichloromethane (2×10 mL). The residue was dissolved in dichloromethane (10 mL) and added, portionwise, to a stirred solution of 2,2-diethoxy-N-phenethyl-ethanamine (0.40 g) and diisopropylamine (0.5 mL), dissolved in dichloromethane (5 mL). The resultant solution was stirred for 2 hours, concentrated and taken up in ethyl acetate (30 mL). Washing with water (2×30 mL), and brine (30 mL) followed by drying over anhydrous magnesium sulphate, filtering and concentration gave the sub-titled compound (0.72 g) as an oil.

m/e 494.2 [M+H]$^+$ $^1$H NMR (400 MHz, CDCl$_3$, rotomers present) δ 7.40-7.36 (m, 2H), 7.30-7.26 (m, 2H), 7.22-7.15 (m, 2H), 7.12 (d, 1H), 7.08-7.05 (m, 2H), 4.65 & 4.45 (t, 1H), 3.77-3.51 (m, 10H), 3.40 & 3.26 (d, 2H), 2.85-2.79 (m, 4H), 2.66 & 2.43 (t, 2H), 1.20-1.17 (m, 6H).

d) 3-[2-(4-Bromophenyl)ethoxy]-N-(2-oxoethyl)-N-phenethyl-propanamide

3-[2-(4-Bromophenyl)ethoxy]-N-(2,2-diethoxyethyl)-N-phenethyl-propanamide (Example 10c) 0.72 g) was dissolved in anhydrous dioxane (15 mL) and treated with concentrated hydrochloric acid (10 mL) and stirred for 1 hour. The reaction mixture was then poured into dichloromethane (15 mL), washed with water (2×30 mL) and brine (30 mL). The organic layer was separated, dried over anhydrous magnesium sulphate, filtered and concentrated to give the sub-titled compound (0.54 g) as a viscous oil.

m/e 418.2 [M+H]$^+$ $^1$H NMR (400 MHz, CDCl$_3$, rotamers present) δ 9.45 (s, 1H), 7.41-7.22 (m, 5H), 7.16-7.13 (d, 2H), 7.08-7.05 (d, 2H), 3.94 (s, 2H), 3.75-3.58 (m, 6H), 2.85-2.79 (m, 4H), 2.51 & 2.39 (t, 2H), e) 3-[2-(4-Bromophenyl)ethoxy]-N-[2-[2-(4-hydroxy-2-oxo-3H-benzothiazol-7-yl)ethylamino]ethyl]-N-phenethyl-propanamide 3-[2-(4-Bromophenyl)ethoxy]-N-(2-oxoethyl)-N-phenethyl-propanamide (Example 10d), 0.54 g) was dissolved in methanol (25 mL) and treated with 7-(2-aminoethyl)-4-hydroxy-3H-benzothiazol-2-one hydrochloride (0.32 g), acetic acid (0.5 mL) and water (1.5 mL). The resultant mixture was stirred at room temperature for 2 hours and then sodium cyanoborohydride (0.05 g) was added and the reaction mixture was stirred overnight. The mixture was concentrated in vacuo and the residue was taken up in methanol (25 mL) and adsorbed onto silica gel. The adsorbed mixture was purified by flash chromatography to yield the titled compound (0.51 g) as a crystalline yellow solid.

m/e 610.4 [M+H]$^+$ $^1$H NMR (400 MHz, CDCl$_3$, rotamers present) δ 7.31-7.00 (m, 9H), 6.73-6.69 (m, 1H), 6.59 & 6.46 (d, 1H), 3.75-3.58 (m, 4H), 3.50-3.47 (m, 4H), 2.97 & 2.91 (t, 2H), 2.83-2.68 (m, 8H), 2.60 & 2.42 (t, 2H).

EXAMPLE 11

N-{2-[2-(4-Hydroxy-2-oxo-2,3-dihydro-benzothiazol-7-yl)-ethylamino]-ethyl}-3-phenethyloxy-N-piperidin-4-yl propanamide

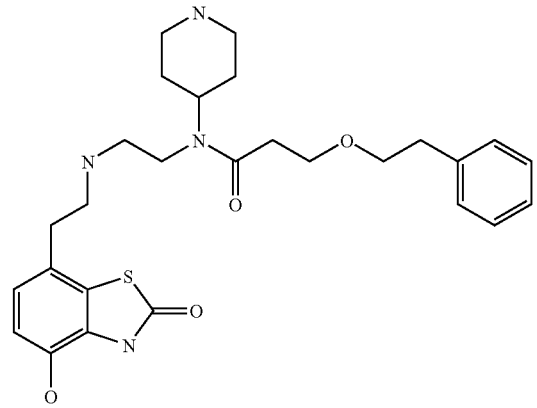

a) tert-Butyl 4-[(2-hydroxyethyl)amino]piperidine-1-carboxylate

A slurry of 10% palladium on charcoal (catalytic) in dry ethanol (3 mL) and acetic acid (5 drops) was added to a solution of ethanolamine (0.24 mL) and tert-butyl 4-oxopiperidine-1-carboxylate (0.80 g) in dry ethanol (10 mL) and hydrogenated at 2 bar for 26 hours. The solution was filtered through a glass fibre filter and the filtrate concentrated in vacuo to give the sub-titled compound (0.98 g) as a pale yellow oil.

$^1$H NMR (300 MHz, CDCl$_3$) δ 4.05 (d, 1H), 3.61 and 3.18 (2×t, 3H), 3.64-3.56 and 3.45-3.36 (2×m, 1H), 2.84-2.74 (m, 3H), 2.69-2.60 and 2.46-2.42 (2×m, 1H), 2.42 (br. s, 4H), 1.90-1.86 and 1.65-1.62 (2×m, 2H), 1.49 (9H, s).

b) tert-Butyl 4-{(2-hydroxyethyl)[3-(2-phenylethoxy)propanoyl]amino}piperidine-1-carboxylate 3-Phenethyloxypropanoic acid (0.779 g) was dissolved in dichloromethane (10 mL) and treated with oxalyl chloride (0.69 mL). The resultant solution was stirred at room temperature for 1 hour. The solution was then concentrated and azeotroped with dichloromethane (3×4 mL). The residue was dissolved in dichloromethane (4 mL) and added, portionwise, to a stirred solution of tert-butyl 4-[(2-hydroxyethyl)amino]piperidine-1-carboxylate (Example 11a), 0.95 g) and triethylamine (1.39 mL) dissolved in dichloromethane (30 mL). The resultant solution was stirred for 20 hours. The mixture was washed with 2M hydrochloric acid (2×10 mL) and then brine (15 mL), dried over anhydrous magnesium sulphate, filtered and concentrated to give a pale yellow oil. Purification by flash silica chromatography eluting with a gradient of 0-4% methanol in dichloromethane gave the sub-titled compound (0.93 g) as a colourless oil.

¹H NMR (300 MHz, CDCl₃) δ 7.31-7.19 (m, 5H), 4.52-4.43 (m, 1H), 4.18-4.05 (br.m, 2H), 4.05-3.95 (m, 2H), 3.86 (q, 3H), 3.73-3.61 (m, 4H), 3.47-3.37 (m, 2H), 2.91-2.86 (m, 2H), 2.69-2.59 (m, 4H), 1.67-1.59 (m, 4H), 1.57 (s, 9H).

c) tert-Butyl 4-{(2-{[2-(4-hydroxy-2-oxo-2,3-dihydro-1,3-benzothiazol-7-yl)ethyl]amino}ethyl) [3-(2-phenylethoxy)propanoyl]amino}piperidine-1-carboxylate A solution of dimethyl sulfoxide (0.090 mL) in dichloromethane (10 mL) was cooled to −78° C. and oxalyl chloride (0.12 mL) was added. The reaction was stirred for 15 minutes and then a solution of tert-butyl 4-{(2-hydroxyethyl)[3-(2-phenylethoxy)propanoyl]-amino}piperidine-1-carboxylate (Example 11b), 0.50 g) in dichloromethane (10 mL) was added and the reaction mixture was stirred for a further 15 minutes. Triethylamine (0.34 mL) was added and stirred at −78° C. for 15 minutes. The reaction mixture was allowed to warm to room temperature over 1 hour. The reaction mixture was washed with saturated sodium bicarbonate solution (20 mL), then brine (2×20 mL), dried with anhydrous magnesium sulfate, filtered and concentrated in vacuo. The crude product was dissolved in methanol (20 mL) and 7-(2-amino-ethyl)-4-hydroxy-3H-benzothiazol-2-one hydrochloride (0.27 g) was added along with acetic acid (0.1 mL) and water (0.15 mL). After stirring at room temperature for 45 minutes, sodium cyanoborohydride (0.045 g) was added and the reaction mixture was stirred overnight. Ammonia (7N in methanol, 1 mL) was added and the reaction mixture was concentrated onto silica gel. The residue was purified by flash column chromatography eluting with 0.7N ammonia in methanol (1-6%) in dichloromethane to give the sub-titled compound (0.21 g) as a pale yellow oil.

m/e 613 [M+H]⁺

¹H NMR (300 MHz, CDCl₃) δ 7.23-7.19 (m, 5H), 7.17-7.14 (m, 2H), 6.80 (dd, 1H), 6.60 (dd, 1H), 4.15-4.05 (m, 2H), 3.72 (quintet, 2H), 3.66 (quartet, 2H), 3.39 (brs, 2H), 3.20 (brs, 1H), 3.04-2.56 (m, 15H), 1.59-1.58 (m, 3H), 1.47 (s, 9H).

d) N-{2-[2-(4-Hydroxy-2-oxo-2,3-dihydro-benzothiazol-7-yl)-ethylamino]-ethyl}-3-phenethyloxy-N-piperidin-4-yl propanamide tert-Butyl 4-{(2-{[2-(4-hydroxy-2-oxo-2,3-dihydro-1,3-benzothiazol-7-yl)ethyl]amino}ethyl)[3-(2-phenylethoxy)propanoyl]amino}piperidine-1-carboxylate (Example 11c), 0.050 g) was stirred with 4N hydrogen chloride in dioxan (1.3 mL). After 15 minutes, methanol (1 mL) was added and the reaction mixture was stirred at room temperature overnight. Ether (5 mL) was added to give a white precipitate. The precipitate was allowed to settle, before decanting off the liquid. The residue was concentrated in vacuo, azeotroping with ether to give the title compound as a white solid (0.030 g).

m/e 513 [M+H]⁺

¹H NMR (300 MHz, d₆-DMSO, 90° C.) δ 9.75 (br.s, 1H), 9.06 (br.s, 1H), 7.28-7.13 (m, 5H), 6.89 (d, 1H), 6.75 (d, 1H), 4.08 (t, 2H), 3.65 (quintet, 4H), 3.61-3.53 (m, 2H), 3.32-3.28 (m, 2H), 3.15-3.10 (m, 5H), 3.01-2.88 (m, 4H), 2.79 (t, 2H), 2.65 (t, 2H), 2.09-2.05 (m, 2H), 1.80-1.76 (m, 2H).

EXAMPLE 12

N-[2-(Diethylamino)ethyl]-N-(2-{[2-(4-hydroxy-2-oxo-2,3-dihydro-1,3-benzothiazol-7-yl)ethyl]amino}ethyl)-3-(2-phenylethoxy)propanamide

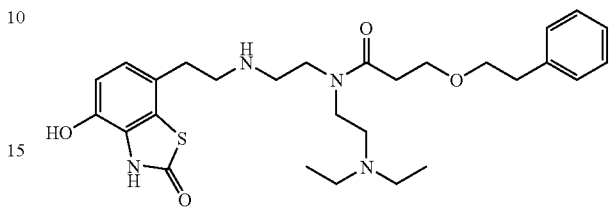

a) N-(2-Diethylaminoethyl)-N-(2-hydroxyethyl)-3-phenethyloxy-propanamide

Oxalyl chloride (0.23 g) was added dropwise to a solution of 3-phenethyloxypropanoic acid (0.32 g) in dichloromethane (10 mL), dimethylformamide (1 drop) was added and stirring continued at room temperature for 1 hour. The mixture was subsequently concentrated, redissolved in dichloromethane (101 mL) and added dropwise to a solution of 2-(2-diethylaminoethylamino)ethanol (0.26 g) and diisopropylethylamine (0.42 g) in dichloromethane (10 mL). The resulting mixture was stirred at room temperature for 1 hour, diluted (dichloromethane, 50 mL), the organics were washed with water (2×20 mL), brine (20 mL), dried over magnesium sulfate and concentrated to give the crude sub-titled product (0.39 g).

¹H NMR (400 MHz, CDCl₃) δ 7.29-7.19 (m, 5H), 3.80-3.64 (m, 6H), 3.47-3.40 (m, 4H), 2.89-2.77 (m, 4H), 2.64-2.49 (m, 6H), 1.04 (s, 6H)

b) N-[2-(Diethylamino)ethyl]-N-(2-{[2-(4-hydroxy-2-oxo-2,3-dihydro-1,3-benzothiazol-7-yl)ethyl]amino}ethyl)-3-(2-phenylethoxy)propanamide A solution of dimethyl sulfoxide (0.10 g) in dichloromethane (1 mL) was added to oxalyl chloride (0.083 g) in dichloromethane (10 mL) at −78° C. The reaction was stirred for 15 minutes and then a solution of N-(2-diethylaminoethyl)-N-(2-hydroxyethyl)-3-phenethyloxy-propanamide (Example 12a), 0.20 g) in dichloromethane (1 mL+1 mL wash) was added and the reaction mixture was stirred for a further 15 minutes. Triethylamine (0.30 g) was added and the reaction mixture was allowed to warm to room temperature over 1 hour. The mixture was subsequently diluted (dichloromethane, 30 mL), the organics washed with saturated sodium hydrogencarbonate solution (20 mL) and then brine (20 mL), dried over anhydrous magnesium sulphate, filtered and concentrated in vacuo to give a crude aldehyde product which was used immediately. The crude product was dissolved in methanol (10 mL) and 7-(2-aminoethyl)-4-hydroxy-3H-benzothiazol-2-one hydrochloride (0.15 g) added along with acetic acid (0.1 mL) and water (0.1 mL). After stirring at room temperature for 30 minutes, sodium cyanoborohydride (0.022 g) was added and the reaction mixture was stirred overnight. Ammonia (7N in methanol, 1 mL) was added and the mixture was concentrated. The crude residue was purified by flash silica column chromatography eluting with 1% ammonia; 5%-7% methanol in dichloromethane. The isolated product was dissolved in dichloromethane and treated with 4 N hydrogen chloride in 1,4-dioxane (0.5 mL) and concentrated. The oily residue was triturated with ether, decanting the ether and concentrating to afford the titled compound as a white solid (0.032 g).

m/e 529 (M+H)+

$^1$H NMR (300 MHz, CD$_3$OD) δ 7.32-7.17 (m, 5H), 6.99-6.95 (m, 1H), 6.81-6.77 (m, 1H), 3.81-3.68 (m, 6H), 3.37-3.26 (m, 12H), 3.04-2.97 (bm, 2H), 2.90-2.85 (m, 2H), 2.71-2.68 (m, 2H), 1.38-1.31 (m, 6H).

EXAMPLE 13

4-Hydroxy-7-[2-({2-[[3-(2-phenylethoxy)propyl](2-phenylethyl)amino]ethyl}amino)-ethyl]-1,3-benzothiazol-2(3H)-one

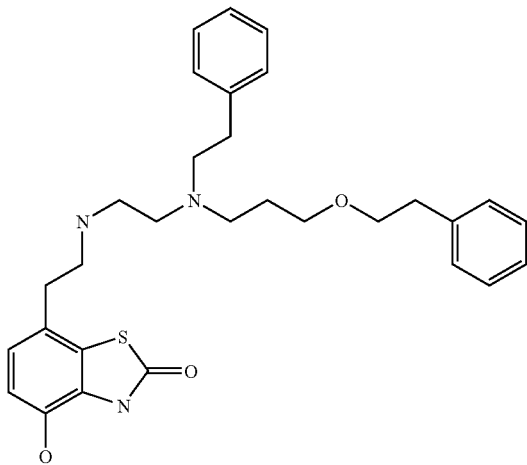

N-Benzyl-N-[2-[2-(4-hydroxy-2-oxo-3H-benzothiazol-7-yl)ethylamino]ethyl]-3-phenethyloxy-propanamide (Example 4, 0.1 g) was dissolved in tetrahydrofuran (6 mL) and treated with borane (1M in tetrahydrofuran, 1 mL) at room temperature. The resultant solution was heated at 50° C. for 3 hours. The reaction was then cooled to 0° C. and methanol (6 mL) was added dropwise. Following this, the mixture was concentrated and the collected residue was dissolved in methanol (6 mL) and treated with concentrated hydrochloric acid (1.6 mL). The acidic solution was heated at 60° C. for 14 hours, then cooled to room temperature and concentrated. The resulting residue was purified by preparative HPLC (95:05, ammonia (0.2%):acetonitrile) to give the titled compound (0.035 g) as a glass like solid.

m/e 518.3 (M−H)+

$^1$H NMR (400 MHz, CDCl$_3$) δ 7.25-7.11 (m, 10H), 6.79 (d, 1H), 6.68 (d, 1H), 3.57 (t, 2H), 3.32-3.30 (m, 2H—under MeQH peak), 2.82 (t, 2H), 2.74 (t, 2H), 2.67 (t, 2H), 2.57-2.55 (m, 8H), 2.45 (t, 2H), 1.55 (quintet, 2H).

EXAMPLE 14

N-[2-(Dimethylamino)ethyl]-N-(2-{[2-(4-hydroxy-2-oxo-2,3-dihydro-1,3-benzothiazol-7-yl)ethyl]amino}ethyl)-3-(2-phenylethoxy)propanamide

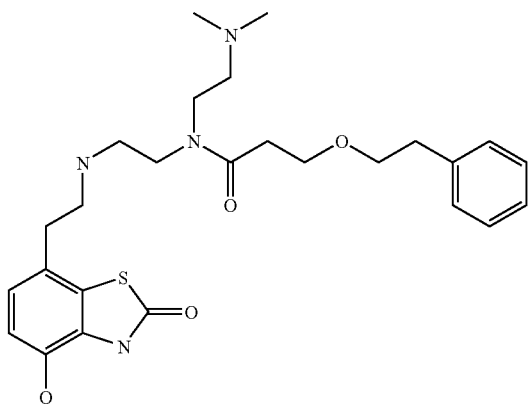

a) N-(2-Dimethylaminoethyl)-N-(2-hydroxyethyl)-3-phenethyloxy-propanamide

Oxalyl chloride (0.12 g) was added dropwise to a solution of 3-phenethyloxypropanoic acid (0.15 g) in dichloromethane (10 mL), dimethylformamide (1 drop) was added and stirring continued at room temperature for 1 hour. The mixture was subsequently concentrated, redissolved in dichloromethane (10 mL) and added dropwise to a solution of 2-(2-dimethylaminoethylamino)ethanol (0.10 g) and diisopropylethylamine (0.29 g) in dichloromethane (10 mL). The resulting mixture was stirred at room temperature for 1 hour and diluted (dichloromethane, 50 mL). The organics were washed with water (2×20 mL) and then brine (20 mL), dried over magnesium sulfate and concentrated to give the crude product (0.17 g) which was purified by flash silica column chromatography (eluting with 1% ammonia, 7% methanol in dichloromethane) to give 0.068 g of the sub-titled compound.

$^1$H NMR (400 MHz, CDCl$_3$) δ 7.30-7.18 (m, 5H), 3.81-3.65 (m, 6H), 3.55-3.41 (m, 4H), 2.87 (t, 2H), 2.67-2.26 (m, 4H), 1.26 (s, 6H)

b) N-[2-(Dimethylamino)ethyl]-N-(2-{[2-(4-hydroxy-2-oxo-2,3-dihydro-1,3-benzothiazol-7-yl)ethyl]amino}ethyl)-3-(2-phenylethoxy)propanamide A solution of dimethyl sulfoxide (0.037 g) in dichloromethane (1 mL) was added to a solution of oxalyl chloride (0.030 g) in dichloromethane (10 mL) at −78° C. The reaction was stirred for 15 minutes and then a solution of N-(2-dimethylaminoethyl)-N-(2-hydroxyethyl)-3-phenethyloxy-propanamide (Example 14a), 0.067 g) in dichloromethane (1 mL+1 mL wash) was added and the reaction stirred for a further 15 minutes. Triethylamine (0.11 g) was added and the reaction mixture was allowed to warm to room temperature over a period of 1 hour. The mixture was subsequently diluted (dichloromethane, 30 mL), the organics washed with saturated sodium hydrogencarbonate solution (20 mL) and then brine (20 mL), dried over anhydrous magnesium sulphate, filtered and concentrated in vacuo to give a crude aldehyde product which was used immediately. The crude product was dissolved in methanol (10 mL) and 7-(2-aminoethyl)-4-hydroxy-3H-benzothiazol-2-one hydrochloride (0.054 g) added along with acetic acid (0.1 mL) and water (0.1 mL). After stirring at room temperature for 30 minutes, sodium cyanoborohydride (0.014 g) was added and the reaction mixture was stirred overnight. Ammonia (7N in methanol, 1 mL) was added and the mixture was concentrated. The crude residue was purified by flash silica column chromatography eluting with 1% ammonia; 5%-7% methanol in dichloromethane to afford the titled compound as a white solid (0.012 g).

m/e 501 (M+H)$^+$ $^1$H NMR (400 MHz, CD$_3$OD) δ 7.24-7.18 (m, 5H), 6.85-6.81 (m, 1H), 6.70 (d, 1H), 3.71 (t, 2H), 3.65 (t, 2H), 3.45-3.39 (m, 4H), 2.86-2.80 (m, 4H), 2.77-2.72 (m, 4H), 2.59-2.56 (m, 2H), 2.46-2.40 (m, 2H), 2.25 (d, 6H).

EXAMPLE 15

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide

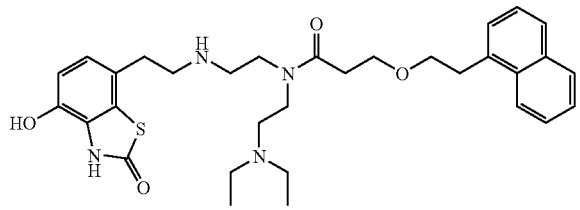

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide prepared as described in Example 7 (52 mg) was dissolved in ethanol (1.5 ml) and treated with 48% hydrobromic acid (21 μl). The white solid dihydrobromide salt was collected by filtration. Yield 58 mg.

MS: APCI (+ve) 579 (M+1)

$^1$H NMR δ$_{(DMSO)}$ 11.78-11.71 (1H, m), 10.11-10.06 (1H, m), 9.51-9.43 (0.33H, m), 9.21-9.13 (0.66H, m), 8.75-8.66 (1H, m), 8.59-8.51 (1H, m), 8.06 (1H, d), 7.95-7.90 (1H, m), 7.79 (1H, d), 7.60-7.48 (2H, m), 7.47-7.39 (2H, m), 6.87 (1H, t), 6.76 (1H, dd), 3.78-3.53 (10H, m), 3.25-3.09 (10H, m), 2.91-2.80 (2H, m), 2.73-2.61 (2H, m), 1.26-1.15 (6H, m). NMR indicates approx 2:1 mixture of rotamers at 298K.

EXAMPLE 16

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide

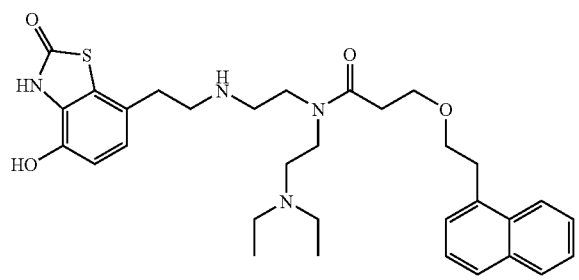

a) N'-(2,2-Dimethoxyethyl)-N,N-diethyl-ethane-1,2-diamine

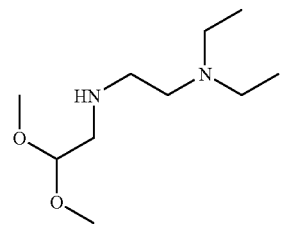

A solution of N,N-diethyl-ethylenediamine (150 g) in methanol (500 mL) was treated dropwise rapidly with glyoxal dimethylacetal (60 wt % soln. in water, 225 g) at 10-15° C. After the addition was complete the solution was warmed to 15° C., then to 22° C. and left at this temperature for 16 hr. The reaction mixture was treated with 5% palladium on carbon (Johnson-Matthey type 38H paste, 15 g) and hydrogenated at 6 bar until reaction was complete as judged by GC/MS. The catalyst was removed by filtration and the filtrate evaporated to dryness (toluene azeotrope, 2.5 L), affording 196.2 g of the sub-titled compound.

$^1$H NMR (300 MHz, CDCl$_3$): 4.48 (t, 1H), 3.39 (s, 6H), 2.75 (d, 2H), 2.69 (t, 2H), 2.57-2.48 (m, 6H), 1.01 (ts, 6H).

b) N-[2-(Diethylamino)ethyl]-N-(2,2-dimethoxyethyl)-3-[2-(1-naphthyl)ethoxy]propanamide

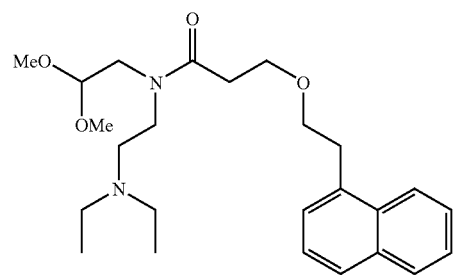

Oxalyl chloride (51 mL) was added dropwise over 45 minutes to a solution of 3-[2-(1-naphthyl)ethoxy]propanoic acid (389 g) (Example 7 step b)) in dichloromethane (2.1 L) and DMF (0.5 mL). The reaction mixture was stirred for a further 16 hours. The mixture was subsequently concentrated, redissolved in DCM (1.7 L) and added dropwise over 1.75 hours at 0° C. to a solution of N'-(2,2-dimethoxyethyl)-N,N-diethyl-ethane-1,2-diamine (325 g) and isopropyldiethylamine (551 mL) in DCM (1.7 L). The resulting mixture was stirred at room temperature for 3 hours, washed with aqueous saturated sodium bicarbonate solution (5×1 L), water (1.5 L) and dried over sodium sulphate and concentrated. Gave 650 g of the sub-titled compound.

m/e 431 (M+H$^+$, 100%)

c) N-[2-(Diethylamino)ethyl]-3-[2-(1-naphthyl)ethoxy]-N-(2-oxoethyl)propanamide

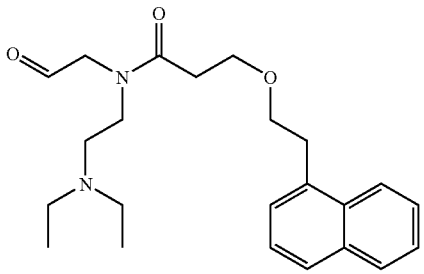

A solution of N-[2-(diethylamino)ethyl]-N-(2,2-dimethoxyethyl)-3-[2-(1-naphthyl)ethoxy]propanamide (93 g) in DCM (270 mL) was treated dropwise at 0° C. with trifluoroacetic acid (270 mL) over 1.5 hours. After the addition the reaction mixture was allowed to warm to room temperature and stirred for a further 1 hour. The reaction mixture was concentrated and the residue poured into aqueous saturated sodium bicarbonate solution (1800 mL, caution). The aqueous mixture was extracted with DCM (4×400 mL) and the combined extracts were dried over magnesium sulphate and concentrated. The residue was used directly in the following reaction.

d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide

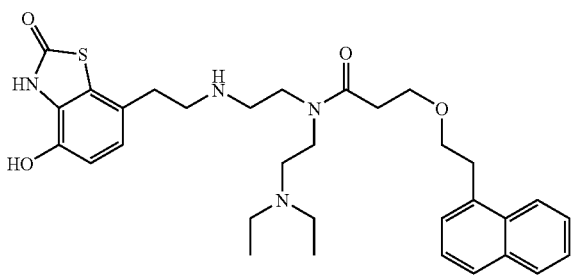

A suspension of 7-(2-amino-ethyl)-4-hydroxy-3H-benzothiazol-2-one hydrochloride (53 g) in dry NMP (216 mL) was heated to 60° C. and treated in one portion with a solution of NaOH (8.2 g) in methanol (102 mL). The bright orange suspension was cooled to room temperature and treated dropwise with a solution of N-[2-(diethylamino)ethyl]-3-[2-(1-naphthyl)ethoxy]-N-(2-oxoethyl)propanamide in dichloromethane (475 mL) over 20 minutes. The reaction was left to stir for 25 minutes. Sodium triacetoxyborohydride (91.5 g) was then added in portions over 20 minutes and the mixture then stirred for a further 50 minutes. The reaction mixture was poured into water (1.8 L) and the acidic solution (pH5) was washed with tert. butyl methyl ether (TBME) (3×500 mL). The aqueous phase was basified to pH8 by the addition of solid potassium carbonate and extracted with dichloromethane (3×750 mL); the combined organic extracts were dried over magnesium sulphate and concentrated to give a dark oil. This was dissolved in ethanol (200 mL) and 48% aqueous hydrobromic acid (73 mL) was added. The solution was aged for 30 minutes then evaporated to dryness. The residue was triturated with ethanol (560 mL); the resultant solid was collected by filtration and dried in vacuo at 50. The sticky solid was suspended in boiling ethanol (100 mL) and filtered hot; the collected solid was dried in vacuo at 50° C. This material was recrystallised from ethanol/water (3:1, 500 mL); after standing overnight the resultant solid was collected by filtration and washed with ice-cold ethanol (75 mL). Drying in vacuo at 50 C for 24 hr afforded 57 g of the title compound.

EXAMPLE 17

N-[2-(Diethylamino)ethyl]-N-(2-{[2-(4-hydroxy-2-oxo-2,3-dihydro-1,3-benzothiazol-7-yl)ethyl]amino}ethyl)-3-{2-[2-(trifluoromethyl)phenyl]ethoxy}propanamide ditrifluoroacetate

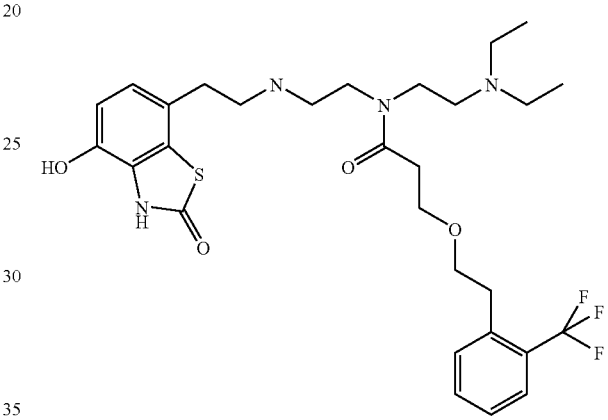

a) Benzyl N-(2,2-dimethoxyethyl)-[2-(4-hydroxy-2-oxo-2,3-dihydro-1,3-benzothiazol-7-yl)ethyl]carbamate

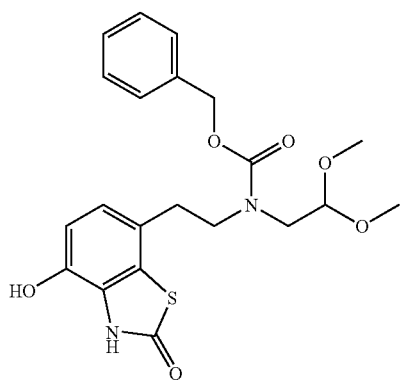

7-(2-Aminoethyl)-4-hydroxy-1,3-benzothiazol-2(3H)-one hydrochloride (5.0 g, 20.2 mmol) was dissolved in a mixture of MeOH (50 ml) and water (25 ml), NaHCO$_3$ (1.7 g, 20.2 mmol) added, followed by 60% aqueous dimethoxyacetaldehyde (3.5 ml, 20.2 mmol) and the mixture stirred for 20 min Sodium cyanoborohydride (91 mg, 1.6 mmol) was added and the mixture stirred for 20 h. EtOAc (125 ml) and water (75 ml) were added, followed by NaHCO$_3$ (1.7 g, 20.2 mmol) and benzyl chloridocarbonate (3.0 ml, 20.2 mmol). The mixture was stirred for 2 h, adjusted to pH7 with 2M HCl, extracted with EtOAc (3×100 ml), washed with brine, dried (MgSO$_4$), filtered and evaporated in vacuo. The residue was purified by chromatography on silica with 10% (0.1% aqNH$_3$/MeOH)/DCM as eluent to give the sub-title compound as a colourless oil. Yield (6.0 g).

MS: APCI (+ve): 433 (M+1).

$^1$H NMR DMSO-d6, δ 7.33 (m, 5H), 6.74 (d, 1H), 6.67 (d, 1H), 5.06 (s, 2H), 4.40 (t, 1H), 3.45 (t, 2H), 3.26 (s, 6H), 3.21 (d, 2H), 2.71 (t, 2H).

b) Benzyl [2-(4-hydroxy-2-oxo-2,3-dihydro-1,3-benzothiazol-7-yl)ethyl](2-oxoethyl) carbamate

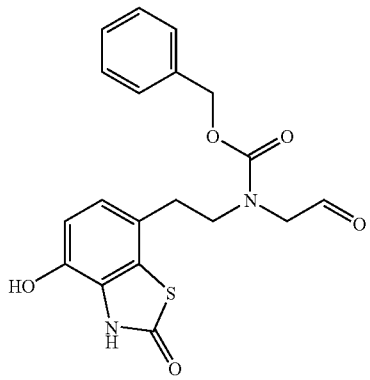

The product from part a) (1.5 g, 3 mmol) was dissolved in acetone (15 ml), 4M HCl/dioxane (1.5 ml) was added and the mixture was stirred for 30 min. Toluene (20 ml) was added and the mixture evaporated to give the sub-title compound as a pale yellow solid. Yield (1.5 g).

MS: APCI (+ve): 387 (M+1).

c) Benzyl (2-{[2-(diethylamino)ethyl]amino}ethyl)[2-(4-hydroxy-2-oxo-2,3-dihydro-1,3-benzothiazol-7-yl)ethyl]carbamate

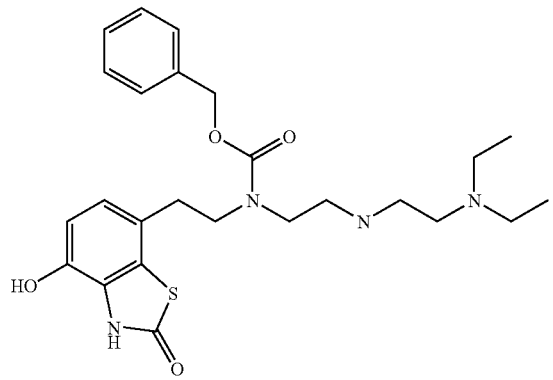

A solution of the product from part b) (5.5 g, 13 mmol) in THF (10 ml) was added to a solution of N,N-diethylethane-1,2-diamine (540 μl, 3.8 mmol) in THF (30 ml) and stirred for 30 min. Sodium triacetoxyborohydride (1.47 g, 6.9 mmol) was added and stirred for a further 20 h. The reaction was quenched with water, adjusted to pH7 with 2M HCl, extracted with EtOAc (3×50 ml), which was washed with brine, dried (MgSO$_4$), filtered and evaporated in vacuo. The residue was purified by chromatography on silica with 30% (0.1% aqNH$_3$/MeOH)/DCM as eluent to give the sub-title compound as a colourless oil. Yield (500 mg).

MS: APCI (+ve): 487 (M+1).

$^1$H NMR DMSO-d6, 90° C., δ8.21-8.09 (m, 2H), 7.32 (m, 5H), 6.79 (d, 1H), 6.70 (d, 1H), 5.07 (s, 2H), 1.26 (m, 6H), 3.28 (t, 4H), 3.55-3.36 (m, 6H), 3.20-3.08 (m, 6H)

d) tert-Butyl 3-[2-(2-(trifluoromethyl)phenyl)ethoxy]propanoate

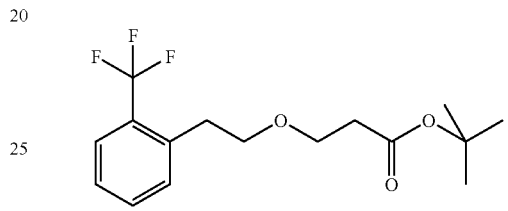

2-(2-Trifluoromethylphenyl)ethanol (4.88 g) was treated with Triton B (290 ul) (40 wt % in methanol). The methanol was removed by evaporation and the residue azeotroped with toluene (×2). The mixture was cooled in an ice bath and tert-butyl acrylate (4.13 ml) was added slowly. The mixture was stirred for 4 days and then evaporated. The residue was purified by chromatography on silica with 5% ethyl acetate/isohexane to give the sub-title compound as a clear, colourless oil (7.88 g).

$^1$H NMR (400 MHz, DMSO-d6) δ 1.41 (s, 9H), 2.43 (t, J=6.2 Hz, 2H), 2.98 (t, J=7.3 Hz, 2H), 3.62 (q, J=6.5 Hz, 4H), 7.44 (t, J=7.6 Hz, 1H), 7.53 (d, J=6.5, 2.1 Hz, 1H), 7.60 (d, J=6.5, 2.1 Hz, 1H), 7.69 (d, J=6.5 Hz, 1H).

e) 3-[2-(2-(Trifluoromethyl)phenyl)ethoxy]propanoic Acid

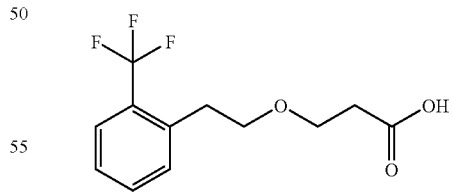

The product of part a) (7.88 g) was dissolved in DCM (100 ml), and TFA (40 ml) was added. After stirring for 2 hr the solvent was removed in vacuo to give the sub-title compound as a clear colourless oil (7.55 g).

$^1$H NMR (300 MHz, DMSO-d6) δ 2.46 (t, J=6.6 Hz, 2H), 2.99 (t, J=6.6 Hz, 2H), 3.63 (q, J=6.7 Hz, 4H), 7.44 (dd, J=7.7 Hz, 1H), 7.54 (d, J=7.8 Hz, 1H), 7.62 (t, J=7.3 Hz, 1H), 7.69 (d, J=7.2 Hz, 1H).

f) Benzyl {2-[[2-(diethylamino)ethyl](3-{2-[2-(trif-luoromethyl)phenyl]ethoxy}propanoyl)amino]ethyl}[2-(4-hydroxy-2-oxo-2,3-dihydro-1,3-benzothiazol-7-yl)ethyl]carbamate

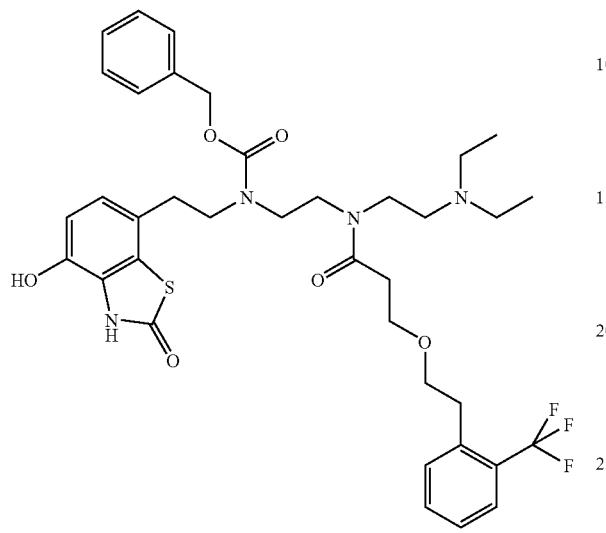

The product from part e) (260 mg, 1.0 mmol) was dissolved in DCM (10 ml) and oxalyl chloride (260 ul, 3.0 mmol) was added, followed by DMF (1 drop). The mixture was stirred for 1 hour, toluene (20 ml) was added and then evaporation afforded the acid chloride. The product from part c) (500 mg, 1.0 mmol) was dissolved in a mixture of DCM (10 ml) and THF (10 ml), Et$_3$N (420 µl, 3 mmol) was added, followed by the acid chloride (above). The mixture was stirred for 3 h, quenched with water, and extracted with EtOAc (2×50 ml), which was washed with brine, dried (MgSO$_4$), filtered and evaporated in vacuo. The residue was purified by reverse phase HPLC with MeCN/(0.2% aqueous TFA) eluant to give the sub-title compound as a colourless oil (310 mg).

MS: APCI (+ve): 731 (M+1).

$^1$H NMR CDCl$_3$, δ 7.62 (m, 1H), 7.43-7.29 (m, 5H), 7.33 (m, 1H), 7.17 (m, 2H), 6.83 (d, 1H), 6.72 (d, 1H), 5.30 (s, 2H), 3.76-2.74 (m, 20H), 2.61 (m, 4H), 1.30 (t, 6H).

g) N-[2-(Diethylamino)ethyl]-N-(2-{[2-(4-hydroxy-2-oxo-2,3-dihydro-1,3-benzothiazol-7-yl)ethyl]amino}ethyl)-3-{2-[2-(trifluoromethyl)phenyl]ethoxy}propanamide ditrifluoroacetate The product from part f) (300 mg, 0.4 mmol) was dissolved in DCM (2 ml). Hydrogen bromide 30% wt solution in acetic acid (1.0 ml) was added and the mixture stirred for 2 hr. Toluene (10 ml) was added and the mixture was evaporated in vacuo; the residue was purified by reverse phase HPLC with MeCN/(0.2% aqueous TFA) as eluant to give the title compound as a colourless gum (90 mg).

MS: APCI (+ve): 597 (M+1).

$^1$H NMR DMSO-d6, 90° C., δ 7.65 (m, 1H), 7.57 (m, 1H), 7.48 (m, 1H), 7.41 (m, 1H), 6.85 (d, 1H), 6.75 (d, 1H), 3.70 (t, 2H), 3.65 (t, 2H), 3.60 (m, 6H), 3.11 (m, 8H), 3.00 (t, 2H), 2.84 (t, 2H), 2.63 (t, 2H), 1.21 (t, 6H)

EXAMPLE 18

3-[2-(3-Chlorophenyl)ethoxy]-N-[2-(diethylamino)ethyl]-N-(2-{[2-(4-hydroxy-2-oxo-2,3-dihydro-1,3-benzothiazol-7-yl)ethyl]amino}ethyl)propanamide ditrifluoroacetate

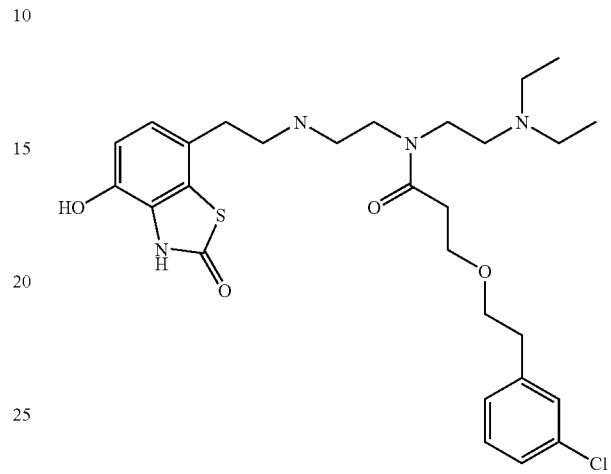

a) tert-Butyl 3-[2-(3-chlorophenyl)ethoxy]propanoate

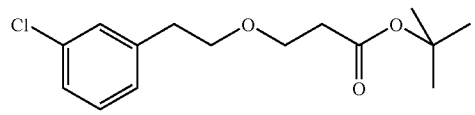

2-(3-Chlorophenyl)ethanol (3.0 g, 19.2 mmol) was reacted using method as of Example 17 part d) to give the sub-title compound as a colourless oil (5.25 g).

$^1$H NMR (300 MHz, DMSO-d6) δ 1.39 (s, 9H), 2.42 (t, J=5.8 Hz, 2H), 2.82 (t, J=6.9 Hz, 2H), 3.58 (m, 4H), 7.20-7.34 (m, 4H).

b) 3-[2-(3-Chlorophenyl)ethoxy]propanoic Acid

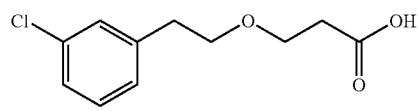

The product from part a) (5.25 g) was reacted using the method as of example 17 part e) to give the sub-title compound as a purple oil (4.81 g).

$^1$H NMR (400 MHz, DMSO-d6) δ 2.42 (t, J=6.6 Hz, 2H), 2.79 (t, J=6.6 Hz, 2H), 3.58 (q, J=6.5 Hz, 4H), 7.19-7.31 (m, 4H).

c) Benzyl (2-{{3-[2-(3-chlorophenyl)ethoxy]pro-
panoyl}[2-(diethylamino)ethyl]amino}ethyl)[2-(4-
hydroxy-2-oxo-2,3-dihydro-1,3-benzothiazol-7-yl)
ethyl]carbamate

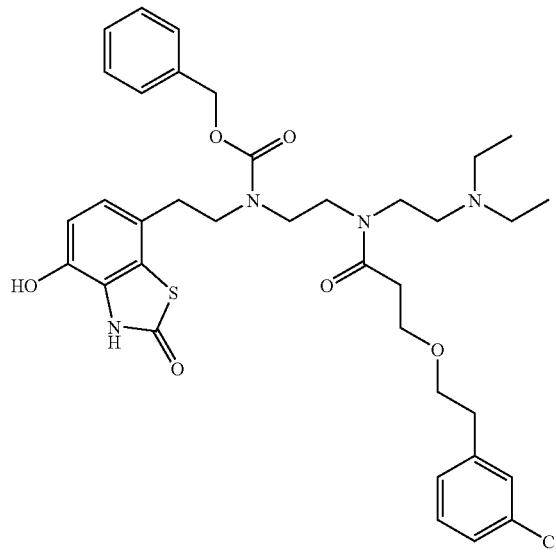

The product from part b) (240 mg, 1.0 mmol) and the product from example 17 part c) (500 mg, 1.0 mmol) were reacted using the method as of example 17 part f) to give the sub-title compound as a colourless oil (340 mg).

MS: APCI (+ve): 698 (M+1).

¹H NMR DMSO-d6, 90° C., δ 11.21 (s, 1H), 7.37-7.13 (m, 8H), 6.75 (d, 1H), 6.68 (d, 1H), 5.04 (s, 2H), 3.64-3.49 (m, 8H), 3.43 (t, 2H), 3.39 (t, 2H), 3.27 (t, 2H), 3.13 (m, 6H), 2.77 (t, 2H), 2.71 (t, 2H), 1.19 (t, 6H)

d) 3-[2-(3-Chlorophenyl)ethoxy]-N-[2-(diethy-
lamino)ethyl]-N-(2-{[2-(4-hydroxy-2-oxo-2,3-dihy-
dro-1,3-benzothiazol-7-yl)ethyl]amino}ethyl)pro-
panamide ditrifluoroacetate The product from part d) (330 mg, 0.47 mmol) was reacted using the method as of Example 17 part g) to give the title compound as a colourless gum (340 mg).

MS: APCI (+ve): 563 (M+1).

¹H NMR DMSO-d6, 90° C., δ7.30-7.16 (m, 4H), 6.85 (d, 1H), 6.75 (d, 1H), 3.68 (t, 2H), 3.64 (t, 2H), 3.59 (m, 6H), 3.19-3.05 (m, 8H), 2.84 (t, 2H), 2.81 (t, 2H), 2.61 (t, 2H), 1.20 (t, 6H)

EXAMPLE 19

N-[2-(Diethylamino)ethyl]-N-(2-{[2-(4-hydroxy-2-
oxo-2,3-dihydro-1,3-benzothiazol-7-yl)ethyl]
amino}ethyl)-3-[2-(4-hydroxyphenyl)ethoxy]pro-
panamide ditrifluoroacetate

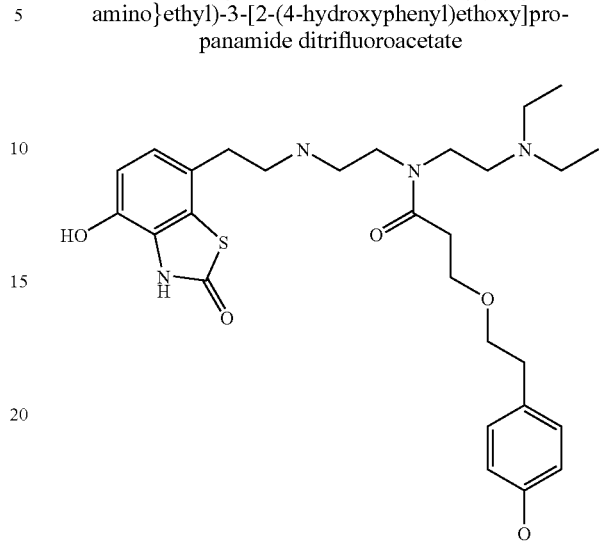

a) tert-Butyl 3-{2-[4-(benzyloxy)phenyl]
ethoxy}propanoate

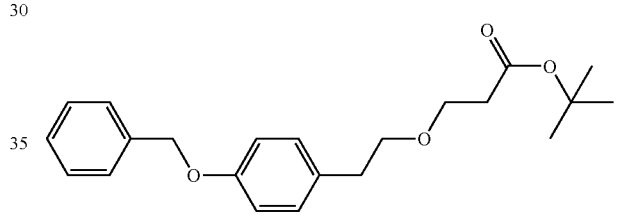

2-[4-(Benzyloxy)phenyl]ethanol (3.4 g, 14.8 mmol) was reacted using method as of example 17 part d) to give the sub-title compound as a colourless oil (3.86 g).

¹H NMR (300 MHz, DMSO-d6) δ 1.38 (s, 9H), 2.40 (t, J=6.1 Hz, 2H), 2.71 (t, J=7.4 Hz, 2H), 3.50-3.65 (m, 4H), 5.06 (s, 2H), 6.90 (d, J=10 Hz, 2H), 7.31-7.45 (m, 5H)

b) 3-{2-[4-(Benzyloxy)phenyl]ethoxy}propanoic
Acid

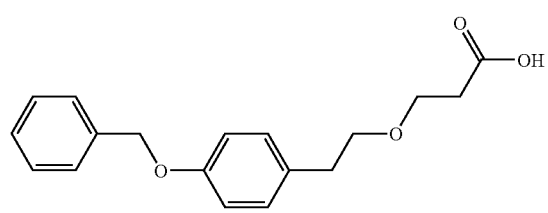

The product from part a) (3.86 g, 10.8 mmol) was reacted using the method as of Example 17 part e) to give the sub-title compound as a brown solid (3.81 g).

¹H NMR (300 MHz, DMSO-d6) δ 2.43 (t, J=6.5 Hz, 2H), 2.71 (t, J=7.3 Hz, 2H), 3.52 (t, J=7.6 Hz, 2H), 3.59 (t, J=6.3 Hz, 2H), 5.06 (s, 2H), 6.91 (d, J=8.3 Hz, 2H), 7.14 (d, J=8.3 Hz, 2H), 7.30-7.45 (m, 5H)

c) Benzyl (2-{(3-{2-[4-(benzyloxy)phenyl]
ethoxy}propanoyl)[2-(diethylamino)ethyl]
amino}ethyl)[2-(4-hydroxy-2-oxo-2,3-dihydro-1,3-
benzothiazol-7-yl)ethyl]carbamate

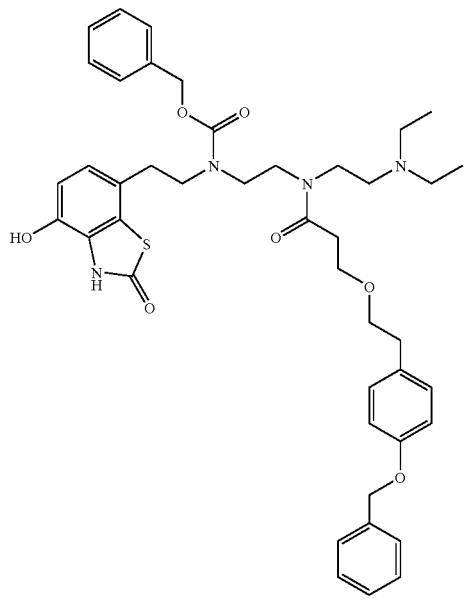

The product from part b) (300 mg, 1.0 mmol) and the product from Example 17 part c) (500 mg, 1.0 mmol) were reacted using the method as of example 17 part f) to give the sub-title compound as a colourless oil (360 mg).

MS: APCI (+ve): 769 (M+1).

d) N-[2-(Diethylamino)ethyl]-N-(2-{[2-(4-hydroxy-
2-oxo-2,3-dihydro-1,3-benzothiazol-7-yl)ethyl]
amino}ethyl)-3-[2-(4-hydroxyphenyl)ethoxy]pro-
panamide ditrifluoroacetate The product from part c) (350 mg, 0.45 mmol) was reacted using the method as of Example 17 part f) to give the title compound as a colourless gum (80 mg).

MS: APCI (+ve): 545 (M+1).

$^1$H NMR DMSO-d6, 90° C., δ 6.98 (d, 2H), 6.85 (d, 1H), 6.75 (d, 1H), 6.66 (m, 2H), 3.67 (t, 2H), 3.57 (m, 8H), 3.17-3.02 (m, 8H), 2.84 (t, 2H), 2.67 (m, 2H), 2.61 (t, 2H), 1.20 (t, 6H).

EXAMPLE 20

3-[2-(2,3-Dichlorophenyl)ethoxy]-N-(2-diethylami-
noethyl)-N-(2-{[2-(4-hydroxy-2-oxo-2,3-dihydro-1,
3-benzothiazol-7-yl)ethyl]amino}ethyl)propanamide
ditrifluoroacetate

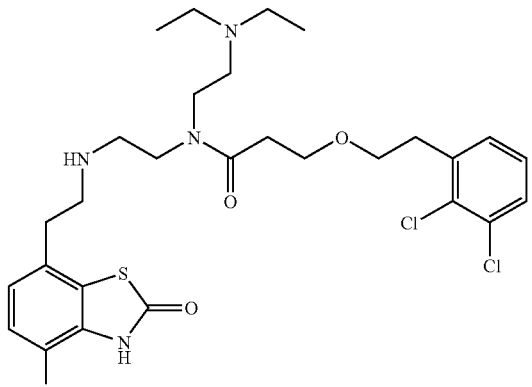

a) tert-Butyl
3-[2-(2,3-dichlorophenyl)ethoxy]propanoate

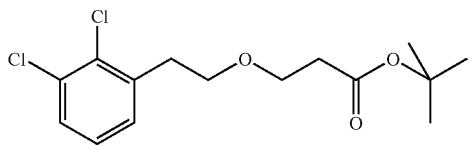

2-(3,4-Dichlorophenyl)ethanol (4.90 g) was reacted using method as of example 17 part d) to give the sub-title compound as a colourless oil (7.42 g).

$^1$H NMR (400 MHz, DMSO-d6) δ 1.36 (s, 9H), 2.39 (t, J=6.2 Hz, 2H), 2.97 (t, J=6.8 Hz, 2H), 3.60 (q, J=6.8 Hz, 4H), 7.27 (t, J=7.7 Hz, 1H), 7.35 (dd, J=7.6, 2.1 Hz, 1H), 7.49 (dd, J=8.5, 2.1 Hz, 1H).

b) 3-[2-(3,4-Dichlorophenyl)ethoxy]propanoic Acid

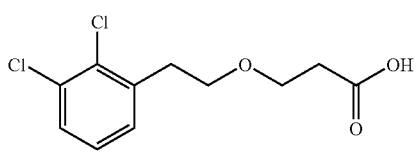

The product from part a) (7.42 g) was reacted using the method as of example 17 part e) to give the sub-title compound as a colourless oil (7.13 g).

$^1$H NMR (300 MHz, DMSO-d6) δ 2.42 (t, J=6.9 Hz, 2H), 2.80 (t, J=6.9 Hz, 2H), 3.56-3.62 (m, 4H), 7.24 (dd, J=8.3, 2.0 Hz, 1H), 7.50-7.53 (m, 2H)

c) Benzyl {2-[{3-[2-(2,3-dichloro-phenyl)ethoxy]propanoyl}-(2-diethylaminoethyl) amino]ethyl}-[2-(4-hydroxy-2-oxo-2,3-dihydro-1,3-benzothiazol-7-yl)ethyl]carbamate

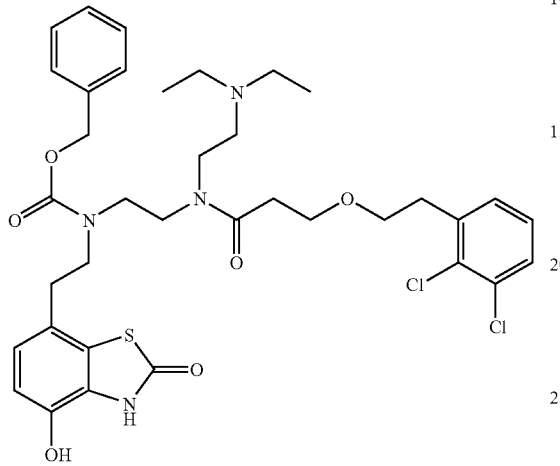

The product from part b) (195 mg, 0.74 mmol) was dissolved in DCM (7 ml) and oxalyl chloride (18 mg, 127 ul, 1.48 mmol) added, followed by DMF (6 ul). The mixture was stirred for 1 hour, evaporated to dryness and the residue azeotroped with toluene (×2) to afford the acid chloride. The product from example 17 part c) (360 mg, 0.74 mmol) was dissolved in THF (9 ml) and N-ethyl-N-isopropyl-2-propanamine (Hunig's base) (183 mg, 247 ul, 1.42 mmol) added. The mixture was cooled in an ice bath. The acid chloride (above) was dissolved in THF (5 ml) and added dropwise to the amine mixture. After stirring under nitrogen overnight, solvent was removed in vacuo, and residue purified on a silica cartridge, eluting with 3% 0.7 methanolic ammonia: 97% DCM to give a the sub-title compound as clear oil/gum (249 mg) which was used without further purification in the next step.

M+H=731, M−H=729.

d) 3-[2-(2,3-Dichlorophenyl)ethoxy]-N-(2-diethylaminoethyl)-N{2-[2-(4-hydroxy-2-oxo-2,3-dihydro-1,3-benzothiazol-7-yl)ethylamino]ethyl}propanamide ditrifluoroacetate The product from part c) (249 mg, 0.34 mmol) was reacted using the method of Example 17 part f) to give the title compound as a colourless gum (167 mg).

MS: APCI (+ve): 597 (M+1)

$^1$H NMR (400 MHz, DMSO-d6, 90° C.) δ 1.20 (t, J=7.7 Hz, 6H), 2.62 (t, J=7.7 Hz, 2H), 2.81 (t, J=7.1 Hz, 4H), 3.11-3.17 (m, 10H), 3.55-3.66 (m, 8H), 6.74-6.77 (m, 1H), 6.85 (t, J=6.4 Hz, 1H), 7.24 (d, J=8.6 Hz, 1H), 7.53 (d, J=9.4 Hz, 2H), 8.60 (s, 1H), 8.79 (s, 1H), 9.25 (s, 0.5H), 9.59 (s, 0.5H), 10.14 (d, J=8.8 Hz, 1H), 11.74 (d, J=8.8 Hz, 1H).

EXAMPLE 21

3-[2-(2-Bromo-5-methoxyphenyl)ethoxy]-N-[2-(diethylamino)ethyl]-N-(2-{[2-(4-hydroxy-2-oxo-2,3-dihydro-1,3-benzothiazol-7-yl)ethyl]amino}ethyl)propanamide dihydrobromide

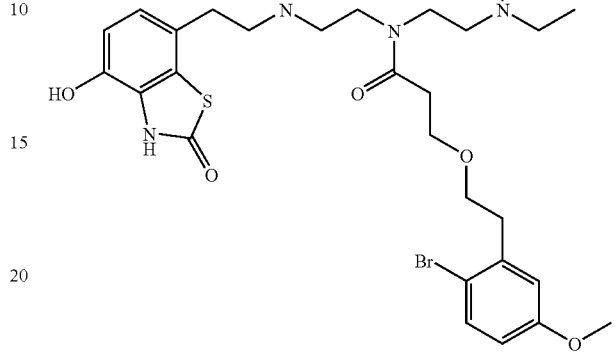

a) Benzyl (2,2-dimethoxyethyl)[2-(4-hydroxy-2-oxo-2,3-dihydro-1,3-benzothiazol-7-yl)ethyl]carbamate

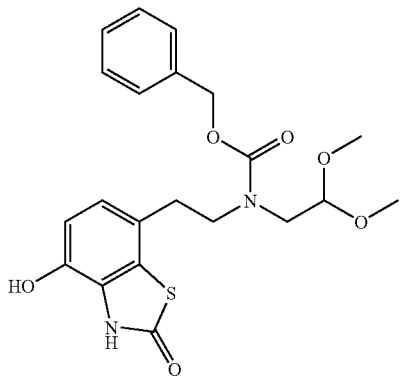

60% Aqueous dimethoxyacetaldehyde (7.0 ml, 40 mmol) was added dropwise over 1 min to a solution of 7-(2-aminoethyl)-4-hydroxy-1,3-benzothiazol-2(3H)-one hydrochloride (10.0 g, 40 mmol) in a mixture of THF (100 ml) and water (50 ml). The reaction was stirred for 30 min, AcOH (2.4 ml, 40 mmol) added, followed by sodium cyanoborohydride (5.1 g, 80 mmol) and stirred for 20 h. The mixture was quenched with water (50 ml), EtOAc (100 ml) added, followed by NaHCO$_3$ (13.6 g, 160 mmol) and the mixture stirred for 15 min. Benzyl chloridocarbonate (6.0 ml, 40 mmol) was then added and the reaction stirred for a further 3 h. The mixture was adjusted to pH7 with 2M HCl, extracted with EtOAc (3×100 ml), washed with water and brine, dried (MgSO$_4$), filtered and evaporated in vacuo. The residue was purified by chromatography on silica with 10% (0.1% aqNH$_3$/MeOH)/DCM as eluant to give the sub-title compound as a colourless oil. Yield (6.0 g).

MS: APCI (+ve): 433 (M+1).

$^1$H NMR 400 MHz, DMSO-d6, δ 7.33 (m, 5H), 6.74 (d, 1H), 6.67 (d, 1H), 5.06 (s, 2H), 4.40 (t, 1H), 3.45 (t, 2H), 3.26 (s, 6H), 3.21 (d, 2H), 2.71 (t, 2H).

b) Benzyl (2-{N-[2-(diethylamino)ethyl]-N-(tert-butoxycarbonyl)amino}ethyl)[2-(4-hydroxy-2-oxo-2,3-dihydro-1,3-benzothiazol-7-yl)ethyl]carbamate dihydrochloride

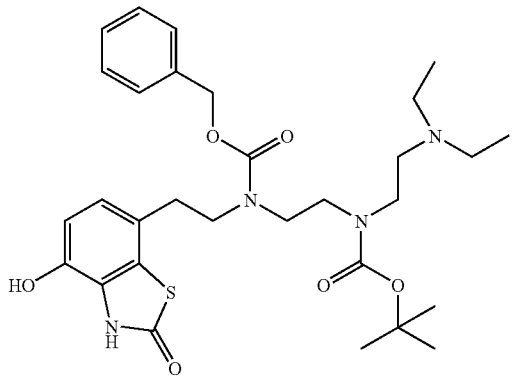

The product from part a) (5.5 g, 13 mmol) was dissolved in acetone (150 ml), 4M HCl/dioxane (15 ml) added and the whole was stirred for 30 min. Toluene (100 ml) was added and the mixture evaporated to afford the aldehyde. N,N-Diethylethane-1,2-diamine (3.64 ml, 26 mmol) was dissolved in THF (100 ml) and a solution of the above aldehyde in THF (100 ml) was added to it dropwise over 15 min. AcOH (3.0 ml, 52 mmol) was added and the mixture stirred for 15 min. Sodium triacetoxyborohydride (5.4 g, 26 mmol) was added and the mixture stirred for a further 20 h. Water (50 ml) was cautiously added and stirred for 15 min, then Et₃N (7.2 ml, 52 mmol) was added, followed by BOC₂O (5.5 g, 26 mmol) and stirred for 3 h. Further water (100 ml) was added and the mixture was extracted with EtOAc (3×100 ml). The combined extracts were washed with water and brine, dried (MgSO₄), filtered and evaporated in vacuo. The residue was purified by chromatography on silica with 10% (0.1% aqNH₃/MeOH)/DCM as eluant to give the sub-title compound as a colourless oil. Yield (6.0 g).

MS: APCI (+ve): 587 (M+1).

¹H NMR DMSO-d6, 90° C., δ 7.32 (m, 5H), 6.73 (d, 1H), 6.67 (d, 1H), 6.13 (s, 1H), 5.05 (s, 2H), 3.40 (t, 2H), 3.09 (m, 6H), 2.98 (m, 4H), 2.70 (t, 2H), 2.46 (m, 2H), 1.38 (s, 9H), 0.96 (t, 6H)

c) Benzyl (2-{[2-(diethylamino)ethyl]amino}ethyl)[2-(4-hydroxy-2-oxo-2,3-dihydro-1,3-benzothiazol-7-yl)ethyl]carbamate dihydrochloride

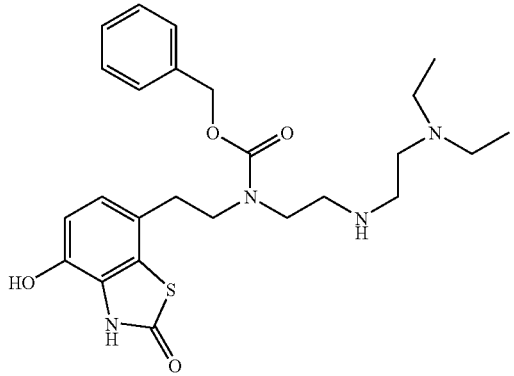

The product from part b) (6.0 g, 10 mmol) was dissolved in a mixture of DCM (100 ml) and MeOH (10 ml), then 4M HCl/dioxane (20 ml) was added and the whole was stirred for 3 h. Toluene (50 ml) was added and the mixture evaporated in vacuo leaving the sub-title compound as a gum (7.0 g).

MS: APCI (+ve): 487 (M+1).

¹H NMR DMSO-d6, 90° C., δ 8.21-8.09 (m, 2H), 7.32 (m, 5H), 6.79 (d, 1H), 6.70 (d, 1H), 5.07 (s, 2H), 1.26 (m, 6H), 3.28 (t, 4H), 3.55-3.36 (m, 6H), 3.20-3.08 (m, 6H)

d) tert-Butyl 3-[2-(3-methoxyphenyl)ethoxy]propanoate

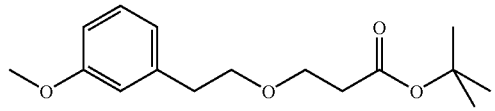

2-[3-Methoxyphenyl]ethanol (1.0 g, 6.57 mmol) was reacted using the method of Example 17 part d) to give the sub-title compound as a colourless oil (1.7 g).

¹H NMR DMSO-d6 δ 1.38 (s, 9H), 2.40 (t, J=6.9 Hz, 2H), 2.75 (t, J=7.5 Hz, 2H), 3.57 (t, J=6.9 Hz, 2H), 3.58 (t, J=6.2 Hz, 2H), 3.72 (s, 3H), 6.73-6.76 (m, 1H), 6.78-6.80 (m, 2H), 7.17 (t, J=8.0 Hz, 1H)

e) 3-[2-(3-Methoxyphenyl)ethoxy]propanoic Acid

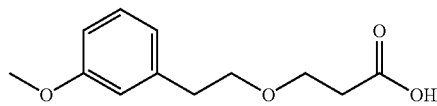

The product from part d) (1.7 g, 6.0 mmol) was reacted using the method of Example 17 part e) to give the sub-title compound as a brown solid (1.5 g).

¹H NMR DMSO-d6 δ 7.17 (m, 1H), 6.77 (m, 3H), 3.73 (s, 3H), 3.59 (m, 4H), 2.76 (t, 2H), 2.43 (t, 2H).

f) Benzyl [2-([2-(diethylamino)ethyl]{3-[2-(3-(methoxyphenyl)ethoxy]propanoyl}amino)ethyl][2-(4-hydroxy-2-oxo-2,3-dihydro-1,3-benzothiazol-7-yl)ethyl]carbamate

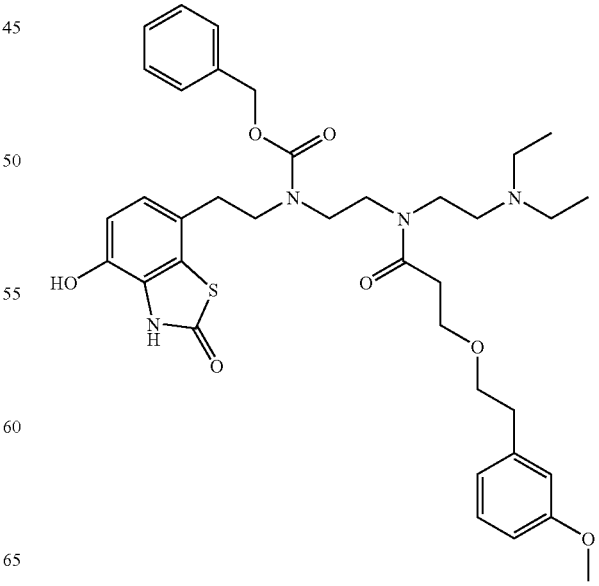

The product from part e) (120 mg, 0.52 mmol) was dissolved in DCM (5 ml), oxalyl chloride (260 μl, 3.0 mmol) was added, followed by DMF (1 drop). The mixture was stirred for 1.25 h, evaporated to dryness and the residue azeotroped with toluene (10 ml) to give the acid chloride. The product from part c) (290 mg, 0.52 mmol) was dissolved in a mixture of water (10 ml) and DCM (10 ml), solid NaHCO$_3$ was added (260 mg, 3.1 mmol) and the mixture was stirred vigorously. To it was added the above acid chloride dissolved in DCM (10 ml), dropwise over 5 min and the whole was stirred for 20 h. The mixture was extracted with DCM (2×50 ml), the combined extracts were washed with brine, dried (Na$_2$SO$_4$), filtered and evaporated to give a glassy gum. Purification by chromatography on is silica eluting with 10% 0.7M methanolic ammonia in DCM gave the sub-title compound as a clear colourless film (140 mg).

MS: APCI (+ve): 693 (M+1).

$^1$H NMR (400 MHz, DMSO) δ 7.32 (m, 5H), 7.13 (m, 1H), 6.74 (m, 4H), 6.67 (m, 1H), 5.04 (s, 2H), 3.71 (s, 3H), 3.59 (m, 4H), 3.41 (m, 2H), 3.34 (m, 2H), 3.25 (m, 4H), 2.71 (m, 6H), 2.50-2.37 (m, 6H), 0.93 (m, 6H)

g) 3-[2-(2-Bromo-5-methoxyphenyl)ethoxy]-N-[2-(diethylamino)ethyl]-N-(2-{[2-(4-hydroxy-2-oxo-2,3-dihydro-1,3-benzothiazol-7-yl)ethyl]amino}ethyl)propanamide dihydrobromide The product from part f) (130 mg, 0.18 mmol) was dissolved in DCM (5 ml). Hydrogen bromide 30% wt solution in acetic acid (2.0 ml) was added and the solution was stirred for 3 h. Toluene (10 ml) was added, volatiles were evaporated in vacuo and the residue purified by reverse phase HPLC with MeCN/(0.2% aqueous TFA) as eluant. The product fractions were combined and evaporated in vacuo, and the residue was dissolved in 50% aqueous EtOH, 48% aqueous HBr (200 μl) was added and again evaporated in vacuo. The residue was azeotroped with EtOH (×2) and then triturated with EtOH to give the title compound as a colourless solid (80 mg).

MS: APCI (+ve): 637 (M+1).

$^1$H NMR (400 MHz, DMSO) δ 9.64 (s, 1H), 7.43 (d, 1H), 6.92 (d, 1H), 6.87 (d, 1H), 6.76 (m, 3H), 3.75 (s, 3H), 3.72 (m, 4H), 3.68-3.59 (m, 4H), 3.24-3.10 (m, 6H), 2.88 (m, 4H), 2.65 (t, 2H), 1.24 (t, 6H).

EXAMPLE 22

N-(2-Diethylaminoethyl)-3-[2-(3-fluorophenyl)ethoxy]-N-{2-[2-(4-hydroxy-2-oxo-2,3-dihydro-1,3-benzothiazol-7-yl)ethylamino]ethyl}propanamide dihydrobromide

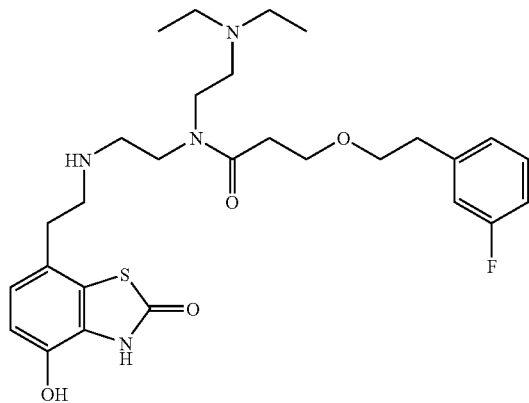

a) tert-Butyl 3-[2-(3-fluorophenyl)ethoxy]propionate

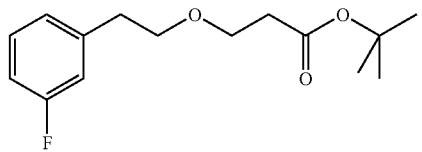

1-(3-Fluorophenyl)ethanol (850 mg) was reacted using method as of Example 17 part d) to give the sub-title compound as a clear, colourless oil (1.55 g).

$^1$H NMR (400 MHz, DMSO-d6) δ 1.36 (s, 9H), 2.39 (t, J=6.4 Hz, 2H), 2.80 (t, J=6.9 Hz, 2H), 3.58 (q, J=6.0 Hz, 4H), 6.99 (t, J=10.4 Hz, 1H), 7.06 (d, J=9.4 Hz, 2H), 7.26-7.32 (m, 1H)

b) 3-[2-(3-Fluorophenyl)ethoxy]propanoic Acid

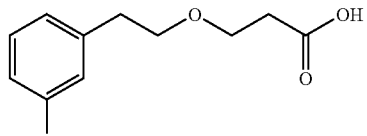

The product from part a) (1.55 g) was reacted using the method as of Example 17 part e) to give the sub-title compound as a purple oil (1.5 g).

$^1$H NMR (300 MHz, DMSO-d6) δ 2.45 (t, J=6.8 Hz, 2H), 2.83 (t, J=6.8 Hz, 2H), 3.59-3.64 (m, 4H), 7.02 (t, J=10.2 Hz, 1H), 7.09 (d, J=8.0 Hz, 2H), 7.32 (q, J=7.6 Hz, 1H)

c) Benzyl [2-((2-diethylaminoethyl)-{3-[2-(3-fluorophenyl)ethoxy]propanoyl}amino)ethyl]-[2-(4-hydroxy-2-oxo-2,3-dihydro-1,3-benzothiazol-7-yl)ethyl]carbamate

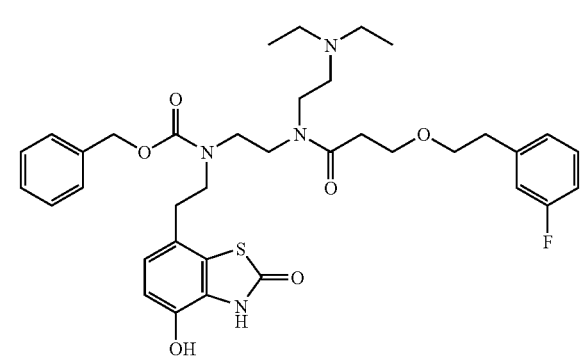

The product from part b) (104 mg) was dissolved in DCM (5 ml), and oxalyl chloride (84 ul) was added, followed by DMF (4 ul). The solution was then stirred for 1.25 h. The mixture was evaporated to dryness, and the residue was azeotroped twice with toluene to afford the acid chloride. Redissolved in THF (5 ml) it was added dropwise to a solution prepared as follows: a solution of the product from example 17 part c) (5.14 ml; 0.1M in methanol) was treated with triethylamine (217 ul). Solvents were removed in vacuo to give a white sticky solid (a mixture of triethylamine HCl and amine free base). This mixture was suspended in THF (7 ml) and cooled in an ice bath, the solution of the acid chloride added and then Hunig's base (334 ul) was added. After stirring for 3 days water was added to dissolve triethylamine hydrochloride and 2N HCl was added until the solution was at pH 7. The mixture was extracted with ethyl acetate (×3), and the combined organics were dried (Na$_2$SO$_4$), filtered and evaporated to give an orange oil (140 mg). This material was purified by chromatography on silica eluting with 10% 0.7N methanolic ammonia in DCM to give the sub-title compound as a yellow oil (78 mg).

MS: APCI (+ve): 681 (M+1)

d) N-(2-Diethylaminoethyl)-3-[2-(3-fluorophenyl) ethoxy]-N-{2-[2-(4-hydroxy-2-oxo-2,3-dihydro-1,3-benzothiazol-7-yl)ethylamino]ethyl}propanamide dihydrobromide The product from part c) (228 mg) was reacted using the method of Example 21 part g) to give the title compound as a white solid (96 mg).

MS: APCI (+ve): 547 (M+1)

$^1$H NMR (400 MHz, DMSO-d6) δ 1.26 (t, J=7.3 Hz, 6H), 2.65 (t, J=6.4 Hz, 2H), 2.84 (t, J=6.4 Hz, 2H), 2.90 (t, J=8.0 Hz, 2H), 3.19 (t, J=7.4 Hz, 10H), 3.65-3.72 (m, 8H), 6.77 (d, J=8.4 Hz, 1H), 6.89 (d, J=8.4 Hz, 1H), 6.98 (tt, J=9.1, 9.1 Hz, 1H), 7.05 (t, J=9.1 Hz, 2H), 7.31 (q, J=7.7 Hz, 1H), 8.62 (s, 1H), 9.63 (s, 1H), 11.33 (s, 1H).

EXAMPLE 23

N-(2-Diethylaminoethyl)-N-{2-[2-(4-hydroxy-2-oxo-2,3-dihydro-1,3-benzothiazol-7-yl)ethylamino] ethyl}-3-(2-methyl-2-phenylpropoxy)propanamide dihydrobromide

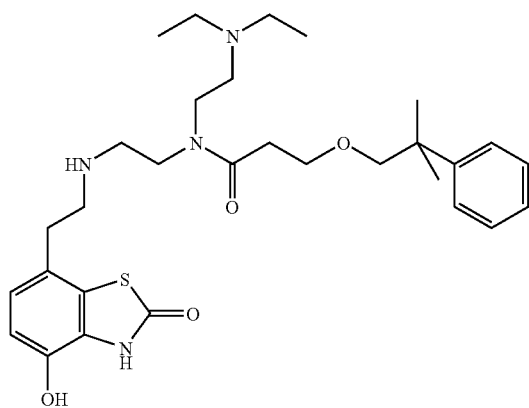

i) tert-Butyl 3-(2-methyl-2-phenylpropoxy)propanoic Acid

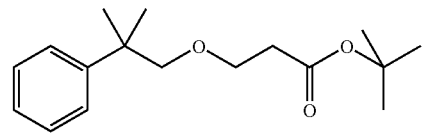

2-Methyl-2-phenyl-propan-1-ol (1 g) was reacted using method as of Example 17 part d) to give the sub-title compound as a clear, colourless oil (305 mg).

$^1$H NMR (400 MHz, DMSO-d6) δ 1.23 (s, 6H), 1.37 (s, 9H), 2.37 (t, J=6.2 Hz, 2H), 3.41 (s, 2H), 3.55 (t, J=6.0 Hz, 2H), 7.16 (t, J=7.5 Hz, 1H), 7.27 (t, J=7.5 Hz, 2H), 7.36 (d, J=9.0 Hz, 2H)

b) 3-(2-Methyl-2-phenylpropoxy)propanoic Acid

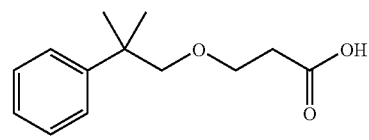

The product from part a) (305 mg) was reacted using the method as of Example 17 part e) to give the sub-title compound as a brown oil (326 mg).

$^1$H NMR (300 MHz, DMSO-d6) δ 1.25 (s, 6H), 2.42 (t, J=6.4 Hz, 2H), 3.43 (s, 2H), 3.59 (t, J=6.4 Hz, 2H), 7.16-7.21 (m, 1H), 7.29 (t, J=7.8 Hz, 2H), 7.39 (d, J=9.2 Hz, 2H)

c) Benzyl (2-{(2-diethylaminoethyl)-[3-(2-methyl-2-phenylpropoxy)propanoyl]-amino}ethyl)-[2-(4-hydroxy-2-oxo-2,3-dihydro-1,3-benzothiazol-7-yl) ethyl]carbamate

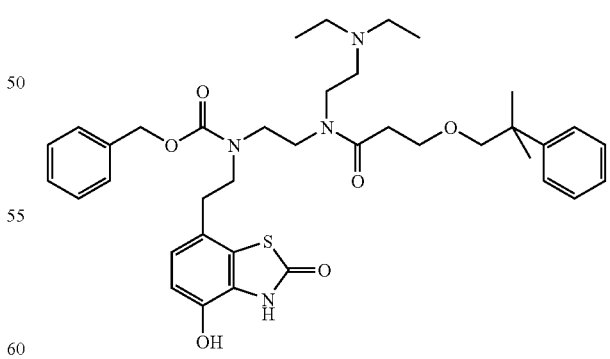

The product from part b) (108 mg) and the product from Example 21 part c) (5.14 ml; 0.1M in methanol) were reacted using the method of Example 22 part c) to give the sub-title compound as a brown gum (170 mg).

MS: APCI (+ve): 691 (M+1)

d) N-(2-Diethylaminoethyl)-N-{2-[2-(4-hydroxy-2-oxo-2,3-dihydro-1,3-benzothiazol-7-yl)ethylamino]ethyl}-3-(2-methyl-2-phenylpropoxy)propanamide dihydrobromide The product from part c) (170 mg) was reacted using the method of Example 21 part g) to give the sub-title compound as a white solid (56 mg).

MS: APCI (+ve): 557 (M+1)

¹H NMR (400 MHz, DMSO-d6) δ 1.19 (q, J=6.5 Hz, 6H), 1.24 (s, 6H), 2.57-2.62 (m, 2H), 2.79-2.85 (m, 2H), 3.04-3.18 (m, 10H), 3.45 (d, J=5.5 Hz, 2H), 3.51-3.57 (m, 4H), 3.59-3.64 (m, 2H), 6.73-6.77 (m, 1H), 6.84-6.87 (m, 1H), 7.14-7.19 (m, 1H), 7.25-7.30 (m, 2H), 7.36 (d, J=8.1 Hz, 2H), 8.47 (s, 1H), 8.61 (s, 1H), 9.19 (d, J=106.5 Hz, 1H), 10.08 (d, J=8.8 Hz, 1H), 11.74 (d, J=8.8 Hz, 1H)

EXAMPLE 24

3-[2-(2,6-Dichlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide dihydrobromide

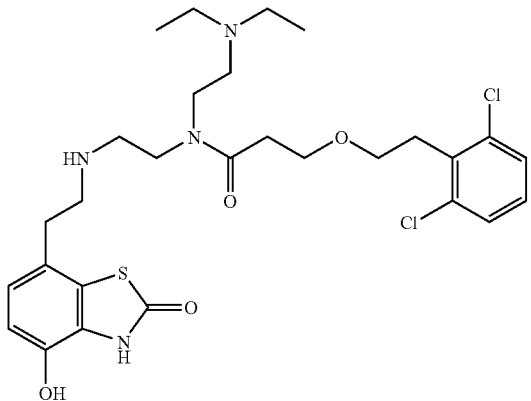

a) tert-Butyl 3-[2-(2,6-dichlorophenyl)ethoxy]propanoic Acid

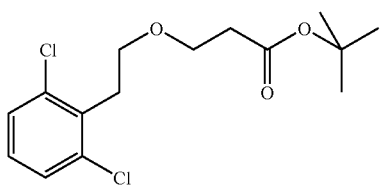

2,6-Dichlorophenethylalcohol (2.1 g) was reacted using method as of Example 17 part d) to give the sub-title compound as a clear, colourless oil (2.91 g).

¹H NMR (400 MHz, DMSO-d6) δ 1.38 (s, 9H), 2.40 (t, J=6.4 Hz, 2H), 3.11 (t, J=7.6 Hz, 2H), 3.52 (t, J=7.6 Hz, 2H), 3.60 (t, J=6.2 Hz, 2H), 7.27 (t, J=8.0 Hz, 1H), 7.44 (d, J=8.2 Hz, 2H)

b) 3-[2-(2,6-Dichlorophenyl)ethoxy]propanoic Acid

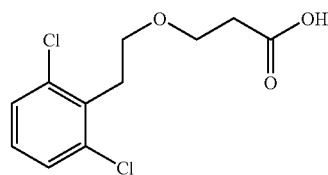

The product from part a) (2.17 g) was reacted using the method as of Example 17 part e) to give the sub-title compound as an orange oil (2.88 g).

c) Benzyl {2-[{3-[2-(2,6-Dichlorophenyl)ethoxy]propanoyl}(2-diethylaminoethyl)amino]ethyl}[2-(4-hydroxy-2-oxo-2,3-dihydro-1,3-benzothiazol-7-yl)ethyl]carbamate

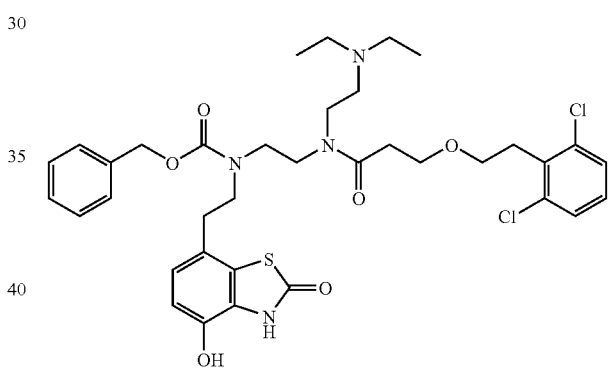

The product from part b) (271 mg) and the product from Example 17 part c) (5.14 ml; 0.1M in methanol) were reacted using the method of Example 21 part f) to give the sub-title compound as a brown gum (190 mg).

MS: APCI (+ve): 732 (M+1)

d) 3-[2-(2,6-Dichloro-phenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide dihydrobromide The product from Example 17 part c) (190 mg) was reacted using the method of Example 21 part g) to give the title compound as a white solid (101 mg).

MS: APCI (+ve): 597 (M+1)

¹H NMR (400 MHz, DMSO-d6) δ 1.24 (t, J=7.6 Hz, 6H), 2.65 (t, J=6.5 Hz, 2H), 2.88 (t, J=7.6 Hz, 2H), 3.14-3.19 (m, 12H), 3.58-3.65 (m, 6H), 3.72 (t, J=6.4 Hz, 2H), 6.75 (d, J=8.7 Hz, 1H), 6.87 (d, J=8.7 Hz, 1H), 7.26 (t, J=8.1 Hz, 1H), 7.41 (d, J=8.0 Hz, 2H), 9.64 (s, 1H), 11.33 (s, 1H)

EXAMPLE 25

N-(2-Diethylaminoethyl)-N-{2-[2-(4-hydroxy-2-oxo-2,3-dihydro-1,3-benzothiazol-7-yl)ethylamino]ethyl}-3-[2-(3-trifluoromethylphenyl)ethoxy]propanamide dihydrobromide

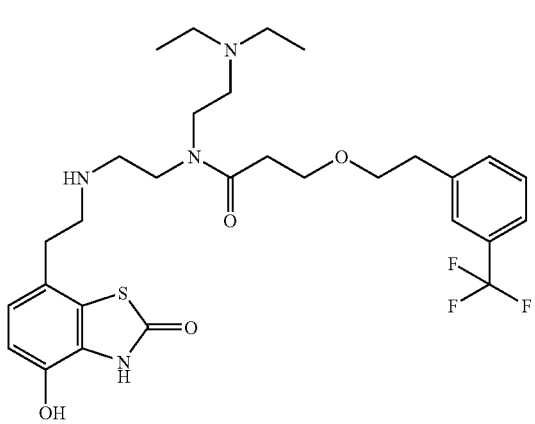

a) tert-Butyl 3-[2-(3-trifluoromethylphenyl)ethoxy]propanoate

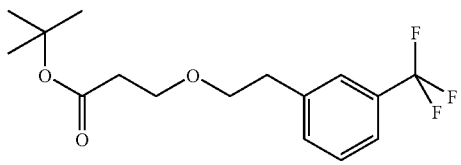

2-(3-Trifluoromethylphenyl)ethanol (1.15 g) was reacted using the method of Example 17 part d) to give the sub-title compound as a clear, colourless oil (1.93 g).

1H NMR (300 MHz, DMSO-d6) δ 1.37 (s, 9H), 2.41 (t, J=5.9 Hz, 2H), 2.91 (t, J=7.7 Hz, 2H), 3.61 (t, J=5.9 Hz, 2H), 3.65 (t, J=6.4 Hz, 2H), 7.49-7.61 (m, 4H)

b) 3-[2-(3-Trifluoromethylphenyl)ethoxy]propanoic Acid

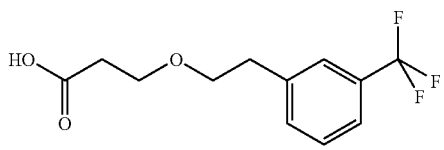

The product from part a) (1.93 g) was reacted using the method as of example 17 part e) to give the sub-title compound as an orange oil (1.99 g).

¹H NMR (300 MHz, DMSO-d6) δ 2.43 (t, J=6.4 Hz, 2H), 2.90 (t, J=7.5 Hz, 2H), 3.58-3.64 (m, 4H), 7.47-7.60 (m, 4H).

c) Benzyl [2-((2-diethylaminoethyl)-{3-[2-(3-trifluoromethylphenyl)ethoxy]-propanoyl}amino)ethyl]-[2-(4-hydroxy-2-oxo-2,3-dihydro-1,3-benzothiazol-7-yl)ethyl]carbamate

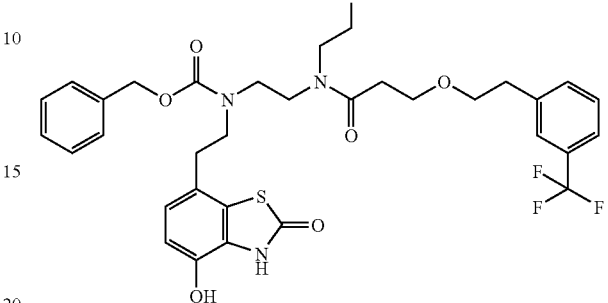

The product from part b) (197 mg) and the product from Example 17 part c) (5.14 ml; 0.1M in methanol) were reacted using the method of Example 21 part f) to give the sub-title compound as an orange oil (162 mg).

MS: APCI (+ve): 731 (M+1)

d) N-(2-Diethylaminoethyl)-N-{2-[2-(4-hydroxy-2-oxo-2,3-dihydro-1,3-benzothiazol-7-yl)ethylamino]ethyl}-3-[2-(3-trifluoromethylphenyl)ethoxy]propanamide dihydrobromide The product from part c) (162 mg) was reacted using the method of Example 21 part f) to give the title compound as a white solid (105 mg).

MS: APCI (+ve): 597 (M+1)

¹H NMR (400 MHz, DMSO-d6) δ 1.24 (t, J=7.0 Hz, 6H), 2.64 (t, J=6.4 Hz, 2H), 2.88 (t, J=7.7 Hz, 2H), 2.92 (t, J=6.6 Hz, 2H), 3.15-3.19 (m, 10H), 3.60-3.71 (m, 8H), 6.75 (d, J=8.3 Hz, 1H), 6.87 (d, J=8.3 Hz, 1H), 7.50 (s, 3H), 7.55 (s, 1H), 8.62 (s, 1H), 9.63 (s, 1H), 11.37 (s, 1H)

EXAMPLE 26

3-[2-(4-Chlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide dihydrobromide

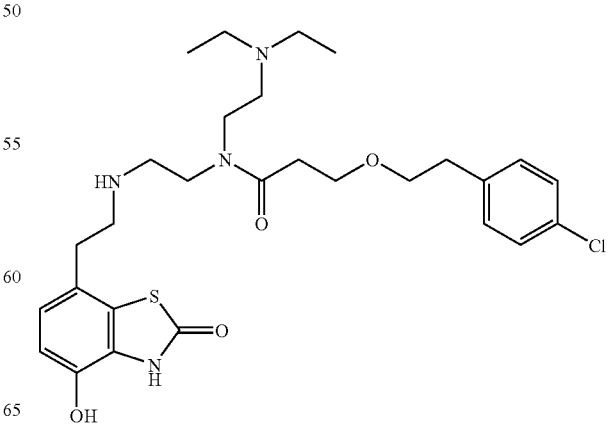

a) tert-Butyl 3-[2-(4-chlorophenyl)ethoxy]propanoate

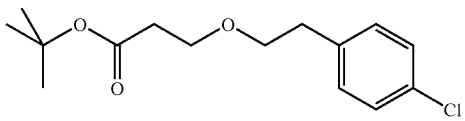

2-(4-Chlorophenyl)ethanol (1.0 g) was reacted using method as of example 17 part d) to give the sub-title compound as a clear, colourless oil (1.68 g).

$^1$H NMR (400 MHz, DMSO-d6) δ 1.37 (s, 9H), 2.39 (t, J=6.6 Hz, 2H), 2.77 (t, J=7.3 Hz, 2H), 3.57 (t, J=7.3 Hz, 4H), 7.25 (d, J=8.8 Hz, 2H), 7.31 (d, J=8.8 Hz, 2H)

b) 3-[2-(4-Chlorophenyl)ethoxy]propanoic Acid

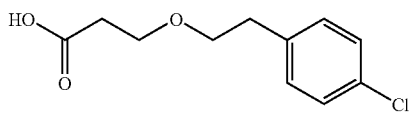

The product from part a) (1.68 g) was reacted using the method as of example 17 part e) to give the sub-title compound as a yellow oil (1.52 g).

$^1$H NMR (400 MHz, DMSO-d6) δ 2.43 (t, J=6.2 Hz, 2H), 2.78 (t, J=6.8 Hz, 2H), 3.57 (t, J=5.4 Hz, 2H), 3.60 (t, J=4.9 Hz, 2H), 7.26 (d, J=8.8 Hz, 2H), 7.32 (d, J=8.8 Hz, 2H)

c) Benzyl {2-[{3-[2-(4-chlorophenyl)ethoxy]propanoyl}-(2-diethylaminoethyl)-amino]ethyl}-[2-(4-hydroxy-2-oxo-2,3-dihydro-1,3-benzothiazol-7-yl)ethyl]carbamate

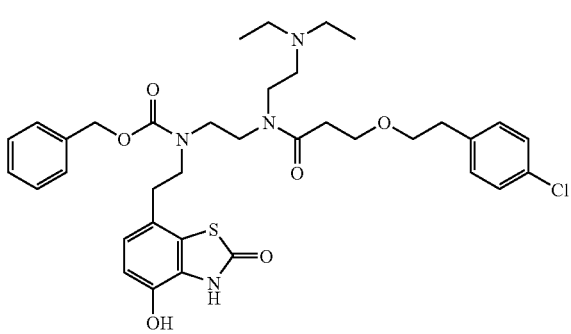

The product from part b) (162 mg) and the product from Example 17 part c) (5.14 ml; 0.1M in methanol) were reacted using the method of Example 21 part f) to give the sub-title compound as a orange oil (131 mg).

MS: APCI (+ve): 698 (M+1)

d) 3-[2-(4-Chlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide dihydrobromide The product from part c) (131 mg) was reacted using the method of Example 21 part g) to give the title compound as a white solid (78 mg).

MS: APCI (+ve): 563 (M+1)

$^1$H NMR (300 MHz, DMSO-d6, 90° C.) δ 1.25 (t, J=7.5 Hz, 6H), 2.63 (t, J=7.5 Hz, 2H), 2.80 (t, J=6.6 Hz, 2H), 2.89 (t, J=8.3 Hz, 2H), 3.14-3.20 (m, 10H), 3.61-3.70 (m, 8H), 6.75 (d, J=9.1 Hz, 1H), 6.88 (d, J=8.3 Hz, 1H), 7.26 (q, J=9.7 Hz, 4H), 8.56 (s, 1H), 9.63 (s, 1H), 11.32 (s, 1H)

EXAMPLE 27

3-[2-(3,4-Dichlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide dihydrobromide

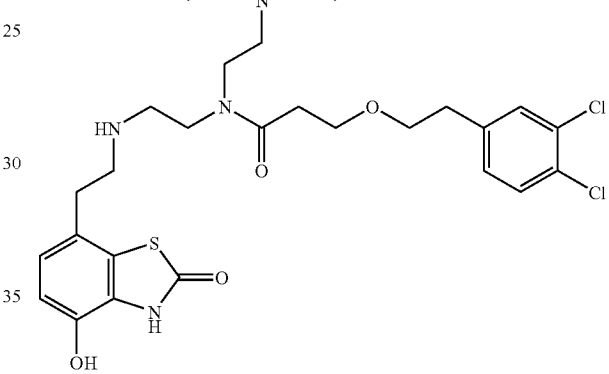

a) tert-Butyl 3-[2-(3,4-Dichlorophenyl)ethoxy]propanoate

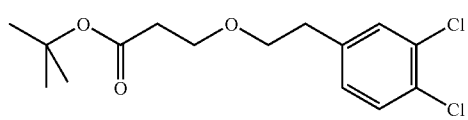

2-(3,4-Dichloro-phenyl)ethanol (5.11 g) was reacted using method as of Example 17 part d) to give the sub-title compound as a clear, colourless oil (5.77 g).

$^1$H NMR (300 MHz, DMSO-d6) δ 1.35 (s, 9H), 2.38 (t, J=6.2 Hz, 2H), 2.79 (t, J=6.6 Hz, 2H), 3.58 (q, J=6.1 Hz, 4H), 7.23 (dd, J=8.5, 2.1 Hz, 1H), 7.49-7.52 (m, 2H).

b) 3-[2-(3,4-Dichlorophenyl)ethoxy]propanoic Acid

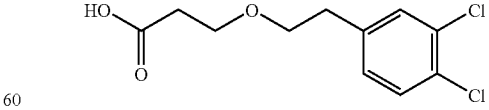

The product from part a) (5.77 g) was reacted using the method as of Example 17 part e) to give the sub-title compound as a yellow oil (5.89 g).

$^1$H NMR (300 MHz, DMSO-d6) δ 2.42 (t, J=6.9 Hz, 2H), 2.80 (t, J=6.9 Hz, 2H), 3.56-3.62 (m, 4H), 7.24 (dd, J=8.3, 2.0 Hz, 1H), 7.50-7.53 (m, 2H)

c) Benzyl {2-[{3-[2-(3,4-dichlorophenyl)ethoxy]propanoyl}-(2-diethylaminoethyl)amino]ethyl}-[2-(4-hydroxy-2-oxo-2,3-dihydro-1,3-benzothiazol-7-yl)ethyl]carbamate

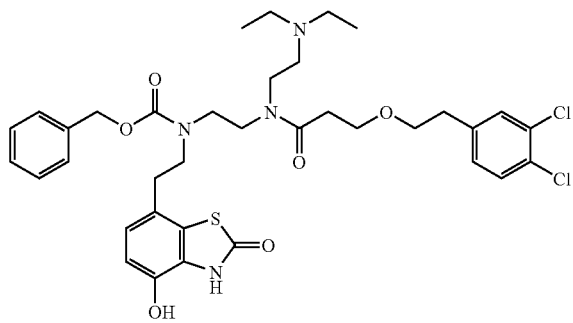

The product from part b) (198 mg) and the product from Example 17 part c) (5.14 ml; 0.1M in methanol) were reacted using the method of Example 21 part f) to give the sub-title compound as a orange oil (160 mg).

MS: APCI (+ve): 732 (M+1).

d) 3-[2-(3,4-Dichlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide dihydrobromide The product from part c) (160 mg) was reacted using the method of Example 21 part g) to give the title compound as a white solid (73 mg).

MS: APCI (+ve): 597 (M+1)
$^1$H NMR (400 MHz, DMSO-d6, 90° C.) δ 1.20-1.25 (m, 6H), 2.63 (t, J=7.5 Hz, 2H), 2.81 (t, J=7.5 Hz, 2H), 2.87 (t, J=7.5 Hz, 2H), 3.14-3.18 (m, 10H), 3.61-3.70 (m, 8H), 6.75 (d, J=8.5 Hz, 1H), 6.86 (d, J=8.5 Hz, 1H), 7.21 (d, J=8.5 Hz, 1H), 7.46-7.49 (m, 2H), 8.54 (s, 1H), 9.64 (s, 1H), 11.33 (s, 1H).

EXAMPLE 28

N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-methylphenyl)ethoxy]propanamide

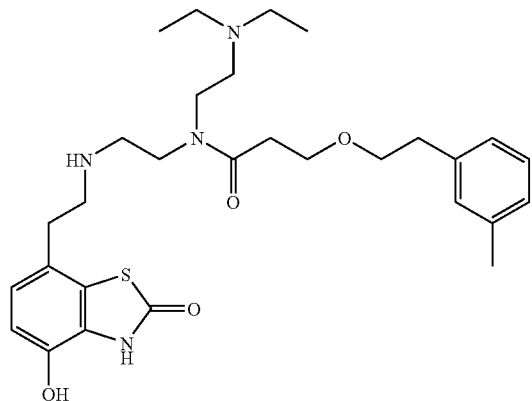

a) tert-Butyl 3-[2-(3-methylphenyl)ethoxy]propanoate

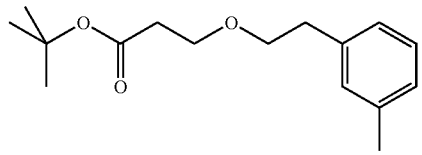

2-(3-Methylphenyl)ethanol (1.85 g) was reacted using method as of Example 17 part d) to give the sub-title compound as a clear, colourless oil (1.55 g).

$^1$H NMR (400 MHz, DMSO-d6) δ 1.37 (s, 9H), 2.26 (s, 3H), 2.40 (t, J=6.8 Hz, 2H), 2.74 (t, J=6.8 Hz, 2H), 3.54-3.59 (m, 4H), 6.98-7.03 (m, 3H), 7.14 (t, J=7.7 Hz, 1H).

b) 3-[2-(3-Methylphenyl)ethoxy]propanoic Acid

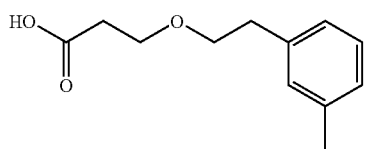

The product from part a) (1.55 g) was reacted using the method as of Example 17 part e) to give the sub-title compound as an orange oil (1.32 g).

$^1$H NMR (300 MHz, DMSO-d6) δ 2.27 (s, 3H), 2.43 (t, J=7.1 Hz, 2H), 2.74 (t, J=7.1 Hz, 2H), 3.56 (t, J=6.1 Hz, 2H), 3.60 (t, J=6.1 Hz, 2H), 6.98-7.04 (m, 3H), 7.15 (t, J=8.1 Hz, 1H).

c) Benzyl [2-([2-(diethylamino)ethyl]{3-[2-(3-methylphenyl)ethoxy]propanoyl}-amino)ethyl][2-(4-hydroxy-2-oxo-2,3-dihydro-1,3-benzothiazol-7-yl)ethyl]carbamate

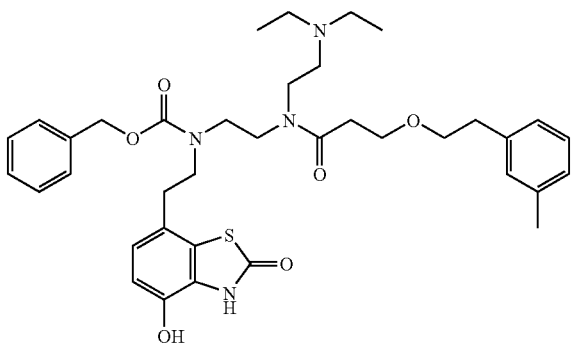

The product from part b) (125 mg) and the product from Example 17 part c) (5.14 ml; 0.1M in methanol) were reacted using the method of Example 21 part f) to give the sub-title compound as a orange oil (102 mg).

MS: APCI (+ve): 677 (M+1)

d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-methylphenyl)ethoxy]propanamide The product from part c) (102 mg) was reacted using the method of Example 21 part g) to give the title compound as a white solid (36 mg).

MS: APCI (+ve): 543 (M+1)

$^1$H NMR (300 MHz, DMSO-d6) (90° C.) δ 1.25 (t, J=6.7 Hz, 6H), 2.27 (s, 3H), 2.64 (t, J=6.4 Hz, 2H), 2.76 (d, J=12.9 Hz, 2H), 2.88 (t, J=7.8 Hz, 2H), 3.10-3.17 (m, 10H), 3.62 (t, J=6.9 Hz, 4H), 3.68 (t, J=6.9 Hz, 4H), 6.75 (d, J=9.1 Hz, 1H), 6.87 (d, J=9.1 Hz, 1H), 6.99 (d, J=7.5 Hz, 2H), 7.02 (s, 1H), 7.14 (t, J=7.2 Hz, 1H), 8.58 (d, J=67.6 Hz, 1H), 9.67 (s, 1H), 11.37 (s, 1H)

EXAMPLE 29

N-(2-Diethylaminoethyl)-N-{2-[2-(4-hydroxy-2-oxo-2,3-dihydro-1,3-benzothiazol-7-yl)ethylamino]ethyl}-3-[2-(3-hydroxyphenyl)ethoxy]propanamide dihydrobromide

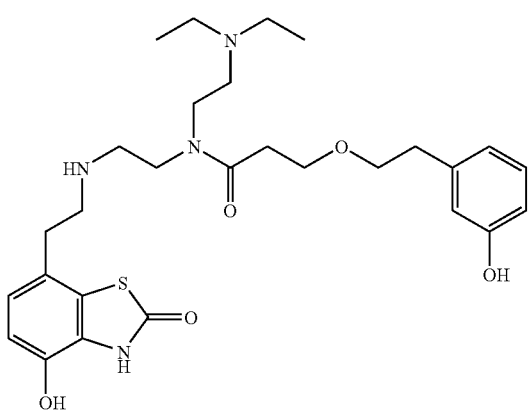

The product from Example 21 part f) was suspended in 48% aq HBr (1 ml) and heated in a microwave at 100° C. for 30 min. The resulting solution was evaporated, azeotroped with ethanol (×2) to give a residue which solidified on standing. The solid was triturated with acetonitrile and the white solid collected by filtration which was further purified by reverse phase HPLC. The desired product fractions were evaporated in vacuo, the residue dissolved in ethanol and conc. Aq. HBr (1 ml) was added. This solution was evaporated in vacuo and the residue azeotroped with ethanol (×5). The resulting solid was triturated with ethanol and collected by filtration to give the title compound as a white solid (10 mg).

MS: APCI (+ve): 545 (M+1)

$^1$H NMR (300 MHz, DMSO-d6, 90° C.) δ 1.26 (t, J=7.4 Hz, 6H), 2.64 (t, J=6.7 Hz, 2H), 2.72 (t, J=6.7 Hz, 2H), 2.92 (q, J=8.3 Hz, 2H), 3.15-3.22 (m, 100H), 3.61 (t, J=7.1 Hz, 4H), 3.68 (t, J=6.6 Hz, 4H), 6.58-6.63 (m, 3H), 6.76 (d, J=7.8 Hz, 1H), 6.88 (d, J=7.8 Hz, 1H), 7.04 (t, J=8.2 Hz, 1H), 8.67 (s, 1H), 9.62 (s, 1H), 11.31 (s, 1H)

EXAMPLE 30

N-(2-Diethylaminoethyl)-N-{2-[2-(4-hydroxy-2-oxo-2,3-dihydro-1,3-benzothiazol-7-yl)ethylamino]ethyl}-3-[2-(3-methoxyphenyl)ethoxy]propanamide dihydrobromide

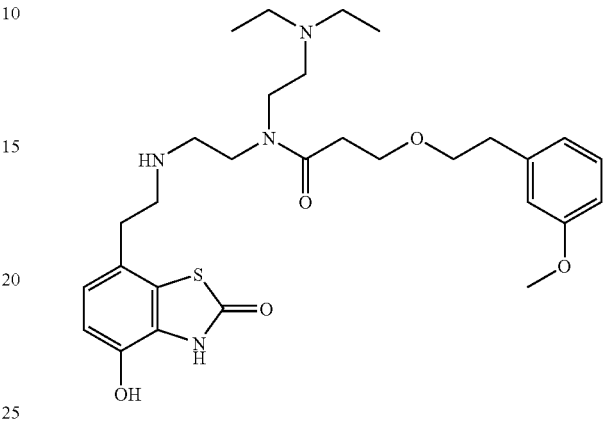

The reaction described in Example 29 also afforded N-(2-diethylaminoethyl)-N-{2-[2-(4-hydroxy-2-oxo-2,3-dihydro-1,3-benzothiazol-7-yl)ethylamino]ethyl}-3-[2-(3-methoxyphenyl)ethoxy]propionamide which was isolated and purified by reverse phase HPLC and converted to its dihydrobromide salt as described in Example 29. The title compound was obtained as an orange solid (4 mg).

MS: APCI (+ve): 559 (M+1)

$^1$H NMR (300 MHz, DMSO-d6, 90° C.) δ 1.25 (t, J=6.7 Hz, 6H), 2.64 (t, J=6.7 Hz, 2H), 2.78 (t, J=6.7 Hz, 2H), 2.86-2.92 (m, 4H), 3.14-3.20 (m, 10H), 3.61-3.71 (m, 6H), 3.73 (s, 3H), 6.73-6.79 (m, 4H), 6.88 (d, J=7.7 Hz, 1H), 7.17 (t, J=8.0 Hz, 1H), 8.63 (s, 1H), 9.62 (s, 1H), 11.29 (s, 1H)

EXAMPLE 31

3-[2-(2-Chlorophenyl)ethoxy]-N-(2-diethylaminoethyl)-N-{2-[2-(4-hydroxy-2-oxo-2,3-dihydro-1,3-benzothiazol-7-yl)ethylamino]ethyl}propanamide ditrifluoroacetate

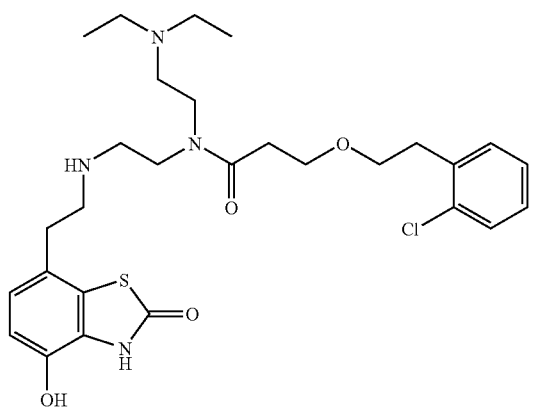

a) tert-Butyl 3-[2-(2-chlorophenyl)ethoxy]propanoate

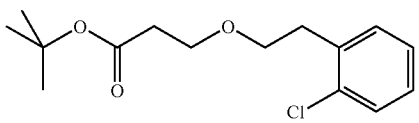

2-(2-Chlorophenyl)ethanol (2.5 g) was reacted using the method of Example 17 part d) to give the sub-title compound as a clear, colourless oil (4.24 g).

$^1$H NMR (300 MHz, DMSO) δ 2.42 (t, J=6.3 Hz, 2H), 2.93 (t, J=7.3 Hz, 2H), 3.61 (q, J=5.3 Hz, 4H), 7.24-7.29 (m, 2H), 7.37-7.44 (m, 2H).

b) 3-[2-(2-Chlorophenyl)ethoxy]propanoic Acid

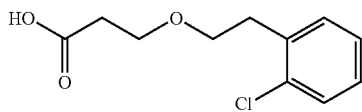

The product from part a) (4.24 g) was reacted using the method of Example 17 part e) to give the sub-title compound as an orange oil (4.37 g).

1H NMR (400 MHz, DMSO) δ 7.36-7.41 (m, 2H), 7.23-7.26 (m, 2H), 3.61 (t, J=6.2 Hz, 2H), 3.58 (t, J=6.8 Hz, 2H), 2.91 (t, J=6.8 Hz, 2H), 2.43 (t, J=6.8 Hz, 2H)

c) 3-[2-(2-Chlorophenyl)ethoxy]-N-(2-diethylamino-ethyl)-N-(2,2-dimethoxy-ethyl)propanamide

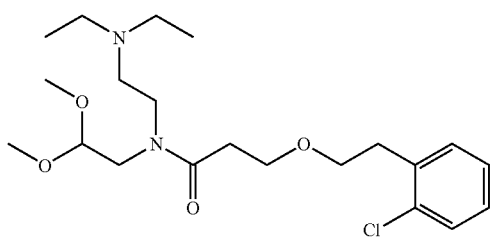

The product from part b) (1.0 g) was reacted with the product of example 16 part a) using the method of example 16 part b), substituting THF for DCM, and only stirring for 1 hour. Purification by chromatography on silica with 5% methanol in DCM gave the sub-title compound (1.21 g).

$^1$H NMR (400 MHz, DMSO) δ 0.91-0.97 (m, 6H), 2.42-2.48 (m, 4H), 2.54-2.59 (m, 2H), 2.91 (t, J=6.8 Hz, 2H), 3.26 (s, 3H), 3.31 (s, 3H), 3.37-3.40 (m, 2H), 3.57-3.67 (m, 4H), 4.42 (2×t, J=5.2, 5.2 Hz, 1H), 7.23-7.27 (m, 2H), 7.35-7.42 (m, 2H). 2×CH$_2$ not accounted for; possibly under the water or DMSO peak.

d) 3-[2-(2-Chlorophenyl)ethoxy]-N-(2-diethylamino-ethyl)-N-{2-[2-(4-hydroxy-2-oxo-2,3-dihydro-1,3-benzothiazol-7-yl)ethylamino]ethyl}propanamide ditrifluoroacetate The product from part c) (1.21 g) was dissolved in acetone (24 ml) and 2 spoonfuls of 4 A molecular sieves added. The mixture was cooled in ice, 4M HCl in dioxan (2.19 ml) added, stirred for 5 min and the ice bath removed. After 2 h, 4M HCl in dioxan (2.19 ml) and acetone (10 ml) were added, and the mixture was stirred for 2 hrs, filtered and then evaporated to dryness to give 3-[2-(2-chlorophenyl)ethoxy]-N-(2-diethylaminoethyl)-N-(2-oxoethyl)propanamide (539 mg). This was dissolved in NMP (3 ml) and added to a solution of the 7-(2-aminoethyl)-4-hydroxy-1,3-benzothiazol-2(3H)-one hydrochloride (396 mg) in NMP (3 ml), followed by the addition of sodium triacetoxyborohydride (1.02 g). After stirring for 1.5 h the mixture was cooled in an ice bath and quenched with water, and washed with ether (×2). The aqueous phase was neutralised with sodium bicarbonate, extracted with DCM (×5), and the combined organic solutions were dried (Na$_2$SO$_4$) and evaporated. The residue was purified using reverse phase HPLC to give the title compound as a clear colourless gum (36 mg).

MS: APCI (+ve): 563 (M+1)

$^1$H NMR (300 MHz, DMSO) d 1.21 (t, J=7.2 Hz, 6H), 2.61-2.68 (m, 2H), 2.83 (t, J=9.5 Hz, 2H), 2.94 (t, J=6.4 Hz, 2H), 3.25 (s, 10H), 3.54-3.70 (m, 8H), 6.73-6.78 (m, 1H), 6.84-6.88 (m, 1H), 7.24-7.30 (m, 2H), 7.35-7.44 (m, 2H), 10.13 (d, J=7.9 Hz, 1H), 11.75 (d, J=5.8 Hz, 1H)

EXAMPLE 32

N-[2-(Diethylamino)ethyl]-N-(2-{[2-(4-hydroxy-2-oxo-2,3-dihydro-1,3-benzothiazol-7-yl)ethyl]amino}ethyl)-3-[2-(2-naphthyl)ethoxy]propanamide

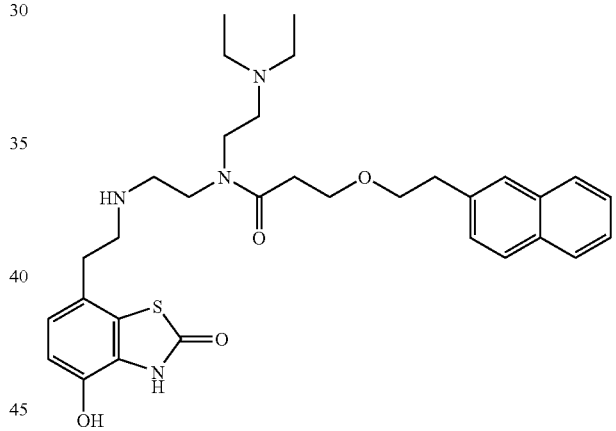

a) tert-Butyl 3-[2-(2-naphthyl)ethoxy]propanoate

2-Naphthalene ethanol (3 g) was treated with benzyltrimethylammonium hydroxide (Triton B®; 198 uL of a 40% solution in methanol). The methanol was removed by evaporation and residue azeotroped with toluene (×2). THF (5 ml) was added. The mixture was cooled to 0° C. and tert Butyl acrylate (2.45 g) added slowly. The mixture was stirred for 4 days. The majority of the THF was removed by evaporation, and the residue purified using silica column chromatography, eluting with isohexane, then 2:1 isohexane:ethyl acetate to give the sub-titled compound (4.96 g).

$^1$H NMR (299.947 MHz, DMSO) δ 1.35 (s, 9H), 2.41 (t, 2H), 2.96 (t, 2H), 3.61 (t, 2H), 3.68 (t, 2H), 7.39-7.50 (m, 3H), 7.72 (s, 1H), 7.80-7.87 (m, 3H)

b) 3-[2-(2-Naphthyl)ethoxy]propanoic Acid tert-Butyl 3-[2-(2-naphthyl)ethoxy]propanoate (Example 32a) (4.96 g) was dissolved in DCM (25 ml), and trifluoroacetic acid (25.5 ml) added. The mixture was stirred for 1 hour. The solvents were removed in vacuo, and the residue taken up in ether. The ether was washed with saturated bicarbonate solution (×3) and the aqueous layer was acidified with 2N HCl, then extracted with ether (×3), dried over magnesium sulfate, filtered and evaporated to give the sub-titled compound (3.66 g).

$^1$H NMR (399.826 MHz, DMSO) δ 2.45 (t, 2H), 2.97 (t, 2H), 3.64 (t, 2H), 3.68 (t, 2H), 7.40-7.50 (m, 3H), 7.74 (s, 1H), 7.82-7.87 (m, 3H)

c) N-[2-(Diethylamino)ethyl]-N-(2,2-dimethoxyethyl)-3-[2-(2-naphthyl)ethoxy]propanamide Oxalyl chloride (1.04 g) was added drop-wise to a solution of 3-[2-(2-naphthyl)ethoxy]propanoic acid (Example 32b), (1 g) in dichloromethane (10 ml). Dimethylformamide (1 drop) was added and stirring continued at room temperature for 30 minutes. The mixture was subsequently concentrated, azeotroped with toluene, re-dissolved in dichloromethane (5 ml) and added drop-wise to a solution of N-(2,2-dimethoxyethyl)-N,N-diethylethane-1,2-diamine (0.835 g) and N,N-diisopropylethylamine (1.05 g) in dichloromethane (5 ml). The resulting mixture was stirred at room temperature overnight. The reaction mixture was washed with saturated sodium bicarbonate solution (1×20 ml), water (1×20 ml), dried over sodium sulfate and concentrated to give the sub-titled compound (1.67 g).

m/e 431 (M+H$^+$)

$^1$H NMR (299.947 MHz, DMSO) δ 0.89 (t, 3H), 0.93 (t, 3H), 2.37-2.46 (m, 6H), 2.57 (q, 2H), 2.96 (t, 2H), 3.25 (s, 3H), 3.27-3.39 (m, 4H), 3.29 (s, 3H), 3.62-3.71 (m, 4H), 4.41 (tt, 1H), 7.39-7.50 (m, 3H), 7.73 (s, 1H), 7.81-7.87 (m, 3H)

d) N-[2-(Diethylamino)ethyl]-3-[2-(2-naphthyl)ethoxy]-N-(2-oxoethyl)propanamide N-[2-(Diethylamino)ethyl]-N-(2,2-dimethoxyethyl)-3-[2-(2-naphthyl)ethoxy]propanamide (Example 32c) (0.5 g) was dissolved in 4M HCl in dioxane (5.8 ml), and stirred for 10 mins. The reaction mixture was poured into saturated sodium bicarbonate solution (100 ml), which was then extracted with DCM (×4). The organic layers were combined, dried over sodium sulfate, filtered and evaporated to give the sub-titled compound (458 mg).

m/e 385 (M+H$^+$)

$^1$H NMR (299.947 MHz, DMSO) δ 0.84-0.96 (m, 6H), 2.38-2.47 (m, 6H), 2.65 (t, 2H), 2.97 (t, 2H), 3.19-3.34 (m, 2H), 3.38 (t, 2H), 3.60-3.72 (m, 4H), 7.40-7.50 (m, 3H), 7.73 (s, 1H), 7.81-7.87 (m, 3H), 9.23 (s, 1H)

e) N-[2-(Diethylamino)ethyl]-N-(2-{[2-(4-hydroxy-2-oxo-2,3-dihydro-1,3-benzothiazol-7-yl)ethyl]amino}ethyl)-3-[2-(2-naphthyl)ethoxy]propanamide 7-(2-Aminoethyl)-4-hydroxy-1,3-benzothiazol-2(3H)-one hydrochloride (176 mg) was dissolved in NMP (2 ml) to give a clear, yellow solution. Sodium hydroxide (27 mg) was dissolved in methanol (0.6 ml), and added in one portion to the yellow solution which turned bright orange. N-[2-(diethylamino)ethyl]-3-[2-(2-naphthyl)ethoxy]-N-(2-oxoethyl)propanamide (Example 32d) (458 mg) was dissolved in DCM (1 ml) and added drop-wise. The mixture was allowed to stir for 1 hour. Sodium triacetoxyborohydride (303 mg) was added portion-wise, and mixture stirred for 45 mins. Water (10 ml) was added followed by DCM, and the layers separated. The aqueous layer was extracted with DCM (×3). The remaining aqueous layer was found to contain desired material, so this was mixed with ethanol, then evaporated to dryness re-dissolved in methanol water mix, and loaded onto a pre-washed SCX cartridge. The cartridge was washed with 1:1 methanol:water, then methanol, then eluted with 0.07N methanolic ammonia to give a yellow film (178 mg). This was dissolved in ethanol, aqueous HBr (100 ul) added and the solution left to stand for 30 mins. The solvents were removed in vacuo to give a yellow solid, which was azeotroped with ethanol (×3). Ethanol was added and mixture sonicated to give a pale yellow suspension. Solid collected by filtration, and washed with ethanol to give the title compound (141 mg).

m/e 579.3 (M+H$^+$)

$^1$H NMR (399.826 MHz, DMSO, 90° C.) δ 1.19-1.23 (m, 6H), 2.67 (q, 2H), 2.85 (q, 2H), 2.98 (t, 2H), 3.13-3.17 (m, 8H), 3.55-3.65 (m, 4H), 3.67-3.75 (m, 4H), 6.77 (dd, 1H), 6.87 (t, 1H), 7.41-7.50 (m, 3H), 7.74 (s, 1H), 7.83-7.87 (m, 3H), 8.57 (s, 1H), 8.74 (s, 1H), 9.36 (d, 1H), 10.07 (d, 1H), 11.74 (d, 1H)

Biological Assays

Adrenergic β2 Mediated cAMP Production

Cell Preparation

H292 cells were grown in RPMI (Roswell Park Memorial Institute) medium containing, 10% (v/v) FBS (foetal bovine serum) and 2 mM L-glutamine. Cells were grown in 225 cm2 flasks containing 25 mL media in a humidified incubator at 37° C., 5% $CO_2$. Cells were harvested from the flask and passaged at a 1 in 10 dilution once per week.

Experimental Method

The media from flasks containing H292 cells was removed, rinsed with 10 mL PBS (phosphate buffered saline) and replaced with 10 mL Accutase™ cell detachment solution. Flasks were incubated for 15 minutes in a humidified incubator at 37° C., 5% $CO_2$. The cell suspension was counted and the cells re-suspended in RPMI media (containing 10% (v/v) FBS and 2 mM L-glutamine) at 0.05×10$^6$ cells per mL. 5000 cells in 100 μL were added to each well of a tissue-culture-treated 96-well plate and the cells incubated overnight in a humidified incubator at 37° C., 5% $CO_2$. The culture media was removed, washed twice with 100 μL assay buffer and replaced with 50 μL assay buffer. Cells were rested at room temperature for 20 minutes after which time 25 μL of rolipram (1.2 mM made up in assay buffer containing 2.4% (v/v) dimethylsulphoxide) was added. Cells were incubated with rolipram for 10 minutes after which time test compounds (made up as ×4 concentrated stocks in assay buffer containing 4% (v/v) dimethylsulphoxide) were added and the cells were incubated for 10 minutes at room temperature. Final rolipram concentration in the assay was 300 μM and final vehicle concentration was 1.6% (v/v) dimethylsulphoxide. The reaction was stopped by removing supernatants, washing once with 100 μL assay buffer and replacing with 50 μL lysis buffer. The cell monolayer was frozen at −80° C. for 30 minutes (or overnight).

AlphaScreen™ cAMP Detection

The concentration of cAMP (cyclic adenosine monophosphate) in the cell lysate was determined using the AlphaScreen™ methodology. The frozen cell plate was thawed for 20 minutes on a plate shaker then 10 μL of the cell lysate was transferred to a 96-well white plate. 40 μL of mixed AlphaScreen™ detection beads (containing equal volumes of donor beads (pre-incubated with biotinylated cAMP in the dark for 30 minutes) and acceptor beads), was added to each well and the plate incubated at room temperature for 10 hours in the dark. The AlphaScreen™ signal was measured using an EnVision spectrophotometer (Perkin-Elmer Inc.) with the recommended manufacturer's settings. cAMP concentrations were determined by reference to a calibration curve determined in the same experiment using standard cAMP concentrations (made up in lysis buffer in a 96-well tissue-culture-treated plate and frozen/thawed alongside the test samples) and detected using the same protocol. Concentration response curves for agonists were constructed to determine both the $pEC_{50}$ and Intrinsic Activity. Intrinsic Activity was expressed as a fraction relative to the maximum activity determined for formoterol in each experiment. The results obtained for a representative selection of the compounds of the Examples are shown in Table 1 below.

TABLE 1

| Compound of | $pEC_{50}$ | Intrinsic Activity |
|---|---|---|
| Example 1 | 7.2 | 0.7 |
| Example 5 | 7.9 | 0.8 |
| Example 8 | 8.9 | 0.7 |
| Example 10 | 8.3 | 0.6 |
| Example 12 | 7.8 | 0.8 |

Alternative Adrenergic β2 Mediated cAMP Production

Cell Preparation

H292 cells were grown in 225 cm2 flasks incubator at 37° C., 5% $CO_2$ in RPMI medium containing, 10% (v/v) FBS (foetal bovine serum) and 2 mM L-glutamine.

Experimental Method

Adherent H292 cells were removed from tissue culture flasks by treatment with Accutase™ cell detachment solution for 15 minutes. Flasks were incubated for 15 minutes in a humidified incubator at 37° C., 5% $CO_2$. Detached cells were re-suspended in RPMI media (containing 10% (v/v) FBS and 2 mM L-glutamine) at $0.05 \times 10^6$ cells per mL. 5000 cells in 100 μL were added to each well of a tissue-culture-treated 96-well plate and the cells incubated overnight in a humidified incubator at 37° C., 5% $CO_2$. The culture media was removed and cells were washed twice with 100 μL assay buffer and replaced with 50 μL assay buffer (HBSS solution containing 10 mM HEPES pH7.4 and 5 mM glucose). Cells were rested at room temperature for 20 minutes after which time 25 μL of rolipram (1.2 mM made up in assay buffer containing 2.4% (v/v) dimethylsulphoxide) was added. Cells were incubated with rolipram for 10 minutes after which time test compounds were added and the cells were incubated for 60 minutes at room temperature. The final rolipram concentration in the assay was 300 μM and final vehicle concentration was 1.6% (v/v) dimethylsulphoxide. The reaction was stopped by removing supernatants, washing once with 100 μL assay buffer and replacing with 50 μL lysis buffer. The cell monolayer was frozen at −80° C. for 30 minutes (or overnight).

AlphaScreen™ cAMP Detection

The concentration of cAMP (cyclic adenosine monophosphate) in the cell lysate was determined using AlphaScreen™ methodology. The frozen cell plate was thawed for 20 minutes on a plate shaker then 10 μL of the cell lysate was transferred to a 96-well white plate. 40 μL of mixed AlphaScreen™ detection beads pre-incubated with biotinylated cAMP, was added to each well and the plate incubated at room temperature for 10 hours in the dark. The AlphaScreen™ signal was measured using an EnVision spectrophotometer (Perkin-Elmer Inc.) with the recommended manufacturer's settings. cAMP concentrations were determined by reference to a calibration curve determined in the same experiment using standard cAMP concentrations. Concentration response curves for agonists were constructed and data was fitted to a four parameter logistic equation to determine both the $pEC_{50}$ and Intrinsic Activity. Intrinsic Activity was expressed as a fraction relative to the maximum activity determined for formoterol in each experiment. Results for compounds of the invention are to be found in Table 2.

Selectivity Assays

Adrenergic α1D

Membrane Preparation

Membranes were prepared from human embryonic kidney 293 (HEK293) cells expressing recombinant human $α1_D$ receptor. These were diluted in Assay Buffer (50 mM HEPES, 1 mM EDTA, 0.1% gelatin, pH 7.4) to provide a final concentration of membranes that gave a clear window between maximum and minimum specific binding.

Experimental Method

Assays were performed in U-bottomed 96-well polypropylene plates. 10 μL [$^3$H]-prazosin (0.3 nM final concentration) and 10 μL of test compound (10× final concentration) were added to each test well. For each assay plate 8 replicates were obtained for [$^3$H]-prazosin binding in the presence of 10 μL vehicle (10% (v/v) DMSO in Assay Buffer; defining maximum binding) or 10 μL BMY7378 (10 μM final concentration; defining non-specific binding (NSB)). Membranes were then added to achieve a final volume of 100 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-prazosin binding) were determined using serial dilutions typically in the range 0.1 nM to 10 μM. Data was fitted to a four parameter logistic equation to determine the compound potency, which was expressed as pIC50 (negative log molar concentration inducing 50% inhibition of [$^3$H]-prazosin binding). Results are shown in Table 2 below.

Adrenergic β1

Membrane Preparation

Membranes containing recombinant human adrenergic beta 1 receptors were obtained from Euroscreen. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 10 μL [$^{125}$I]-Iodocyanopindolol (0.036 nM final concentration) and 10 μL of test compound (10× final concentration) were added to each test well. For each assay plate 8 replicates were obtained for [$^{125}$I]-Iodocyanopindolol binding in the presence of 10 μL vehicle (10% (v/v) DMSO in Assay Buffer; defining maximum binding) or 10 μL Propranolol (10 μM final concentration; defining non-specific binding (NSB)). Membranes were then added to achieve a final volume of 100 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^{125}$I]-Iodocyanopindolol binding) were determined using serial dilutions typically in the range 0.1 nM to 10 μM. Data was fitted to a four parameter logistic equation to determine the compound potency, which was expressed as $pIC_{50}$ (negative log molar concentration inducing 50% inhibition of [$^{125}$I]-Iodocyanopindolol binding). Results are shown in Table 2 below.

Dopamine D2

Membrane Preparation

Membranes containing recombinant human Dopamine Subtype D2s receptors were obtained from Perkin Elmer. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 30 μL [$^3$H]-spiperone (0.16 nM final concentration) and 30 μL of test compound (10× final concentration) were added to each test well. For each assay plate 8 replicates were obtained for [$^3$H]-spiperone binding in the presence of 30 μL vehicle (10% (v/v) DMSO in Assay Buffer; defining maximum binding) or 30 μL Haloperidol (10 μM final concentration; defining non-specific binding (NSB)). Membranes were then added to achieve a final volume of 300 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-spiperone binding) were determined using serial dilutions typically in the range 0.1 nM to 10 μM. Data was fitted to a four parameter logistic equation to determine the compound potency, which was expressed as $pIC_{50}$ (negative log molar concentration inducing 50% inhibition of [$^3$H]-spiperone binding).

The results obtained for a representative selection of the compounds of the Examples are shown in Table 2 below.

Onset Assay

Dunkin-Hartley guinea-pigs (between 200 g and 300 g on delivery) were supplied by a designated breeding establishment. The guinea-pigs were killed by cervical dislocation and the trachea removed. The adherent connective tissue was removed and each trachea cut into four rings. The tissue rings were then attached to an isometric transducer. The tissues were washed and a force of 1 g was applied to each ring. In all experiments a paired curve design was used. A priming dose of 1 μM methacholine was applied to the tissues. The tissues were then washed (three times, one minute between washes), the resting tension of 1 g was reapplied and the tissues were allowed to rest for 1 hour to equilibrate. Tissues were then contracted with 1 μM methacholine and once a steady response was obtained a cumulative concentration response curve to isoprenaline ($10^{-9}$ M-$10^{-5}$ M) was constructed. The tissues were then washed (three times, one minute between washes) and left to rest for an hour. At the end of the resting period the tissues were contracted with 1 μM methacholine and a $p[A]_{50}$ concentration of test compound added. Once the tissue had reached maximum relaxation, a 30×$p[A]_{50}$ concentration of test compound was added.

Once the tissue response had reached a plateau, 10 μM sotalol was added to the bath to confirm that the relaxation was $\beta_2$ mediated Data were collected using the ADInstruments chart4 for windows software, which measured the maximum tension generated at each concentration of agonist.

For each concentration of the isoprenaline cumulative concentration curve, the response was calculated as % relaxation of the methacholine-induced contraction. A curve was plotted of $\log_{10}$[agonist] (M) versus percentage inhibition of the methacholine-induced contraction. These data were then fitted to a non-linear regression curve fit. For each experiment, E/[A] curve data were fitted using a 4-parameter logistic function of the form:

$$E = \beta + \frac{(\beta - \alpha) \cdot [A]^m}{[A]^m + [A]_{50}^m}$$

E and [A] are the pharmacological effect (% relaxation) and concentration of the agonist respectively; α, β, $[A]_{50}$ and m are the asymptote, baseline, location and slope parameters, respectively. The $p[A]_{50}$ and IA of each isoprenaline curve was determined from this fit, to determine if the tissue was viable for generating an onset time for the test compounds.

For each $p[A]_{50}$ concentration of the test compound, the response was calculated as % relaxation of the methacholine-induced contraction. The results were plotted % relaxation against time and the time taken to reach a 90% relaxation value was calculated and recorded.

The addition of a 30×$p[A]_{50}$ concentration enabled determination of the maximum compound effect within the individual tissue. Hence, the % of the maximum compound effect at the $p[A]_{50}$ concentration was calculated and recorded.

The results obtained for a representative selection of the compounds of the Examples are shown in Table 2 below.

Pharmacokinetics in the Rat

A dose solution of the test compound was prepared using a suitable dose vehicle. The concentration of the compound in the dose solution was assayed by diluting an aliquot to a nominal concentration of 50 µg·ml$^{-1}$ and calibrating against duplicate injections of a standard solution and a QC standard at this concentration. Compounds were administered intravenously as a bolus into a caudal vein to groups of three 250-350 g rats (approximately 1 ml·kg$^{-1}$). For the oral dose, a separate group of 2 or 3 animals were dosed by oral gavage (3 ml·kg$^{-1}$). Delivered doses were estimated by weight loss. Food was not usually withdrawn from animals prior to dosing, although this effect was investigated if necessary.

Blood samples (0.25 ml) were taken into 1 ml syringes from the caudal vein, transferred to EDTA tubes and plasma was prepared by centrifugation (5 min at 13000 rpm) soon after sample collection, before storage at −20° C. Typical sampling times were 2, 4, 8, 15, 30, 60, 120, 180, 240, 300 (min) or until the terminal t1/2 was accurately described.

The concentration of the analyte(s) were determined in plasma by quantitative mass spectrometry. Standard and quality control stock solutions were prepared at a concentration 1 mg/ml in methanol. A range of standard and QC stocks produced by serial dilution were added to control rat plasma (50 µl). The range of concentrations covered the range of levels of analyte present in the rat samples. Standards, QCs and samples underwent liquid extraction using 50 µl of organic solvent and 100 µl of organic solvent containing an internal standard, chosen to closely resemble the analyte. The samples were then mixed by repeated inversion, stored at −20° C. for at least 1 h, and centrifuged at 3500 rpm in a centrifuge for 20 minutes. Aliquots (120 µl) of each sample were transferred for analysis using LC-MSMS. Standard and quality control samples covering the range of concentrations found in the test samples were within 25% of the nominal concentration.

Pharmacokinetic data analysis was achieved using Win-Nonlin. A standard non-compartmental analysis was used to estimate the parameters such as Tmax, Cmax, Lambda_z, t1/2_Lambda_z. AUCall, AUCINF (observed), CI (observed), Vss (observed).

The results obtained for t1/2 for a representative selection of the compounds of the Examples are shown in Table 2 below.

TABLE 2

| Example No. | β2 pEC50 | β2 Int Act | α1 bind pIC50 | β1 bind p IC50 | D2 bind pIC50 |
|---|---|---|---|---|---|
| 10 | 8.1 | 0.7 | | | |
| 12 | 8.1 | 0.8 | | 5 | 5 |
| 13 | 7.2 | 0.5 | | | |

TABLE 2-continued

| Example No. | β2 pEC50 | β2 Int Act | α1 bind pIC50 | β1 bind p IC50 | D2 bind pIC50 |
|---|---|---|---|---|---|
| 14 | 8.1 | 1 | | 5 | 5 |
| 15 | 8.2 | 0.8 | 6.6 | 5 | 6.1 |
| 17 | 7.6 | 0.9 | 6.1 | | |
| 18 | 8.3 | 0.7 | 6.1 | 5 | 5.6 |
| 19 | 7.9 | 0.8 | | | |
| 20 | 8 | 0.6 | 6.4 | 5 | 5.8 |
| 21 | 7.1 | 0.6 | | | |
| 22 | 8.1 | 0.8 | 5.9 | 5 | 5.3 |
| 24 | 7 | 0.9 | | | |
| 25 | 7.2 | 0.8 | | | |
| 26 | 7.8 | 0.6 | 5.5 | 6 | 5.9 |
| 27 | 7.5 | 0.6 | 6 | 5 | 5.5 |
| 28 | 8.5 | 0.6 | 5.9 | 6 | 6 |
| 29 | 8.2 | 0.8 | 5.9 | 5 | 6.6 |
| 31 | 7.7 | 0.9 | 6.6 | 5 | 5.3 |
| 32 | 8 | 0.5 | 6.2 | 5 | 6.1 |

Note that empty boxes in Table 2 indicate that there is not yet any data available for the activity of that Example on the screen.

The invention claimed is:

1. N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide; or a pharmaceutically acceptable salt thereof.

2. N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide.

3. N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide.

4. A pharmaceutical composition comprising N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide; or a pharmaceutically acceptable salt thereof in association with a pharmaceutically acceptable adjuvant, diluent or carrier.

5. A pharmaceutical composition comprising N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide in association with a pharmaceutically acceptable adjuvant, diluent or carrier.

6. A pharmaceutical composition comprising N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide in association with a pharmaceutically acceptable adjuvant, diluent or carrier.

* * * * *

UNITED STATES PATENT AND TRADEMARK OFFICE
CERTIFICATE OF CORRECTION

PATENT NO. : 7,709,511 B2  Page 1 of 1
APPLICATION NO. : 12/063322
DATED : May 4, 2010
INVENTOR(S) : Roger Bonnert et al.

It is certified that error appears in the above-identified patent and that said Letters Patent is hereby corrected as shown below:

Face of Patent, right hand column, in the Abstract, "$R^4$, $R^5$, $R^4$, $R^5$," should read -- $R^4$, $R^5$, $R^{4'}$, $R^{5'}$, --.

Signed and Sealed this

Second Day of November, 2010

David J. Kappos
*Director of the United States Patent and Trademark Office*